US010189879B2

(12) United States Patent
Yamamoto et al.

(10) Patent No.: US 10,189,879 B2
(45) Date of Patent: Jan. 29, 2019

(54) DNA-BINDING PROTEIN USING PPR MOTIF, AND USE THEREOF

(71) Applicants: KYUSHU UNIVERSITY, NATIONAL UNIVERSITY CORPORATION, Fukuoka-shi, Fukuoka (JP); HIROSHIMA UNIVERSITY, Higashihiroshima-Shi, Hiroshima (JP)

(72) Inventors: Takashi Yamamoto, Higashihiroshima (JP); Tetsushi Sakuma, Higashihiroshima (JP); Takahiro Nakamura, Fukuoka (JP); Yusuke Yagi, Fukuoka (JP); Yasuyuki Okawa, Fukuoka (JP)

(73) Assignees: KYUSHU UNIVERSITY, NAT'L UNIVERSITY CORPORATION, Fukuoka-Shi (JP); HIROSHIMA UNIVERSITY, Higashihiroshima-Shi (JP)

(*) Notice: Subject to any disclaimer, the term of this patent is extended or adjusted under 35 U.S.C. 154(b) by 0 days.

(21) Appl. No.: 14/785,952

(22) PCT Filed: Apr. 22, 2014

(86) PCT No.: PCT/JP2014/061329
§ 371 (c)(1),
(2) Date: Oct. 21, 2015

(87) PCT Pub. No.: WO2014/175284
PCT Pub. Date: Oct. 30, 2014

(65) Prior Publication Data
US 2016/0075744 A1     Mar. 17, 2016

(30) Foreign Application Priority Data
Apr. 22, 2013 (JP) ................................. 2013-089840

(51) Int. Cl.
C12N 9/22 (2006.01)
C07K 14/415 (2006.01)
C12N 15/82 (2006.01)
C12N 15/85 (2006.01)

(52) U.S. Cl.
CPC .............. *C07K 14/415* (2013.01); *C12N 9/22* (2013.01); *C12N 15/8213* (2013.01); *C12N 15/8216* (2013.01); *C12N 15/8217* (2013.01); *C12N 15/85* (2013.01); *C07K 2319/80* (2013.01); *C12Y 301/21004* (2013.01)

(58) Field of Classification Search
CPC .............. C07K 14/415; C07K 2319/80; C07K 2319/85
See application file for complete search history.

(56) References Cited

U.S. PATENT DOCUMENTS

2014/0335521 A1    11/2014    Nakamura et al.

FOREIGN PATENT DOCUMENTS

| WO | 2011/072246 A2 | 6/2011 |
| WO | 2011/111829 A1 | 9/2011 |
| WO | 2013/058404 A1 | 4/2013 |

OTHER PUBLICATIONS

Pfalz et al. 2006; pTAC2, -6, and -12 are components of the transcriptionally active plastid chromosome that are required for plastid gene expression. The Plant Cell 18:176-197.*
Maeder, Morgan L., et al., "Rapid "Open-Source" Engineering of Customized Zinc-Finger Nucleases for Highly Efficient Gene Modification", Molecular Call Technique, Cell Press, Elsevier Inc., Jul. 25, 2008, pp. 294-301.
Urnov, Fyodor D., et al., "Genome editing with engineered zinc finger nucleases", Nature Reviews Genetics, Macmillan Publishers Limited, vol. 11, Sep. 2010, pp. 636-646.
Miller, Jeffrey C., et al., "A Tale nuclease architecture for efficient genome editing", Nature Biotechnology, Mature America, Inc., vol. 29, No. 2, Feb. 2011, pp. 143-148.
Mali, Prashant, et al., "RNA-Guided Human Genome Engineering via Cas9", Science, vol. 339, Feb. 15, 2013, pp. 823-826.

(Continued)

*Primary Examiner* — Karen Cochrane Carlson
(74) *Attorney, Agent, or Firm* — Westerman, Hattori, Daniels & Adrian, LLP

(57) ABSTRACT

The object of the present invention is to, by analyzing PPR proteins that act to bind to DNA with a prediction that RNA recognition rules of PPR motifs can also be used for recognition of DNA, find a PPR protein showing such a characteristic. According to the present invention, it was revealed that, with a protein that can bind in a DNA base-selective manner or a DNA base sequence-specific manner, which contains one or more, preferably 2 to 30, more preferably 5 to 25, most preferably 9 to 15, of PPR motifs having a structure of the following formula 1 (wherein, in the formula 1, Helix A is a part that can form an α-helix structure; X does not exist, or is a part consisting of 1 to 9 amino acids; Helix B is a part that can form an α-helix structure; and L is a part consisting of 2 to 7 amino acids), and having a specific combination of amino acids corresponding to a DNA base or DNA base sequence as amino acids of three positions of No. 1 A.A., No. 4 A.A., in Helix A of the formula 1 and No. "ii" (−2) A. A. contained in L of the formula 1, the aforementioned object could be achieved.

(Helix A)-X-(Helix B)-L                    (Formula 1)

2 Claims, 7 Drawing Sheets
Specification includes a Sequence Listing.

(56) References Cited

OTHER PUBLICATIONS

Cong, Le et al., "Multiplex Genome Engineering Using CRISPR/Cas Systems", Science, American Association for the Advancement of Science, vol. 339, 2013, pp. 819-823.
Small, Ian D., et al., "The PPR motif—a TPR-related motif prevalent in plant organellar proteins", Trends in Biochemical Science, Mar. 2000, pp. 46-47.
Woodson, Jesse D., et al., "Coordination of gene expression between organellar and nuclear genomes", Nature Reviews Genetics, Nature Publishing Group, May 2008, vol. 9, pp. 383-395.
Wang, Xiaoqiang, et al., Modular Recognition of RNA by a Human Pumilio-Homology Domain, Cell Press, vol. 110, Aug. 23, 2002, pp. 501-512.
Sheong, Cheom-Gil et al., "Engineering RNA sequence specificity of Pumilio repeats", Proceeding of the National Academy of Sciences, USA, vol. 103, No. 37, Sep. 12, 2006, pp. 13635-13639.
Ikeda, Tatsuya A., et al., "Characterization of a DNA-Binding Protein Implicated in Transcription in Wheat Mitochondra", Molecular and Cellular Biology, vol. 19 No. 12, Dec. 1999, pp. 8113-8122.
Koussevitzky, Shai, et al., "Signals from Chloroplasts Converge to Regulate Nuclear Gene Expression", Science, vol. 316, May 4, 2007, pp. 715-719.
Pfalz, Jeannette, et al., "pTAC2, -6, and -12 Are Components of the Transcriptionally Active Plastid Chromosome That Are Required for Plastid Gene Expression", The Plant Cell, American Society of Plant Biologists, vol. 18:Jan. 2006, pp. 176-197.
Chi, Wei et al., "The Pentratricopeptide Repeat Protein Delayed Greening1 Is Involved in the Regulation of Early Chloroplast Development and Chloroplast Gene Expression in Arabidopsis", Plant Physiology, American Society of Plant Biologists, vol. 147, Jun. 2008, pp. 573-584.
Ding, Yong-He, et al., "Arabidopsis Glutamine-Rich Protein 23 Is Essential for Early Embryogenesis and Encodes a Novel Nuclear PPR Motif Protein That Interacts with RNA Polymerase II Subunit III", The Plant Cell, vol. 18, American Society of Plant Biologists, Apr. 2006, pp. 815-830.
Kobayashi, Keiko et al., "Identification and characterization of the RNA binding surface of the pentatricopeptide repeat protein", Nucleic Acids Research, Oxford University Press, vol. 40, No. 6, Nov. 29, 2011, pp. 2712-2723.
Barkan, Alice et al., "A Combinatorial Amino Acid Code for RNA Recognition by Pentatricopeptide Repeat Proteins", PLOS Genetics, Aug. 16, 2012, vol. 8, Issue 8, pp. 1-8.
Yagi, Yusuke et al., "Elucidation of the RNA Recognition Code for Pentatricopeptide Repeat Proteins Involved in Organelle RNA Editing in Plants", PLOS One, vol. 8, Issue 3, Mar. 2013, pp. 1-8.
Yusuke, Yagi et al., "The Molecular Biology Society of Japan Nenkai Program", Nov. 20, 2013, vol. 36, pp. 1-2.
International Search Report dated Aug. 12, 2014, issued in Internal Application No. PCT/JP2014/061329 (7 pages).
Japanese verison of International Preliminary Report on Patentability (Form PCT/IB/326) issued in counterpart International Application No. PCT/JP2014/061329 dated Aug. 12, 2014, with PCT/IB/373, PCT/ISA/237 (5 pages).
English verison of International Preliminary Report on Patentability (Form PCT/IB/338) issued in counterpart International Application No. PCT/JP2014/061329 dated Aug. 12, 2014, with PCT/IB/373, PCT/ISA/237 (6 pages).
Cushing, D. et al, "Arabidopsis emb175 and Other ppr Knockout Mutants Reveal Essential Roles for Pentatricopeptide Repeat (PPR) Proteins in Plant Embryogenesis", Planta, An International Journal of Plant Biology, Jun. 2005, vol. 221, No. 3, pp. 424-436; cited in Extended (supplementary) European Search Report dated Nov. 3, 2016.
Ahsan, N. et al, "Excess Copper Induced Physiological and Proteomic Changes in Germinating Rice Seeds", Chemospehre, Feb. 2, 2007, vol. 67, No. 6, pp. 1182-1193; cited in Extended (supplementary) European Search Report dated Nov. 3, 2016.
Uyttewaal, M. et al, "PPR336 is Associated with Polysomes in Plant Mitochondria", Journal of Molecular Biology, Nov. 13, 2007, vol. 375, No. 3, pp. 626-636; cited in Extended (supplementary) European Search Report dated Nov. 3, 2016.
Kobayashi, T. et al, "Development of Genome Engineering Tools from Plant-Specific PPR Proteins Using Animal Cultured Cells", Methods in Molecular Biology, 2016, vol. 1469, pp. 147-155; cited in Extended (supplementary) European Search Report dated Nov. 3, 2016.
Extended (supplementary) European Search Report dated Nov. 3, 2016, issued in counterpart European Application No. 14787853.2. (12 pages).
First Examination Report dated Sep. 28, 2017, issued in counterpart Australian Application No. 2014258386. (6 pages).
Office Action dated Mar. 9, 2018, issued in counterpart European Application No. 14 787 853.2 (9 pages).
Nakamura, Takahiro et al., ; "RNA-binding properties of HCF152, an Arabidopsis PPR protein involved in the processing of chloroplast RNA : RNA-binding of a PPR protein", European Journal of Biochemistry, vol. 270, No. 20, Sep. 17, 2003, pp. 4070-4081, Cited in European Office Action dated Mar. 9, 2018.
Nilliams-Carrier, R. et al., "Sequence-specific binding of a chloroplast pentatricopeptide repeat protein to its native group II intron ligand", RNA, vol. 14, No. 9, Jul. 24, 2008, pp. 1930-1941, Cited in European Office Action dated Mar. 9, 2018.
Ban,Ting et al., "Structure of a PLS-class Pentatricopeptide Repeat Protein Provides Insights into Mechanism of RNA Recognition", Journal of Biological Chemistry, vol. 288, No. 44, Sep. 18, 2013, pp. 31540-31548, Cited in European Office Action dated Mar. 9, 2018.
Office Action dated May 31, 2018, issued in counterpart Chinese Application No. 201480035686.6, with English translation. (12 pages).
Office Action dated Jun. 5, 2018, issued in counterpart Japanese Application No. 2015-190124, with English translation. (7 pages).

* cited by examiner

FIG. 2

PPR proteins that function in DNA metabolism

| Name | Architecture | Assay |
|---|---|---|
| p63 (612 aa) (Wheat) | 9 x PPR | DNA binding (gel shift assay) activation of in vitro transcription |
| pTac2 (862 aa) (Arabidopsis) | 15 x PPR Smr | Loss of transcription in vivo (Run-On assay) |
| GUN1 (862 aa) (Arabidopsis) | 11 x PPR Smr Poly-Thr | DNA binding (pull-down assay) |
| DG1 (798 aa) (Arabidopsis) | 10 x PPR | Loss of transcription in vivo (Run-On assay) |
| GRP23 (913 aa) (Arabidopsis) | Leucine Zipper 11 x PPR WQQ | Embryonic lethal Interaction with pol2 large subunit via WQQ (Two hybrid, BiFC) |

[Fig. 3]
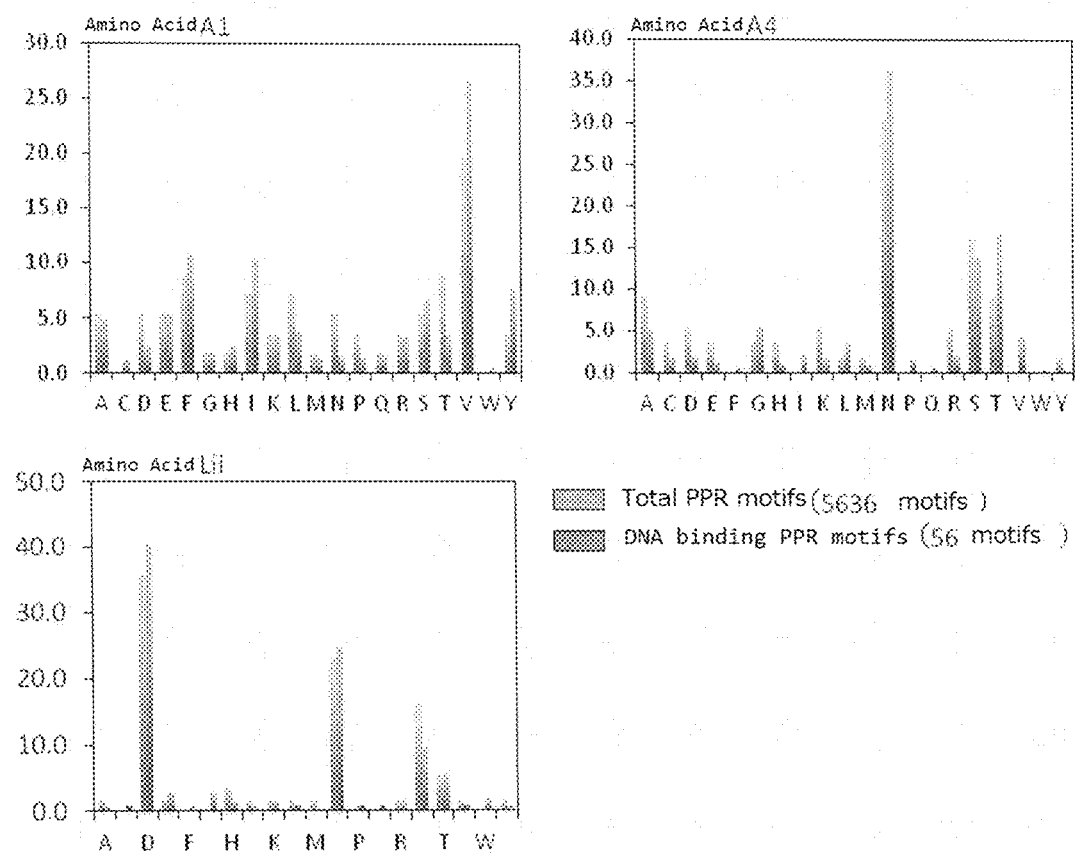

[Fig. 4-1]

(A) The positions of the PPR motifs, and the positions of No. 1 A.A., No. 4 A.A., and No. "ii" (-2) A.A. for *Arabidopsis thaliana* p63 (SEQ ID NO: 1)

| Motif No. | AA No. | Seqence | Amino Acid Insertion between PPR motifs |
|---|---|---|---|
| 1 | 230-264 | VLYRTLLANCVAAGNVKKSELVFNKMKDLGFPLSG | - |
| 2 | 265-298 | FTCDQMLLLHKRIDRKKIADVLLLMEKENIKPSL | - |
| 3 | 299-333 | LTYKILIDVKGATNDISGMEQILETMKDEGVELDF | - |
| 4 | 334-368 | QTQALTARHYSGAGLKDKAEKVLKEMEGESLEANR | - |
| 5 | 369-399 | RAFKDLLSIYASLGREDEVKRIWKICESKPY | P |
| 6 | 401-435 | EESLAAIQAFGKLNKVQEAEAIFEKIVKMDRRASS | - |
| 7 | 436-470 | STYSVLLRVYVDHKMLSKGKDLVKRMAESGCRIEA | - |
| 8 | 471-505 | TTWDALIKLYVEAGEVEKADSLLDKASKQSHTKLM | N |
| 9 | 507-541 | NSFMYIMDEYSKRGDVHNTEKIFLKMREAGYTSRL | - |

(B) The positions of the PPR motifs, and the positions of No. 1 A.A., No. 4 A.A., and No. "ii" (-2) A.A. for the GUN1 protein of *Arabidopsis thaliana* (SEQ ID NO: 2)

| Motif No. | AA No. | Seqence | Amino Acid Insertion between PPR motifs |
|---|---|---|---|
| 1 | 234-268 | KLASAMISTLGRYGKVTIAKRIFETAFAGGYGNTV | - |
| 2 | 269-303 | YAFSALISAYGRSGLHEEAISVFNSMKEYGLRPNL | - |
| 3 | 304-339 | VTYNAVIDACGKGGMEFKQVAKPFDEMQRNGVQPDR | - |
| 4 | 340-374 | ITFNSLLAVCSPGGLWEAARNLFDEMTNRRIEQDV | - |
| 5 | 375-409 | FSYNTLLDAICKGGQMDLAFEILAQMPVKRIMPNV | - |
| 6 | 410-444 | VSYSTVIDGFAKAGRFDEALNLFGEMRYLGIALDR | - |
| 7 | 445-479 | VSYNTLLSIYTKVGRSEEALDILREMASVGIKKDV | - |
| 8 | 480-514 | VTYNALLGGYGKQGKYDEVKKVFTEMKREHVLPNL | - |
| 9 | 515-549 | LTYSTLIDGYSKGGLYKEAMEIFREFKSAGLRADV | - |
| 10 | 550-584 | VLYSALIDALCKNGLVGSAVSLIDEMTKEGISPNV | - |
| 11 | 585-621 | VTYNSIIDAFGRSATMDRSADYSNGGSLPFSSSALSA | - |

[Fig. 4-2]

(C) The positions of the PPR motifs, and the positions of No. 1 A.A., No. 4 A.A., and No. "ii" (-2) A.A. for pTac2 of *Arabidopsis thaliana* (SEQ ID NO: 3)

| Motif No. | AA No. | Seqence | Amino Acid Insertion between PPR motifs |
|---|---|---|---|
| 1 | 106-141 | NDFALVFKFFAGRGDWQRSLPLFKYNQPQIWCKPNE | -- |
| 2 | 142-176 | HIYTIMISLLGREGLLDKCLEVFDEMPSQGVSRSV | -- |
| 3 | 177-211 | FSYTALINAYGRNGRYETSLELLDRMKNEKISPSI | -- |
| 4 | 212-247 | LTYNTVINACARGGLDWEGLLGLFAEMRREGIQPDI | -- |
| 5 | 248-282 | VTYNTLLSACAIRGLGDEAEMVFRTMNDGGIVPDL | -- |
| 6 | 283-317 | TTYSHLVETFGKLRRLEKVCDLLGEMASGGSLPDI | -- |
| 7 | 318-352 | TSYNVLLEAYAKSGSIKEAMGVFSQMQAAGCTFNA | -- |
| 8 | 353-387 | NTYSVLLRLFGQSGRYDDVRQLFLEMKSSNTDPDA | -- |
| 9 | 388-422 | ATYNILIEVFGEGGYFKEVVTLFHDMVEENIEPDM | -- |
| 10 | 423-457 | ETYEGIIFACGKGGLREDARKILQYMFANDIVPSS | -- |
| 11 | 458-492 | KAYTGVIEAFGQAALYEEALVAFNTMREVGSNPSI | -- |
| 12 | 493-527 | ETFHSLLYSFARGGLVKESEAILSRLVDSGIPRNR | -- |
| 13 | 528-562 | DTFNAQIEAYKQGGKFEEAVKTYVDMEKSRCDPDE | -- |
| 14 | 563-597 | RTLEAVLSVYSFARLVDECREQFEEMKASDILPSI | -- |
| 15 | 598-632 | MCYCMMLAVYGKTERWDDVNELLEEMLGNRVSNIR | -- |

(D) The positions of the PPR motifs, and the positions of No. 1 A.A., No. 4 A.A., and No. "ii" (-2) A.A. for DG1 (SEQ ID NO: 4).

| Motif No. | AA No. | Seqence | Amino Acid Insertion between PPR motifs |
|---|---|---|---|
| 1 | 256-286 | FVYTKLLSVLGFARRPQEALQIFNQMLGDRQ | LYPDM |
| 2 | 292-326 | AAYHCIAVTLGQAGLLKELLAVIERMRQKPTKLTK | NLKQKNWDPVLRPDI |
| 3 | 342-376 | VVYNAILNACVPTLQWKAVSWVPVELRKNGLRPNG | -- |
| 4 | 377-411 | ATYGLAMEVMLESGKFDRVHDFFRKMKSSEEAPKA | -- |
| 5 | 412-446 | ITYKVLVRALWREGKIEEAVEAVRDMEQKGVIGTG | -- |
| 6 | 447-482 | SVYYELACCLCNNGRWCDAMLEVGRMERLENCRPLR | -- |
| 7 | 483-513 | ITFTGLIAASLNGGHVDDCMAIFQYMKDKCD | PNI |
| 8 | 517-547 | GTANMMLKVYGRNDMFSEAKELFEEIVSRKE | TRLVFNS |
| 9 | 555-589 | YTYSFMLEASABRLQWEYFERVYQTMVLSGYQMDQ | -- |

[Fig. 4-3]

(E) The positions of the PPR motifs, and the positions of No. 1 A.A., No. 4 A.A., and No. "ii" (-2) A.A. for GRP23 of *Arabidopsis thaliana* (SEQ ID NO: 5)

| Motif No. | AA No. | Seqence | Amino Acid Insertion between PPR motifs |
|---|---|---|---|
| 1 | 181-216 | FTCNAIIAAMYRAKRYSESISLFQYFFRQSNIVPNV | -- |
| 2 | 217-252 | VSYNQIINAHCDEGNVDEALEVYRHILANAPFAPSS | -- |
| 3 | 253-287 | VTYRHLTKGLVQAGRIGDAASLLREMLSKGQAADS | -- |
| 4 | 288-318 | TVYNNLIRGYLDLGDFDKAVEFFDELKSKCT | VYDG |
| 5 | 323-357 | IVNATFMEYWFEKGNDKEAMESYRSLLDKKFRMHP | -- |
| 6 | 358-392 | PTGNVLLEVFLKFGKKDEAWALFNEMLDNHAPPNI | -- |
| 7 | 398-428 | DIVGIMVNECFKMGEFSEAINTFKKVGSKVT | SKPFVMDY |
| 8 | 437-471 | LGYCNIVTRFCEQGMLTEAERFFAEGVSRSLPADA | -- |
| 9 | 472-506 | PSHRAMIDAYLKAERIDDAVKMLDRMVDVNLRVVA | -- |
| 10 | 507-541 | DFGARVFGELIKNGKLTESAEVLTKMGEREPKPDP | -- |
| 11 | 542-576 | SIYDVVVRGLCDGDALDQAKDIVGEMIRHNVGVTT | -- |

[Fig. 5]
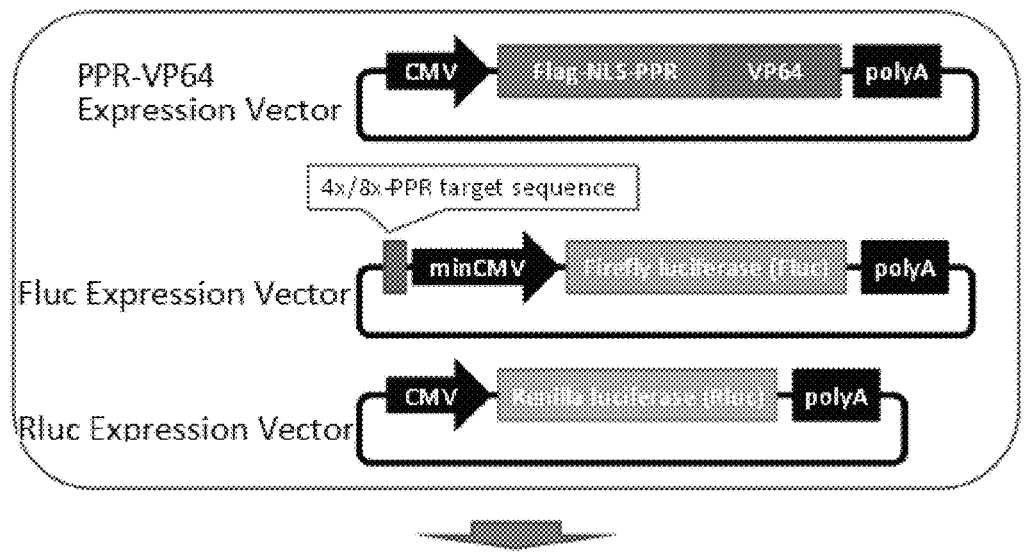
Transfection into huma culture cells (HEK293 cells)
Measurement of Activity by Luciferase Assay
[Fig. 6]
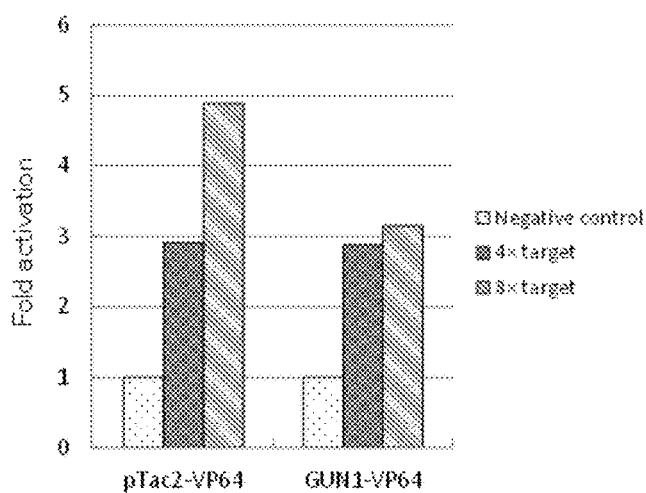

DNA-BINDING PROTEIN USING PPR MOTIF, AND USE THEREOF

TECHNICAL FIELD

The present invention relates to a protein that can selectively or specifically bind to an intended DNA base or DNA sequence. According to the present invention, a pentatricopeptide repeat (PPR) motif is utilized. The present invention can be used for identification and design of a DNA-binding protein, identification of a target DNA of a protein having a PPR motif, and functional control of DNA. The present invention is useful in the fields of medicine, agricultural science, and so forth. The present invention also relates to a novel DNA-cleaving enzyme that utilizes a complex of a protein containing a PPR motif and a protein that defines a functional region.

BACKGROUND ART

In recent years, techniques of binding nucleic acid-binding protein factors elucidated through various analyses to an intended sequence have been established, and they are coming to be used. Use of this sequence-specific binding is enabling analysis of intracellular localization of a target nucleic acid (DNA or RNA), elimination of a target DNA sequence, or expression control (activation or inactivation) of a protein-encoding gene existing downstream of a target DNA sequence.

There are being conducted researches and developments using the zinc finger protein (Non-patent documents 1 and 2), TAL effecter (TALE, Non-patent document 3, Patent document 1), and CRISPR (Non-patent documents 4 and 5) as protein factors that act on DNA as materials for protein engineering. However, types of such protein factors are still extremely limited.

For example, the artificial enzyme, zinc finger nuclease (ZFN), known as an artificial DNA-cleaving enzyme, is a chimera protein obtained by binding a part that is constituted by linking 3 to 6 zinc fingers that specifically recognize a DNA consisting of 3 or 4 nucleotides and bind to it, and recognizes a nucleotide sequence in a sequence unit of 3 or 4 nucleotides with one DNA cleavage domain of a bacterial DNA-cleaving enzyme (for example, FokI) (Non-patent document 2). In such a chimera protein, the zinc finger domain is a protein domain that is known to bind to DNA, and it is based on the knowledge that many transcription factors have the aforementioned domain, and bind to a specific DNA sequence to control expression of a gene. By using two of ZFNs each having three zinc fingers, cleavage of one site per 70 billion nucleotides can be induced in theory.

However, because of the high cost required for the production of ZFNs, etc., the methods using ZFNs have not come to be widely used yet. Moreover, functional sorting efficiency of ZFNs is bad, and it is suggested that the methods have a problem also in this respect. Furthermore, since a zinc finger domain consisting of n of zinc fingers tends to recognize a sequence of (GNN)n, the methods also have a problem that degree of freedom for the target gene sequence is low.

An artificial enzyme, TALEN, has also been developed by binding a protein consisting of a combinatory sequence of module parts that can recognize every one nucleotide, TAL effecter (TALE), with a DNA cleavage domain of a bacterial DNA-cleaving enzyme (for example, FoId), and it is being investigated as an artificial enzyme that can replace ZFNs (Non-patent document 3). This TALEN is an enzyme generated by fusing a DNA binding domain of a transcription factor of a plant pathogenic *Xanthomonas* bacterium, and the DNA cleavage domain of the DNA restriction enzyme FoId, and it is known to bind to a neighboring DNA sequence to form a dimer and cleave a double strand DNA. Since, as for this molecule, the DNA binding domain of TALE found from a bacterium that infects with plants recognize one base with a combination of amino acids at two sites in the TALE motif consisting of 34 amino acid residues, it has a characteristic that binding property for a target DNA can be chosen by choosing the repetitive structure of the TALE module. TALEN using the DNA binding domain that has such a characteristic as mentioned above has a characteristic that it enables introduction of mutation into a target gene, like ZFNs, but the significant superiority thereof to ZFNs is that degree of freedom for the target gene (nucleotide sequence) is markedly improved, and the nucleotide to which it binds can be defined with a code.

However, since the total conformation of TALEN has not been elucidated, the DNA cleavage site of TALEN has not been identified at present. Therefore, it has a problem that cleavage site of TALEN is inaccurate, and is not fixed, compared with ZFNs, and it also cleaves even a similar sequence. Therefore, it has a problem that a nucleotide sequence cannot be accurately cleaved at an intended target site with a DNA-cleaving enzyme. For these reasons, it is desired to develop and provide a novel artificial DNA-cleaving enzyme free from the aforementioned problems.

On the basis of genome sequence information, PPR proteins (proteins having a pentatricopeptide repeat (PPR) motif) constituting a big family of no less than 500 members only for plants have been identified (Non-patent document 6). The PPR proteins are nucleus-encoded proteins, but are known to act on or involved in control, cleavage, translation, splicing, RNA edition, and RNA stability chiefly at an RNA level in organelles (chloroplasts and mitochondria) in a gene-specific manner. The PPR proteins typically have a structure consisting of about 10 contiguous 35-amino acid motifs of low conservativeness, i.e., PPR motifs, and it is considered that the combination of the PPR motifs is responsible for the sequence-selective binding with RNA. Almost all the PPR proteins consist only of repetition of about 10 PPR motifs, and any domain required for exhibiting a catalytic action is not found in many cases. Therefore, it is considered that the PPR proteins are essentially RNA adapters (Non-patent document 7).

In general, binding of a protein and DNA, and binding of a protein and RNA are attained by different molecular mechanisms. Therefore, a DNA-binding protein generally does not bind to RNA, whereas an RNA-binding protein generally does not bind to DNA. For example, in the case of the pumilio protein, which is known as an RNA-binding factor, and can encode RNA to be recognized, binding thereof to DNA has not been reported (Non-patent documents 8 and 9).

However, in the process of investigating properties of various kinds of PPR proteins, it became clear that it could be suggested that some types of the PPR proteins worked as DNA-binding factors.

The wheat p63 is a PPR protein having 9 PPR motifs, and it is suggested by gel shift assay that it binds to DNA in a sequence-specific manner (Non-patent document 10).

The GUN1 protein of *Arabidopsis thaliana* has 11 PPR motifs, and it is suggested by pull down assay that it binds with DNA (Non-patent document 11).

It has been demonstrated by run-on assay that the *Arabidopsis thaliana* pTac2 (protein having 15 PPR motifs, Non-patent document 12) and *Arabidopsis thaliana* DG1 (protein having 10 PPR motifs, Non-patent document 12) directly participate in transcription for generating RNA by using DNA as a template, and they are considered to bind to DNA.

An *Arabidopsis thaliana* strain deficient in the gene of GRP23 (protein having 11 PPR motifs, Non-patent document 14) shows the phenotype of embryonal death. It has been demonstrated that this protein physically interacts with the major subunit of the eukaryotic RNA transcription polymerase 2, which is a DNA-dependent RNA transcription enzyme, and therefore it is considered that GRP23 also acts to bind to DNA.

However, bindings of these PPR proteins to DNA have been only indirectly suggested, and actual sequence-specific binding has not been fully verified. Moreover, even if such proteins bind with DNA, it is generally considered that binding of a protein and DNA, and binding of a protein and RNA are attained by different molecular mechanisms, and therefore what kind of sequence rule specifically exists, with which binding is attained, etc, are not even expected at all.

PRIOR ART REFERENCES

Patent Documents

Patent document 1: WO2011/072246
Patent document 2: WO2011/111829

Non-Patent Documents

Non-patent document 1: Maeder, M. L., et al. (2008) Rapid "open-source" engineering of customized zinc-finger nucleases for highly efficient gene modification, Mol. Cell 31, 294-301
Non-patent document 2: Urnov, F. D., et al. (2010) Genome editing with engineered zinc finger nucleases, Nature Review Genetics, 11, 636-646
Non-patent document 3: Miller, J. C., et al. (2011) A TALE nuclease architecture for efficient genome editing, Nature Biotech., 29, 143-148
Non-patent document 4: Mali P., et al. (2013) RNA-guided human genome engineering via Cas9, Science, 339, 823-826
Non-patent document 5: Cong L, et al. (2013) Multiplex genome engineering using CRISPR/Cas systems, Science, 339, 819-823
Non-patent document 6: Small, I. D. and Peeters, N. (2000) The PPR motif—a TPR-related motif prevalent in plant organellar proteins, Trends Biochem. Sci., 25, 46-47
Non-patent document 7: Woodson, J. D., and Chory, J. (2008) Coordination of gene expression between organellar and nuclear genomes, Nature Rev. Genet., 9, 383-395
Non-patent document 8: Wang, X., et al. (2002) Modular recognition of RNA by a human pumilio-homology domain, Cell, 110, 501-512
Non-patent document 9: Cheong, C. G., and Hall and T. M. (2006) Engineering RNA sequence specificity of Pumilio repeats, Proc. Natl. Acad. Sci. USA 103, 13635-13639
Non-patent document 10: Ikeda T. M. and Gray M. W. (1999) Characterization of a DNA-binding protein implicated in transcription in wheat mitochondria, Mol. Cell Bio., 119 (12):8113-8122
Non-patent document 11: Koussevitzky S., et al. (2007) Signals from chloroplasts converge to regulate nuclear gene expression, Science, 316:715-719
Non-patent Document 12: Pfalz J, et al. (2006) PTAC2, -6, and -12 are components of the transcriptionally active plastid chromosome that are required for plastid gene expression, Plant Cell 18:176-197
Non-patent document 13: Chi W, et al. (2008) The pentatricopeptide repeat protein DELAYED GREENING1 is involved in the regulation of early chloroplast development and chloroplast gene expression in *Arabidopsis*, Plant Physiol., 147:573-584
Non-patent document 14: Ding Y H, et al. (2006) *Arabidopsis* GLUTAMINE-RICH PROTEIN 23 is essential for early embryogenesis and encodes a novel nuclear PPR motif protein that interacts with RNA polymerase II subunit III, Plant Cell, 18:815-830

SUMMARY OF THE INVENTION

Object to be Achieved by the Invention

The inventors of the present invention expected that the properties of the PPR proteins (proteins having a PPR motif) as RNA adapters would be determined by property of each PPR motif constituting the PPR proteins and combination of a plurality of PPR motifs, and proposed methods for modifying RNA-binding proteins using such PPR motifs (Patent document 2). Then, they elucidated that a PPR motif and RNA bind in one-to-one correspondence, contiguous PPR motifs recognize contiguous RNA bases in an RNA sequence, and such RNA recognition is determined by combination of amino acids at specific three positions among the 35 amino acids constituting the PPR motif, and filed a patent application for a method for designing a customized RNA-binding protein utilizing RNA recognition codes of PPR motifs and use thereof (PCT/JP2012/077274; Yagi, Y., et al. (2013) PLoS One, 8, e57286; and Barkan, A., et al. (2012) PLoS Genet., 8, e1002910).

It has been generally considered that binding of a protein and DNA, and binding of a protein and RNA are attained by different molecular mechanisms. However, the inventors of the present invention predicted that the RNA recognition rule of the PPR motif would be also usable for recognition of DNA, and analyzed PPR proteins that act to bind with DNA aiming at retrieving PPR proteins having such a characteristic. They also aimed at providing a novel artificial enzyme by preparing a customized DNA-binding protein that binds to a desired sequence using such a PPR protein that specifically binds to a DNA obtained as described above, and using it with a protein that defines a functional region, and providing a novel artificial DNA-cleaving enzyme by using it together with a region having a DNA-cleaving activity as the functional region.

Means for Achieving the Object

As for the PPR proteins, it was elucidated by various domain search programs (Pfam, Prosite, Interpro, etc.) that the PPR motifs contained in the common RNA-binding type PPR proteins and the PPR motifs contained in the DNA-binding PPR proteins of some kinds mentioned above are not particularly distinguished. Therefore, it was considered that PPR proteins might contain amino acids (amino acid group) that would determine a binding property for DNA or a binding property for RNA apart from the amino acids required for the nucleic acid recognition.

The inventors of the present invention elucidated that an RNA-binding PPR motif and RNA bind in one-to-one correspondence, contiguous PPR motifs recognize contiguous RNA bases in an RNA sequence, and in such recognition, base-selective binding with RNA is determined by combination of RNA recognition amino acids at specific three positions (that is, the first and fourth amino acids of the first helix (Helix A) among the two α-helix structures constituting the motif (No. 1 A.A. and No. 4 A.A.), and the second amino acid counted from the C-terminus (No. "ii" (−2) A.A.)), among the 35 amino acids constituting the PPR motif, and filed a patent application for a method for designing a customized RNA-binding protein utilizing RNA recognition codes of PPR motifs and use thereof (PCT/JP2012/077274).

Then, among the PPR proteins, for the aforementioned wheat p63 (Non-patent document 11, the amino acid sequence of the homologous protein of *Arabidopsis thaliana* is shown as SEQ ID NO: 1), GUN1 protein of *Arabidopsis thaliana* (Non-patent document 12, amino acid sequence thereof is shown as SEQ ID NO: 2), pTac2 of *Arabidopsis thaliana* (Non-patent document 13, amino acid sequence thereof is shown as SEQ ID NO: 3), DG1 (Non-patent document 14, amino acid sequence thereof is shown as SEQ ID NO: 4), and GRP23 of *Arabidopsis thaliana* (Non-patent document 15, amino acid sequence thereof is shown as SEQ ID NO: 5), for which binding with DNA was suggested, amino acid frequencies of the amino acids at three positions bearing the nucleic acid recognition codes in the PPR motif considered to be important when RNA is a target (No. 1 A.A., No. 4 A.A. and No. "ii" (−2) A.A.) were compared with those found in the RNA binding type motif. As a result, it became clear that the tendencies of the amino acid frequencies found in those PPR motifs as mentioned above, for which DNA-binding property was suggested, and the RNA binding type motifs substantially agreed with each other.

The above results suggest that the nucleic acid recognition codes of the RNA binding type PPR motifs can also be applied to the DNA binding type PPR motifs. Thymine (T) is a uracil (U) derivative having a structure consisting of uracil (U) of which carbon of the 5-position is methylated, as it is also called 5-methyluracil. Such a characteristic of the base constituting the nucleic acid suggests that the combination of the amino acids that recognizes uracil (U) of an RNA binding type PPR motif is used for recognition of thymine (T) in DNA.

On the basis of the aforementioned findings, it was elucidated that, by using the aforementioned p63 (amino acid sequence of SEQ ID NO: 1), GUN1 protein of *Arabidopsis thaliana* (amino acid sequence of SEQ ID NO: 2), pTac2 of *Arabidopsis thaliana* (amino acid sequence of SEQ ID NO: 3), DG1 (amino acid sequence of SEQ ID NO: 4), and GRP23 of *Arabidopsis thaliana* (amino acid sequence of SEQ ID NO: 5), which are DNA-binding type PPR proteins, as a template, arranging amino acids of the three positions (No. 1 A.A., No. 4 A.A. and No. "ii" (−2) A.A.) with applying the finding obtained for such PPR proteins as a result of examination of the RNA-binding type PPR motifs, a customized DNA-binding protein that binds to an arbitrary DNA base sequence could be produced.

That is, the inventors of the present invention provided a protein that comprises 2 or more, preferably 2 to 30, more preferably 5 to 25, most preferably 9 to 15, of PPR motifs having the specific amino acids described later as the amino acids at the three positions (No. 1 A.A., No. 4 A.A., and No. "ii" (−2) A.A.) in the PPR motifs, and can bind to DNA in a DNA base-selective manner or DNA base sequence-selective manner, of which typical examples are the amino acid sequences of SEQ ID NOS: 1 to 5, and thus accomplished the present invention.

The present invention provides the followings.

[1] A protein that can bind in a DNA base-selective manner or a DNA base sequence-specific manner, which contains one or more PPR motifs having a structure of the following formula 1:

[Formula 1]

$$(\text{Helix A})\text{-}X\text{-}(\text{Helix B})\text{-}L \quad \quad (\text{Formula 1})$$

(wherein, in the formula 1:
Helix A is a part that can form an α-helix structure;
X does not exist, or is a part consisting of 1 to 9 amino acids;
Helix B is a part that can form an α-helix structure; and
L is a part consisting of 2 to 7 amino acids),
wherein,
under the following definitions:
the first amino acid of Helix A is referred to as No. 1 amino acid (No. 1 A.A.), the fourth amino acid as No. 4 amino acid (No. 4 A.A.), and
when a next PPR motif ($M_{n+1}$) contiguously exists on the C-terminus side of the PPR motif ($M_n$) (when there is no amino acid insertion between the PPR motifs), the −2nd amino acid counted from the end (C-terminus side) of the amino acids constituting the PPR motif ($M_n$);
   when a non-PPR motif consisting of 1 to 20 amino acids exists between the PPR motif ($M_n$) and the next PPR motif ($M_{n+1}$) on the C-terminus side, the amino acid locating upstream of the first amino acid of the next PPR motif ($M_{n+1}$) by 2 positions, i.e., the −2nd amino acid; or
   when any next PPR motif ($M_{n+1}$) does not exist on the C-terminus side of the PPR motif ($M_n$), or 21 or more amino acids constituting a non-PPR motif exist between the PPR motif ($M_n$) and the next PPR motif ($M_{n+1}$) on the C-terminus side, the 2nd amino acid counted from the end (C-terminus side) of the amino acids constituting the PPR motif ($M_n$)
is referred to as No. "ii" (−2) amino acid (No. "ii" (−2) A.A.),
one PPR motif ($M_n$) contained in the protein is a PPR motif having a specific combination of amino acids corresponding to a target DNA base or target DNA base sequence as the three amino acids of No. 1 A.A., No. 4 A.A., and No. "ii" (−2) A.A.

[2] The protein according to [1], wherein the combination of the three amino acids of No. 1 A.A., No. 4 A.A., and No. "ii" (−2) A.A. is a combination corresponding to a target DNA base or target DNA base sequence, and the combination of amino acids is determined according to any one of the following definitions:

(1-1) when No. 4 A.A. is glycine (G), No. 1 A.A. may be an arbitrary amino acid, and No. "ii" (−2) A.A. is aspartic acid (D), asparagine (N), or serine (S);
(1-2) when No. 4 A.A. is isoleucine (I), each of No. 1 A.A. and No. "ii" (−2) A.A. may be an arbitrary amino acid;
(1-3) when No. 4 A.A. is leucine (L), each of No. 1 A.A. and No. "ii" (−2) A.A. may be an arbitrary amino acid;
(1-4) when No. 4 A.A. is methionine (M), each of No. 1 A.A. and No. "ii" (−2) A.A. may be an arbitrary amino acid;
(1-5) when No. 4 A.A. is asparagine (N), each of No. 1 A.A. and No. "ii" (−2) A.A. may be an arbitrary amino acid;
(1-6) when No. 4 A.A. is proline (P), each of No. 1 A.A. and No. "ii" (−2) A.A. may be an arbitrary amino acid;

(1-7) when No. 4 A.A. is serine (S), each of No. 1 A.A. and No. "ii" (−2) A.A. may be an arbitrary amino acid;
(1-8) when No. 4 A.A. is threonine (T), each of No. 1 A.A. and No. "ii" (−2) A.A. may be an arbitrary amino acid; and
(1-9) when No. 4 A.A. is valine (V), each of No. 1 A.A. and No. "ii" (−2) A.A. may be an arbitrary amino acid.

[3] The protein according to [1], wherein the combination of the three amino acids of No. 1 A.A., No. 4 A.A., and No. "ii" (−2) A.A. is a combination corresponding to a target DNA base or target DNA base sequence, and the combination of amino acids is determined according to any one of the following definitions:

(2-1) when the three amino acids, No. 1 A.A., No. 4 A.A., and No. "ii" (−2) A.A. are an arbitrary amino acid, glycine, and aspartic acid, respectively, the PPR motif selectively binds to G;
(2-2) when the three amino acids, No. 1 A.A., No. 4 A.A., and No. "ii" (−2) A.A., are glutamic acid, glycine, and aspartic acid, respectively, the PPR motif selectively binds to G;
(2-3) when the three amino acids, No. 1 A.A., No. 4 A.A., and No. "ii" (−2) A.A., are an arbitrary amino acid, glycine, and asparagine, respectively, the PPR motif selectively binds to A;
(2-4) when the three amino acids, No. 1 A.A., No. 4 A.A., and No. "ii" (−2) A.A., are glutamic acid, glycine, and asparagine, respectively, the PPR motif selectively binds to A;
(2-5) when the three amino acids, No. 1 A.A., No. 4 A.A., and No. "ii" (−2) A.A., are an arbitrary amino acid, glycine, and serine, respectively, the PPR motif selectively binds to A, and next binds to C;
(2-6) when the three amino acids, No. 1 A.A., No. 4 A.A., and No. "ii" (−2) A.A., are an arbitrary amino acid, isoleucine, and an arbitrary amino acid, respectively, the PPR motif selectively binds to T and C;
(2-7) when the three amino acids, No. 1 A.A., No. 4 A.A., and No. "ii" (−2) A.A., are an arbitrary amino acid, isoleucine, and asparagine, respectively, the PPR motif selectively binds to T, and next binds to C;
(2-8) when the three amino acids, No. 1 A.A., No. 4 A.A., and No. "ii" (−2) A.A., are an arbitrary amino acid, leucine, and an arbitrary amino acid, respectively, the PPR motif selectively binds to T and C;
(2-9) when the three amino acids, No. 1 A.A., No. 4 A.A., and No. "ii" (−2) A.A., are an arbitrary amino acid, leucine, and aspartic acid, respectively, the PPR motif selectively binds to C;
(2-10) when the three amino acids, No. 1 A.A., No. 4 A.A., and No. "ii" (−2) A.A., are an arbitrary amino acid, leucine, and lysine, respectively, the PPR motif selectively binds to T;
(2-11) when the three amino acids, No. 1 A.A., No. 4 A.A., and No. "ii" (−2) A.A., are an arbitrary amino acid, methionine, and an arbitrary amino acid, respectively, the PPR motif selectively binds to T;
(2-12) when the three amino acids, No. 1 A.A., No. 4 A.A., and No. "ii" (−2) A.A., are an arbitrary amino acid, methionine, and aspartic acid, respectively, the PPR motif selectively binds to T;
(2-13) when the three amino acids, No. 1 A.A., No. 4 A.A., and No. "ii" (−2) A.A., are isoleucine, methionine, and aspartic acid, respectively, the PPR motif selectively binds to T, and next binds to C;
(2-14) when the three amino acids, No. 1 A.A., No. 4 A.A., and No. "ii" (−2) A.A., are an arbitrary amino acid, asparagine, and an arbitrary amino acid, respectively, the PPR motif selectively binds to C and T;
(2-15) when the three amino acids, No. 1 A.A., No. 4 A.A., and No. "ii" (−2) A.A., are an arbitrary amino acid, asparagine, and aspartic acid, respectively, the PPR motif selectively binds to T;
(2-16) when the three amino acids, No. 1 A.A., No. 4 A.A., and No. "ii" (−2) A.A., are phenylalanine, asparagine, and aspartic acid, respectively, the PPR motif selectively binds to T;
(2-17) when the three amino acids, No. 1 A.A., No. 4 A.A., and No. "ii" (−2) A.A., are glycine, asparagine, and aspartic acid, respectively, the PPR motif selectively binds to T;
(2-18) when the three amino acids, No. 1 A.A., No. 4 A.A., and No. "ii" (−2) A.A., are isoleucine, asparagine, and aspartic acid, respectively, the PPR motif selectively binds to T;
(2-19) when the three amino acids, No. 1 A.A., No. 4 A.A., and No. "ii" (−2) A.A., are threonine, asparagine, and aspartic acid, respectively, the PPR motif selectively binds to T;
(2-20) when the three amino acids, No. 1 A.A., No. 4 A.A., and No. "ii" (−2) A.A. are valine, asparagine, and aspartic acid, respectively, the PPR motif selectively binds to T, and next binds to C;
(2-21) when the three amino acids, No. 1 A.A., No. 4 A.A., and No. "ii" (−2) A.A. are tyrosine, asparagine, and aspartic acid, respectively, the PPR motif selectively binds to T, and next binds to C;
(2-22) when the three amino acids, No. 1 A.A., No. 4 A.A., and No. "ii" (−2) A.A., are an arbitrary amino acid, asparagine, and asparagine, respectively, the PPR motif selectively binds to C;
(2-23) when the three amino acids, No. 1 A.A., No. 4 A.A., and No. "ii" (−2) A.A., are isoleucine, asparagine, and asparagine, respectively, the PPR motif selectively binds to C;
(2-24) when the three amino acids, No. 1 A.A., No. 4 A.A., and No. "ii" (−2) A.A., are serine, asparagine, and asparagine, respectively, the PPR motif selectively binds to C;
(2-25) when the three amino acids, No. 1 A.A., No. 4 A.A., and No. "ii" (−2) A.A., are valine, asparagine, and asparagine, respectively, the PPR motif selectively binds to C;
(2-26) when the three amino acids, No. 1 A.A., No. 4 A.A., and No. "ii" (−2) A.A., are an arbitrary amino acid, asparagine, and serine, respectively, the PPR motif selectively binds to C;
(2-27) when the three amino acids, No. 1 A.A., No. 4 A.A., and No. "ii" (−2) A.A., are valine, asparagine, and serine, respectively, the PPR motif selectively binds to C;
(2-28) when the three amino acids, No. 1 A.A., No. 4 A.A., and No. "ii" (−2) A.A., are an arbitrary amino acid, asparagine, and threonine, respectively, the PPR motif selectively binds to C;
(2-29) when the three amino acids, No. 1 A.A., No. 4 A.A., and No. "ii" (−2) A.A., are valine, asparagine, and threonine, respectively, the PPR motif selectively binds to C;
(2-30) when the three amino acids, No. 1 A.A., No. 4 A.A., and No. "ii" (−2) A.A., are an arbitrary amino acid, asparagine, and tryptophan, respectively, the PPR motif selectively binds to C, and next binds to T;
(2-31) when the three amino acids, No. 1 A.A., No. 4 A.A., and No. "ii" (−2) A.A., are isoleucine, asparagine, and tryptophan, respectively, the PPR motif selectively binds to T, and next binds to C;

(2-32) when the three amino acids, No. 1 A.A., No. 4 A.A., and No. "ii" (−2) A.A., are an arbitrary amino acid, proline, and an arbitrary amino acid, respectively, the PPR motif selectively binds to T;
(2-33) when the three amino acids, No. 1 A.A., No. 4 A.A., and No. "ii" (−2) A.A., are an arbitrary amino acid, proline, and aspartic acid, respectively, the PPR motif selectively binds to T;
(2-34) when the three amino acids, No. 1 A.A., No. 4 A.A., and No. "ii" (−2) A.A., are phenylalanine, proline, and aspartic acid, respectively, the PPR motif selectively binds to T;
(2-35) when the three amino acids, No. 1 A.A., No. 4 A.A., and No. "ii" (−2) A.A., are tyrosine, proline, and aspartic acid, respectively, the PPR motif selectively binds to T;
(2-36) when the three amino acids, No. 1 A.A., No. 4 A.A., and No. "ii" (−2) A.A., are an arbitrary amino acid, serine, and an arbitrary amino acid, respectively, the PPR motif selectively binds to A and G;
(2-37) when the three amino acids, No. 1 A.A., No. 4 A.A., and No. "ii" (−2) A.A., are an arbitrary amino acid, serine, and asparagine, respectively, the PPR motif selectively binds to A;
(2-38) when the three amino acids, No. 1 A.A., No. 4 A.A., and No. "ii" (−2) A.A., are phenylalanine, serine, and asparagine, respectively, the PPR motif selectively binds to A;
(2-39) when the three amino acids, No. 1 A.A., No. 4 A.A., and No. "ii" (−2) A.A., are valine, serine, and asparagine, respectively, the PPR motif selectively binds to A;
(2-40) when the three amino acids, No. 1 A.A., No. 4 A.A., and No. "ii" (−2) A.A., are an arbitrary amino acid, threonine, and an arbitrary amino acid, respectively, the PPR motif selectively binds to A and G;
(2-41) when the three amino acids, No. 1 A.A., No. 4 A.A., and No. "ii" (−2) A.A., are an arbitrary amino acid, threonine, and aspartic acid, respectively, the PPR motif selectively binds to G;
(2-42) when the three amino acids, No. 1 A.A., No. 4 A.A., and No. "ii" (−2) A.A., are valine, threonine, and aspartic acid, respectively, the PPR motif selectively binds to G;
(2-43) when the three amino acids, No. 1 A.A., No. 4 A.A., and No. "ii" (−2) A.A., are an arbitrary amino acid, threonine, and asparagine, respectively, the PPR motif selectively binds to A;
(2-44) when the three amino acids, No. 1 A.A., No. 4 A.A., and No. "ii" (−2) A.A., are phenylalanine, threonine, and asparagine, respectively, the PPR motif selectively binds to A;
(2-45) when the three amino acids, No. 1 A.A., No. 4 A.A., and No. "ii" (−2) A.A., are isoleucine, threonine, and asparagine, respectively, the PPR motif selectively binds to A;
(2-46) when the three amino acids, No. 1 A.A., No. 4 A.A., and No. "ii" (−2) A.A., are valine, threonine, and asparagine, respectively, the PPR motif selectively binds to A;
(2-47) when the three amino acids, No. 1 A.A., No. 4 A.A., and No. "ii" (−2) A.A., are an arbitrary amino acid, valine, and an arbitrary amino acid, respectively, the PPR motif binds with A, C, and T, but does not bind to G;
(2-48) when the three amino acids, No. 1 A.A., No. 4 A.A., and No. "ii" (−2) A.A., are isoleucine, valine, and aspartic acid, respectively, the PPR motif selectively binds to C, and next binds to A;
(2-49) when the three amino acids, No. 1 A.A., No. 4 A.A., and No. "ii" (−2) A.A., are an arbitrary amino acid, valine, and glycine, respectively, the PPR motif selectively binds to C; and
(2-50) when the three amino acids, No. 1 A.A., No. 4 A.A., and No. "ii" (−2) A.A., are an arbitrary amino acid, valine, and threonine, respectively, the PPR motif selectively binds to T.

[4] The protein according to any one of [1] to [3], which contains 2 to 30 of the PPR motifs ($M_n$) defined in [1].
[5] The protein according to any one of [1] to [3], which contains 5 to 25 of the PPR motifs ($M_n$) defined in [1].
[6] The protein according to any one of [1] to [3], which contains 9 to 15 of the PPR motifs ($M_n$) defined in [1].
[7] The PPR protein according to [6], which consists of a sequence selected from the amino acid sequence of SEQ ID NO: 1 containing 9 PPR motifs, the amino acid sequence of SEQ ID NO: 2 containing 11 PPR motifs, the amino acid sequence of SEQ ID NO: 3 containing 15 PPR motifs, the amino acid sequence of SEQ ID NO: 4 containing 10 PPR motifs, and the amino acid sequence of SEQ ID NO: 5 containing 11 PPR motifs.
[8] A method for identifying a DNA base or DNA base sequence that serves as a target of a DNA-binding protein containing one or more (preferably 2 to 30) PPR motifs ($M_n$) defined in [1], wherein:
the DNA base or DNA base sequence is identified by determining presence or absence of a DNA base corresponding to a combination of the three amino acids of No. 1 A.A., No. 4 A.A., and No. "ii" (−2) A.A. of the PPR motif on the basis of any one of the definitions (1-1) to (1-9) mentioned in [2], and (2-1) to (2-50) mentioned in [3].
[9] A method for identifying a PPR protein containing one or more (preferably 2 to 30) PPR motifs ($M_n$) defined in [1] that can bind to a target DNA base or target DNA having a specific base sequence, wherein:
the PPR protein is identified by determining presence or absence of a combination of the three amino acids of No. 1 A.A., No. 4 A.A., and No. "ii" (−2) A.A. corresponding to the target DNA base or a specific base constituting the target DNA on the basis of any one of the definitions (1-1) to (1-9) mentioned in [2], and (2-1) to (2-50) mentioned in [3]. [10] A method for controlling a function of DNA, which uses the protein according to [1].
[11] A complex consisting of a region comprising the protein according to [1], and a functional region bound together.
[12] The complex according to [11], wherein the functional region is fused to the protein according to [1] on the C-terminus side of the protein.
[13] The complex according to [11] or [12], wherein the functional region is a DNA-cleaving enzyme, or a nuclease domain thereof, or a transcription control domain, and the complex functions as a target sequence-specific DNA-cleaving enzyme or transcription control factor.
[14] The complex according to [13] wherein the DNA-cleaving enzyme is the nuclease domain of FokI (SEQ ID NO: 6).
[15] A method for modifying a genetic substance of a cell comprising the following steps:
preparing a cell containing a DNA having a target sequence; and
introducing the complex according to [11] into the cell so that the region of the complex consisting of the protein binds to the DNA having a target sequence, and therefore the functional region modifies the DNA having a target sequence.
[16] A method for identifying, recognizing, or targeting a DNA base or DNA having a specific base sequence by using a PPR protein containing one or more PPR motifs.
[17] The method according to [16], wherein the protein contains one or more PPR motifs in which three amino acids among the amino acids constituting the motif constitute a specific combination of amino acids.

[18] The method according to [16] or [17], wherein the protein contains one or more PPR motifs ($M_n$) defined in [1].

Effect of the Invention

According to the present invention, a PPR motif that can binds to a target DNA base, and a protein containing it can be provided. By arranging two or more PPR motifs, a protein that can binds to a target DNA having an arbitrary sequence or length can be provided.

According to the present invention, a target DNA of an arbitrary PPR protein can be predicted and identified, and conversely, a PPR protein that binds to an arbitrary DNA can be predicted and identified. Prediction of such a target DNA sequence clarifies the genetic identity thereof, and increases possibility of use thereof. Furthermore, according to the present invention, functionalities of homologous genes of a gene of an industrially useful PPR protein showing amino acid polymorphism at a high level can be determined on the basis of difference of the target DNA base sequences thereof.

Furthermore, according to the present invention, a novel DNA-cleaving enzyme using a PPR motif can also be provided. That is, by linking a protein as a functional region with the PPR motif or PPR protein provided by the present invention, a complex containing a protein having a binding activity for a specific nucleic acid sequence, and a protein having a specific functionality can be prepared.

The functional region usable in the present invention is one that can impart, among various functions, a function for any one of cleavage, transcription, replication, restoration, synthesis, modification, etc. of DNA. By choosing the sequence of the PPR motifs, which is the characteristic of the present invention, to determine a base sequence of DNA as a target, almost all DNA sequences can be used as a target, and genome edition using a function of the functional region such as those for cleavage, transcription, replication, restoration, synthesis, modification, etc. of DNA can be realized with such a target.

For example, when the functional region has a function for cleaving DNA, a complex comprising a PPR protein part prepared according to the present invention and a DNA-cleaving region linked together is provided. Such a complex can function as an artificial DNA-cleaving enzyme, which recognizes a base sequence of DNA as a target with the PPR protein part, and then cleaves DNA with the region for cleaving DNA. When the functional region has a transcription control function, a complex comprising a PPR protein part prepared according to the present invention and a transcription control region for DNA linked together is provided. Such a complex can function as an artificial transcription control factor, which recognizes a base sequence of DNA as a target with the PPR protein part, and then promotes transcription of the target DNA.

The present invention can further be utilized for a method for delivering the aforementioned complex in a living body so that the complex functions in the living body, and preparation of transformants utilizing a nucleic acid sequence (DNA and RNA) encoding a protein obtained according to the present invention, as well as specific modification, control, and impartation of a function in various situations in organisms (cells, tissues, and individuals).

BRIEF DESCRIPTION OF THE DRAWINGS

FIG. 1 shows conserved sequences and amino acid numbers of the PPR motif.

FIG. 2 summarizes the outlines of the structures of Arabidopsis thaliana p63 (amino acid sequence of SEQ ID NO: 1), the GUN1 protein of Arabidopsis thaliana (amino acid sequence of SEQ ID NO: 2), pTac2 of Arabidopsis thaliana (amino acid sequence of SEQ ID NO: 3), DG1 (amino acid sequences of SEQ ID NO: 4), and GRP23 of Arabidopsis thaliana (amino acid sequence of SEQ ID NO: 5), which are DNA-binding type PPR proteins that function in DNA metabolism, and the outline of the assay system for demonstrating that they bind to DNA.

FIG. 3 summarizes the amino acid frequencies of the amino acids at the three positions bearing the nucleic acid recognition codes in the PPR motif (No. 1 A.A., No. 4 A.A., and No. "ii" (−2) A.A.) for the PPR motifs of the PPR proteins (SEQ ID NOS: 1 to 5), for which DNA binding property was suggested, and known RNA-binding type motifs.

FIG. 4-1 shows the positions of the PPR motifs included in the inside of the proteins, and the positions of the three amino acids bearing the nucleic acid recognition codes (No. 1 A.A., No. 4 A.A., and No. "ii" (−2) A.A.) in the PPR motifs for each of (A) Arabidopsis thaliana p63 (amino acid sequence of SEQ ID NO: 1) and (B) the GUN1 protein of Arabidopsis thaliana (amino acid sequence of SEQ ID NO: 2.

FIG. 4-2 shows the positions of the PPR motifs included in the inside of the proteins, and the positions of the three amino acids bearing the nucleic acid recognition codes (No. 1 A.A., No. 4 A.A., and No. "ii" (−2) A.A.) in the PPR motifs for each of (C) pTac2 of Arabidopsis thaliana (amino acid sequence of SEQ ID NO: 3), and (D) DG1 (amino acid sequence of SEQ ID NO: 4).

FIG. 4-3 shows the positions of the PPR motifs included in the inside of the proteins, and the positions of the three amino acids bearing the nucleic acid recognition codes (No. 1 A.A., No. 4 A.A., and No. "ii" (−2) A.A.) in the PPR motifs for (E) GRP23 of Arabidopsis thaliana (amino acid sequence of SEQ ID NO: 5).

FIG. 5 shows the evaluation of the sequence-specific DNA-binding abilities of the PPR molecules. Artificial transcription factors were prepared by fusing each of three kinds of DNA-binding type (regarded so) PPR molecules with VP64, which is a transcription activation domain, and whether they could activate a luciferase reporter having each target sequence was examined in a human cultured cell.

FIG. 6 shows comparison of the luciferase activities observed by cointroduction of pTac2-VP64 or GUN1-VP64 with pminCMV-luc2 as a negative control, or a reporter vector comprising 4 or 8 target sequences. As a result, there was observed a tendency that the activity increased with increase of the target sequence for the both molecules, and thus it was verified that these PPR-VP64 molecules specifically bound to each target sequence to function as a site-specific transcription activator.

MODES FOR CARRYING OUT THE INVENTION

[PPR Motif and PPR Protein]

The "PPR motif" referred to in the present invention means a polypeptide constituted with 30 to 38 amino acids and having an amino acid sequence that shows, when the amino acid sequence is analyzed with a protein domain search program on the web (for example, Pfam, Prosite, Uniprot, etc.), an E value not larger than a predetermined value (desirably E-03) obtained at PF01535 in the case of Pfam (http://pfam.sanger.ac.uk/), or PS51375 in the case of Prosite (http://www.expasy.org/prosite/), unless otherwise indicated. The PPR motifs in various proteins are also defined in the Uniprot database (http://www.uniprot.org).

Although the amino acid sequence of the PPR motif is not highly conserved in the PPR motif of the present invention, such a secondary structure of helix, loop, helix, and loop as shown by the following formula is conserved well.

[Formula 2]

$$(\text{Helix A})\text{-}X\text{-}(\text{Helix B})\text{-}L \qquad \text{(Formula 1)}$$

The position numbers of the amino acids constituting the PPR motif defined in the present invention are according to those defined in a paper of the inventors of the present invention (Kobayashi K, et al., Nucleic Acids Res., 40, 2712-2723 (2012)). That is, the position numbers of the amino acids constituting the PPR motif defined in the present invention are substantially the same as the amino acid numbers defined for PF01535 in Pfam, but correspond to numbers obtained by subtracting 2 from the amino acid numbers defined for PS51375 in Prosite (for example, position 1 according to the present invention is position 3 of PS51375), and also correspond to numbers obtained by subtracting 2 from the amino acid numbers of the PPR motif defined in Uniprot.

Figure 1A:
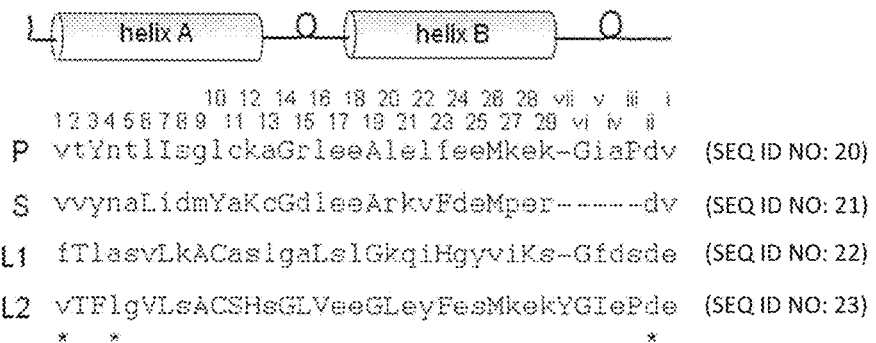
FIG. 1A shows the amino acids constituting the PPR motif defined in the present invention, and the amino acid numbers thereof (the amino acid sequences P, S, L1, and L2 correspond to SEQ ID NO: 20, SEQ ID NO: 21, SEQ ID NO: 22, and SEQ ID NO: 23, respectively).
Figure 1B:
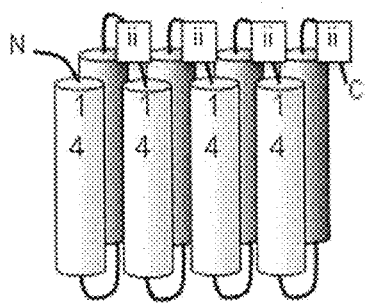
FIG. 1B shows positions of three amino acids (No. 1 A.A., No. 4 A.A., and No. "ii" (−2) A.A.) that control binding base selectivity in the predicted structure.
Figure 1C:
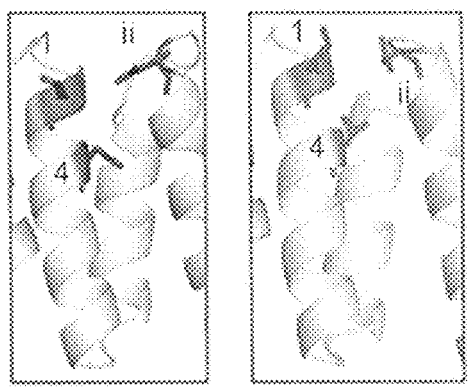
FIG. 1C shows two examples of the structure of the PPR motif, and the positions of the amino acids on the predicted structure for each case. No. 1 A.A., No. 4 A.A., and No. "ii" (−2) A.A. are indicated with sticks of magenta color (dark gray in the case of monochratic display) in the conformational diagrams of the protein.

More precisely, in the present invention, the No. 1 amino acid is the first amino acid from which Helix A shown in the formula 1 starts. The No. 4 amino acid is the fourth amino acid counted from the No. 1 amino acid. As for "ii" (−2)nd amino acid, when a next PPR motif ($M_{n+1}$) contiguously exists on the C-terminus side of the PPR motif ($M_n$) (when there is no amino acid insertion between the PPR motifs, as in the cases of, for example, Motif Nos. 1, 2, 3, 4, 6 and 7 in FIG. 4-1 (A)), the −2nd amino acid counted from the end (C-terminus side) of the amino acids constituting the PPR motif ($M_n$) is referred to as No. "ii" (−2) amino acid;

when a non-PPR motif (part that is not the PPR motif) consisting of 1 to 20 amino acids exists between the PPR motif ($M_n$) and the next PPR motif ($M_{n+1}$) on the C-terminus side (as in the cases of, for example, Motif Nos. 5 and 8 in FIG. 4-1 (A), and Motif Nos. 1, 2, 7 and 8 in FIG. 4-3 (D)), the amino acid locating upstream of the first amino acid of the next PPR motif ($M_{n+1}$) by 2 positions, i.e., the −2nd amino acid, is referred to as No. "ii" (−2) amino acid (refer to FIG. 1); or when any next PPR motif ($M_{n+1}$) does not exist on the C-terminus side of the PPR motif ($M_n$) (as in the cases of, for example, Motif No. 9 in FIG. 4-1 (A), and Motif No. 11 in FIG. 4-1 (B)), or 21 or more amino acids constituting a non-PPR motif exist between the PPR motif ($M_n$) and the next PPR motif ($M_{n+1}$) on the C-terminus side, the 2nd amino acid counted from the end (C-terminus side) of the amino acids constituting the PPR motif ($M_n$) is referred to as No. "ii" (−2) amino acid.

The "PPR protein" referred to in the present invention means a PPR protein having two or more of the aforementioned PPR motifs, unless otherwise indicated. The term "protein" used in this specification means any substance consisting of a polypeptide (chain consisting of two or more amino acids bound through peptide bonds), and also includes those consisting of a comparatively low molecular weight polypeptide, unless otherwise indicated. The "amino acid" referred to in the present invention means a usual amino acid molecule, as well as an amino acid residue constituting a peptide chain. Which the term means will be apparent to those skilled in the art from the context.

Many PPR proteins exist in plants, and 500 proteins and about 5000 motifs can be found in *Arabidopsis thaliana*. PPR motifs and PPR proteins of various amino acid sequences also exist in many land plants such as rice, poplar, and selaginella. It is known that some PPR proteins are important factors for obtaining F1 seeds for hybrid vigor as fertility restoration factors that are involved in formation of pollen (male gamete). It has been clarified that some PPR proteins are involved in speciation, similarly in fertility restoration. It has also been clarified that almost all the PPR proteins act on RNA in mitochondria or chloroplasts.

It is known that, in animals, anomaly of the PPR protein identified as LRPPRC causes Leigh syndrom French Canadian (LSFC, Leigh's syndrome, subacute necrotizing encephalomyelopathy).

The term "selective" used for a property of a PPR motif for binding with a DNA base in the present invention means that a binding activity for any one base among the DNA bases is higher than binding activities for the other bases, unless otherwise indicates. Those skilled in the art can confirm this selectivity by planning an experiment, or it can also be obtained by calculation as described in the examples mentioned in this specification.

The DNA base referred to in the present invention means a base of deoxyribonucleotide constituting DNA, and specifically, it means any of adenine (A), guanine (G), cytosine (C), and thymine (T), unless otherwise indicated. Although the PPR protein may have selectivity to a base in DNA, it does not bind to a nucleic acid monomer.

Although search methods for conserved amino acid sequence as the PPR motif had been established before the present invention was accomplished, any rule concerning selective binding with DNA base had not been discovered at all.

[Findings Provided by the Present Invention]

The following findings are provided by the present invention.

(I) Information about Positions of Amino Acids Important for Selective Binding

Specifically, under the following definitions:
the first amino acid of Helix A of the PPR motif is referred to as No. 1 amino acid (No. 1 A.A.), the fourth amino acid as No. 4 amino acid (No. 4 A.A.), and when a next PPR motif ($M_{n+1}$) contiguously exists on the C-terminus side of the PPR motif ($M_n$) (when there is no amino acid insertion between the PPR motifs), the −2nd amino acid counted from the end (C-terminus side) of the amino acids constituting the PPR motif ($M_n$);

when a non-PPR motif consisting of 1 to 20 amino acids exist between the PPR motif ($M_n$) and the next PPR motif ($M_{n+1}$) on the C-terminus side, the amino acid locating upstream of the first amino acid of the next PPR motif ($M_{n+1}$) by 2 positions, i.e., the −2nd amino acid; or when any next PPR motif ($M_{n+1}$) does not exist on the C-terminus side of the PPR motif ($M_n$), or 21 or more amino acids constituting a non-PPR motif exist between the PPR motif ($M_n$) and the next PPR motif ($M_{n+1}$) on the C-terminus side, the 2nd amino acid counted from the end (C-terminus side) of the amino acids constituting the PPR motif ($M_n$)

is referred to as No. "ii" (−2) amino acid (No. "ii" (−2) A.A.), combination of the three amino acids, the first and fourth amino acids of the helix (Helix A), No. 1 and No. 4 amino acids, and No. "ii" (−2) A.A. defined above (No. 1 A.A., No. 4 A.A. and No. "ii" (−2) A.A.) is important for selective binding to a DNA base, and to what kind of DNA base the motif binds can be determined on the basis of the combination.

The present invention is based on the findings concerning the combination of the three amino acids, No. 1 A.A., No. 4 A.A., and No. "ii" (−2) A.A., found by the inventors of the present invention. Specifically:

(1-1) when No. 4 A.A. is glycine (G), No. 1 A.A. may be an arbitrary amino acid, No. "ii" (−2) A.A. is aspartic acid (D), asparagine (N), or serine (S), and the combination of No. 1 A.A., and No. "ii" (−2) A.A. may be, for example:

a combination of an arbitrary amino acid and aspartic acid (D) (*GD), preferably a combination of glutamic acid (E) and aspartic acid (D) (EGD), a combination of an arbitrary amino acid and asparagine (N) (*GN), preferably a combination of glutamic acid (E) and asparagine (N) (EGN), or a combination of an arbitrary amino acid and serine (S) (*GS);

(1-2) when No. 4 A.A. is isoleucine (I), each of No. 1 A.A. and No. "ii" (−2) A.A. may be an arbitrary amino acid, and the combination of No. 1 A.A., and No. "ii" (−2) A.A. may be, for example:

a combination of an arbitrary amino acid and asparagine (N) (*IN);

(1-3) when No. 4 A.A. is leucine (L), each of No. 1 A.A. and No. "ii" (−2) A.A. may be an arbitrary amino acid, and the combination of No. 1 A.A., and No. "ii" (−2) A.A. may be, for example:

a combination of an arbitrary amino acid and aspartic acid (D) (*LD), or a combination of an arbitrary amino acid and lysine (K) (*LK);

(1-4) when No. 4 A.A. is methionine (M), each of No. 1 A.A. and No. "ii" (−2) A.A. may be an arbitrary amino acid, and the combination of No. 1 A.A., and No. "ii" (−2) A.A. may be, for example:

a combination of an arbitrary amino acid and aspartic acid (D) (*MD), or a combination of isoleucine (I) and aspartic acid (D) (IMD);

(1-5) when No. 4 A.A. is asparagine (N), each of No. 1 A.A. and No. "ii" (−2) A.A. may be an arbitrary amino acid, and the combination of No. 1 A.A., and No. "ii" (−2) A.A. may be, for example:

a combination of an arbitrary amino acid and aspartic acid (D) (*ND), a combination of any one of phenylalanine (F), glycine (G), isoleucine (I), threonine (T), valine (V) and tyrosines (Y), and aspartic acid (D) (FND, GND, IND, TND, VND, or YND), a combination of an arbitrary amino acid and asparagine (N) (*NN), a combination of any one of isoleucine (I), serine (S) and valine (V), and asparagine (N) (INN, SNN or VNN)

a combination of an arbitrary amino acid and serine (S) (*NS), a combination of valine (V) and serine (S) (VNS), a combination of an arbitrary amino acid and threonine (T) (*NT), a combination of valine (V) and threonine (T) (VNT), a combination of an arbitrary amino acid and tryptophan (W) (*NW), or a combination of isoleucine (I) and tryptophan (W) (INW);

(1-6) when No. 4 A.A. is proline (P), each of No. 1 A.A. and No. "ii" (−2) A.A. may be an arbitrary amino acid, and the combination of No. 1 A.A., and No. "ii" (−2) A.A. may be, for example:

a combination of an arbitrary amino acid and aspartic acid (D) (*PD), a combination of phenylalanine (F) and aspartic acid (D) (FPD), or a combination of tyrosine (Y) and aspartic acid (D) (YPD);

(1-7) when No. 4 A.A. is serine (S), each of No. 1 A.A. and No. "ii" (−2) A.A. may be an arbitrary amino acid, and the combination of No. 1 A.A., and No. "ii" (−2) A.A. may be, for example:

a combination of an arbitrary amino acid and asparagine (N) (*SN), a combination of phenylalanine (F) and asparagine (N) (FSN), or a combination of valine (V) and asparagine (N) (VSN);

(1-8) when No. 4 A.A. is threonine (T), each of No. 1 A.A. and No. "ii" (−2) A.A. may be an arbitrary amino acid, and the combination of No. 1 A.A., and No. "ii" (−2) A.A. may be, for example:

a combination of an arbitrary amino acid and aspartic acid (D) (*TD), a combination of valine (V) and aspartic acid (D) (VTD), a combination of an arbitrary amino acid and asparagine (N) (*TN), a combination of phenylalanine (F) and asparagine (N) (FTN), a combination of isoleucine (I) and asparagine (N) (ITN), or a combination of valine (V) and asparagine (N) (VTN); and (1-9) when No. 4 A.A. is valine (V), each of No. 1 A.A. and No. "ii" (−2) A.A. may be an arbitrary amino acid, and the combination of No. 1 A.A., and No. "ii" (−2) A.A. may be, for example:

a combination of isoleucine (I) and aspartic acid (D) (IVD), a combination of an arbitrary amino acid and glycine (G) (*VG), or a combination of an arbitrary amino acid and threonine (T) (*VT).

(II) Information about Correspondence of Combination of Three Amino Acids of No. 1 A.A., No. 4 A.A., and No. "ii" (−2) A.A., and DNA Base The protein is a protein determined on the basis of, specifically, the following definitions, and having a selective DNA base-binding property:

(2-1) when the three amino acids, No. 1 A.A., No. 4 A.A., and No. "ii" (−2) A.A., are an arbitrary amino acid, glycine, and aspartic acid, respectively, the PPR motif selectively binds to G;

(2-2) when the three amino acids, No. 1 A.A., No. 4 A.A., and No. "ii" (−2) A.A., are glutamic acid, glycine, and aspartic acid, respectively, the PPR motif selectively binds to G;

(2-3) when the three amino acids, No. 1 A.A., No. 4 A.A., and No. "ii" (−2) A.A., are an arbitrary amino acid, glycine, and asparagine, respectively, the PPR motif selectively binds to A;

(2-4) when the three amino acids, No. 1 A.A., No. 4 A.A., and No. "ii" (−2) A.A., are glutamic acid, glycine, and asparagine, respectively, the PPR motif selectively binds to A;

(2-5) when the three amino acids, No. 1 A.A., No. 4 A.A., and No. "ii" (−2) A.A., are an arbitrary amino acid, glycine, and serine, respectively, the PPR motif selectively binds to A, and next binds to C;

(2-6) when the three amino acids, No. 1 A.A., No. 4 A.A., and No. "ii" (−2) A.A., are an arbitrary amino acid, isoleucine, and an arbitrary amino acid, respectively, the PPR motif selectively binds to T and C;

(2-7) when the three amino acids, No. 1 A.A., No. 4 A.A., and No. "ii" (−2) A.A., are an arbitrary amino acid, isoleucine, and asparagine, respectively, the PPR motif selectively binds to T, and next binds to C;

(2-8) when the three amino acids, No. 1 A.A., No. 4 A.A., and No. "ii" (−2) A.A., are an arbitrary amino acid, leucine, and an arbitrary amino acid, respectively, the PPR motif selectively binds to T and C;

(2-9) when the three amino acids, No. 1 A.A., No. 4 A.A., and No. "ii" (−2) A.A., are an arbitrary amino acid, leucine, and aspartic acid, respectively, the PPR motif selectively binds to C;

(2-10) when the three amino acids, No. 1 A.A., No. 4 A.A., and No. "ii" (−2) A.A., are an arbitrary amino acid, leucine, and lysine, respectively, the PPR motif selectively binds to T;

(2-11) when the three amino acids, No. 1 A.A., No. 4 A.A., and No. "ii" (−2) A.A., are an arbitrary amino acid, methionine, and an arbitrary amino acid, respectively, the PPR motif selectively binds to T;

(2-12) when the three amino acids, No. 1 A.A., No. 4 A.A., and No. "ii" (−2) A.A., are an arbitrary amino acid, methionine, and aspartic acid, respectively, the PPR motif selectively binds to T;

(2-13) when the three amino acids, No. 1 A.A., No. 4 A.A., and No. "ii" (−2) A.A., are isoleucine, methionine, and aspartic acid, respectively, the PPR motif selectively binds to T, and next binds to C;

(2-14) when the three amino acids, No. 1 A.A., No. 4 A.A., and No. "ii" (−2) A.A., are an arbitrary amino acid, asparagine, and an arbitrary amino acid, respectively, the PPR motif selectively binds to C and T;

(2-15) when the three amino acids, No. 1 A.A., No. 4 A.A., and No. "ii" (−2) A.A., are an arbitrary amino acid, asparagine, and aspartic acid, respectively, the PPR motif selectively binds to T;

(2-16) when the three amino acids, No. 1 A.A., No. 4 A.A., and No. "ii" (−2) A.A., are phenylalanine, asparagine, and aspartic acid, respectively, the PPR motif selectively binds to T;

(2-17) when the three amino acids, No. 1 A.A., No. 4 A.A., and No. "ii" (−2) A.A., are glycine, asparagine, and aspartic acid, respectively, the PPR motif selectively binds to T;

(2-18) when the three amino acids, No. 1 A.A., No. 4 A.A., and No. "ii" (−2) A.A., are isoleucine, asparagine, and aspartic acid, respectively, the PPR motif selectively binds to T;

(2-19) when the three amino acids, No. 1 A.A., No. 4 A.A., and No. "ii" (−2) A.A., are threonine, asparagine, and aspartic acid, respectively, the PPR motif selectively binds to T;

(2-20) when the three amino acids, No. 1 A.A., No. 4 A.A., and No. "ii" (−2) A.A. are valine, asparagine, and aspartic acid, respectively, the PPR motif selectively binds to T, and next binds to C;

(2-21) when the three amino acids, No. 1 A.A., No. 4 A.A., and No. "ii" (−2) A.A. are tyrosine, asparagine, and aspartic acid, respectively, the PPR motif selectively binds to T, and next binds to C;

(2-22) when the three amino acids, No. 1 A.A., No. 4 A.A., and No. "ii" (−2) A.A., are an arbitrary amino acid, asparagine, and asparagine, respectively, the PPR motif selectively binds to C;

(2-23) when the three amino acids, No. 1 A.A., No. 4 A.A., and No. "ii" (−2) A.A., are isoleucine, asparagine, and asparagine, respectively, the PPR motif selectively binds to C;

(2-24) when the three amino acids, No. 1 A.A., No. 4 A.A., and No. "ii" (−2) A.A., are serine, asparagine, and asparagine, respectively, the PPR motif selectively binds to C;

(2-25) when the three amino acids, No. 1 A.A., No. 4 A.A., and No. "ii" (−2) A.A., are valine, asparagine, and asparagine, respectively, the PPR motif selectively binds to C;

(2-26) when the three amino acids, No. 1 A.A., No. 4 A.A., and No. "ii" (−2) A.A., are an arbitrary amino acid, asparagine, and serine, respectively, the PPR motif selectively binds to C;

(2-27) when the three amino acids, No. 1 A.A., No. 4 A.A., and No. "ii" (−2) A.A., are valine, asparagine, and serine, respectively, the PPR motif selectively binds to C;

(2-28) when the three amino acids, No. 1 A.A., No. 4 A.A., and No. "ii" (−2) A.A., are an arbitrary amino acid, asparagine, and threonine, respectively, the PPR motif selectively binds to C;

(2-29) when the three amino acids, No. 1 A.A., No. 4 A.A., and No. "ii" (−2) A.A., are valine, asparagine, and threonine, respectively, the PPR motif selectively binds to C;

(2-30) when the three amino acids, No. 1 A.A., No. 4 A.A., and No. "ii" (−2) A.A., are an arbitrary amino acid, asparagine, and tryptophan, respectively, the PPR motif selectively binds to C, and next binds to T;

(2-31) when the three amino acids, No. 1 A.A., No. 4 A.A., and No. "ii" (−2) A.A., are isoleucine, asparagine, and tryptophan, respectively, the PPR motif selectively binds to T, and next binds to C;

(2-32) when the three amino acids, No. 1 A.A., No. 4 A.A., and No. "ii" (−2) A.A., are an arbitrary amino acid, proline, and an arbitrary amino acid, respectively, the PPR motif selectively binds to T;

(2-33) when the three amino acids, No. 1 A.A., No. 4 A.A., and No. "ii" (−2) A.A., are an arbitrary amino acid, proline, and aspartic acid, respectively, the PPR motif selectively binds to T;

(2-34) when the three amino acids, No. 1 A.A., No. 4 A.A., and No. "ii" (−2) A.A., are phenylalanine, proline, and aspartic acid, respectively, the PPR motif selectively binds to T;

(2-35) when the three amino acids, No. 1 A.A., No. 4 A.A., and No. "ii" (−2) A.A., are tyrosine, proline, and aspartic acid, respectively, the PPR motif selectively binds to T;
(2-36) when the three amino acids, No. 1 A.A., No. 4 A.A., and No. "ii" (−2) A.A., are an arbitrary amino acid, serine, and an arbitrary amino acid, respectively, the PPR motif selectively binds to A and G;
(2-37) when the three amino acids, No. 1 A.A., No. 4 A.A., and No. "ii" (−2) A.A., are an arbitrary amino acid, serine, and asparagine, respectively, the PPR motif selectively binds to A;
(2-38) when the three amino acids, No. 1 A.A., No. 4 A.A., and No. "ii" (−2) A.A., are phenylalanine, serine, and asparagine, respectively, the PPR motif selectively binds to A;
(2-39) when the three amino acids, No. 1 A.A., No. 4 A.A., and No. "ii" (−2) A.A., are valine, serine, and asparagine, respectively, the PPR motif selectively binds to A;
(2-40) when the three amino acids, No. 1 A.A., No. 4 A.A., and No. "ii" (−2) A.A., are an arbitrary amino acid, threonine, and an arbitrary amino acid, respectively, the PPR motif. selectively binds to A and G;
(2-41) when the three amino acids, No. 1 A.A., No. 4 A.A., and No. "ii" (−2) A.A., are an arbitrary amino acid, threonine, and aspartic acid, respectively, the PPR motif selectively binds to G;
(2-42) when the three amino acids, No. 1 A.A., No. 4 A.A., and No. "ii" (−2) A.A., are valine, threonine, and aspartic acid, respectively, the PPR motif selectively binds to G;
(2-43) when the three amino acids, No. 1 A.A., No. 4 A.A., and No. "ii" (−2) A.A., are an arbitrary amino acid, threonine, and asparagine, respectively, the PPR motif selectively binds to A;
(2-44) when the three amino acids, No. 1 A.A., No. 4 A.A., and No. "ii" (−2) A.A., are phenylalanine, threonine, and asparagine, respectively, the PPR motif selectively binds to A;
(2-45) when the three amino acids, No. 1 A.A., No. 4 A.A., and No. "ii" (−2) A.A., are isoleucine, threonine, and asparagine, respectively, the PPR motif selectively binds to A;
(2-46) when the three amino acids, No. 1 A.A., No. 4 A.A., and No. "ii" (−2) A.A., are valine, threonine, and asparagine, respectively, the PPR motif selectively binds to A;
(2-47) when the three amino acids, No. 1 A.A., No. 4 A.A., and No. "ii" (−2) A.A., are an arbitrary amino acid, valine, and an arbitrary amino acid, respectively, the PPR motif binds with A, C, and T, but does not bind to G;
(2-48) when the three amino acids, No. 1 A.A., No. 4 A.A., and No. "ii" (−2) A.A., are isoleucine, valine, and aspartic acid, respectively, the PPR motif selectively binds to C, and next binds to A;
(2-49) when the three amino acids, No. 1 A.A., No. 4 A.A., and No. "ii" (−2) A.A., are an arbitrary amino acid, valine, and glycine, respectively, the PPR motif selectively binds to C; and
(2-50) when the three amino acids, No. 1 A.A., No. 4 A.A., and No. "ii" (−2) A.A., are an arbitrary amino acid, valine, and threonine, respectively, the PPR motif selectively binds to T.

Combination of amino acids of specific positions and binding property with a DNA base can be confirmed by experiments. Experiments for such purposes include preparation of a PPR motif or a protein containing two or more PPR motifs, preparation of a substrate DNA, and binding property test (for example, gel shift assay). These experiments are well known to those skilled in the art, and as for more specific procedures and conditions, for example, Patent document 2 can be referred to.

[Use of PPR Motif and PPR Protein]

Identification and Design

One PPR motif recognizes a specific one kind of base of DNA, and two or more contiguous PPR motifs can recognize continuous bases in a DNA sequence. Further, according to the present invention, by appropriately choosing amino acids at specific positions, PPR motifs selective for each of A, T, G, and C can be chosen or designed, and a protein containing an appropriate continuation of such PPR motifs can recognize a corresponding specific sequence. Therefore, according to the present invention, a naturally occurring PPR protein that selectively binds to DNA having a specific base sequence can be predicted or identified, or conversely, DNA as a target of binding of a PPR protein can be predicted and identified. Prediction or identification of such a target is useful for clarifying genetic identity of the target, and is also useful from a viewpoint that such prediction or identification may expand applicability of the target.

Furthermore, according to the present invention, a PPR motif that can selectively bind to a desired DNA base, and a protein having two or more PPR motifs that can bind to a desired DNA in a sequence-specific manner can be designed. In such design, as for the part other than the amino acids at the important positions in the PPR motif, sequence information on PPR motifs of naturally occurring type in DNA-binding type PPR proteins such as those of SEQ ID NOS: 1 to 5 can be referred to. Further, the motif or protein may also be designed by using a motif or protein of naturally occurring type as a whole, and replacing only the amino acids of the corresponding positions. Although the number of repetitions of PPR motifs can be appropriately chosen according to a target sequence, it may be, for example, 2 or more, preferably 2 to 30, more preferably 5 to 25, most preferably 9 to 15.

In the designing, amino acids other than those of the combination of the amino acids of No. 1 A.A., No. 4 A.A., and No. "ii" (−2) A.A. may be taken into consideration. For example, selection of the amino acids of No. 8 and No. 12 described in Patent document 2 mentioned above may be important for exhibiting a DNA-binding activity. According to the researches of the inventors of the present invention, the No. 8 amino acid of a certain PPR motif and the No. 12 amino acid of the same PPR motif may cooperate in binding with DNA. The No. 8 amino acid may be a basic amino acid, preferably lysine, or an acidic amino acid, preferably aspartic acid, and the No. 12 amino acid may be a basic amino acid, neutral amino acid, or hydrophobic amino acid.

A designed motif or protein can be prepared by methods well known to those skilled in the art. That is, the present invention provides a PPR motif that selectively binds to a specific DNA base, and a PPR protein that specifically binds to DNA having a specific sequence, in which attention is paid to the combination of the amino acids of No. 1 A.A., No. 4 A.A., and No. "ii" (−2) A.A. Such a motif and protein can be prepared even in a comparatively large amount by methods well known to those skilled in the art, and such methods may comprise determining a nucleic acid sequence encoding a target motif or protein from the amino acid sequence of the target motif or protein, cloning it, and preparing a transformant that produces the target motif or protein.

Preparation of Complex and Use Thereof

The PPR motif or PPR protein provided by the present invention can be made into a complex by binding a functional region. The functional region generally refers to a part having such a function as a specific biological function exerted in a living body or cell, for example, enzymatic function, catalytic function, inhibitory function, promotion function, etc, or a function as a marker. Such a region consists of, for example, a protein, peptide, nucleic acid, physiologically active substance, or drug.

According to the present invention, by binding a functional region to the PPR protein, the target DNA sequence-binding function exerted by the PPR protein, and the function exerted by the functional region can be exhibited in combination. For example, if a protein having a DNA-cleaving function (for example, restriction enzyme such as FoId) or a nuclease domain thereof is used as the functional region, the complex can function as an artificial DNA-cleaving enzyme.

In order to produce such a complex, methods generally available in this technical field can be used, and there are known a method of synthesizing such a complex as one protein molecule, a method of separately synthesizing two or more members of proteins, and then combining them to form a complex, and so forth.

In the case of the method of synthesizing a complex as one protein molecule, for example, a protein complex can be designed so as to comprise a PPR protein and a cleaving enzyme bound to the C-terminus of the PPR protein via an amino acid linker, an expression vector structure for expressing the protein complex can be constructed, and the target complex can be expressed from the structure. As such a preparation method, the method described in Japanese Patent Application No. 2011-242250, and so forth can be used.

For binding the PPR protein and the functional region protein, any binding means known in this technical field may be used, including binding via an amino acid linker, binding utilizing specific affinity such as binding between avidin and biotin, binding utilizing another chemical linker, and so forth.

The functional region usable in the present invention refers to a region that can impart any one of various functions such as those for cleavage, transcription, replication, restoration, synthesis, or modification of DNA, and so forth. By choosing the sequence of the PPR motif to define a DNA base sequence as a target, which is the characteristic of the present invention, substantially any DNA sequence may be used as the target, and with such a target, genome edition utilizing the function of the functional region such as those for cleavage, transcription, replication, restoration, synthesis, or modification of DNA can be realized.

For example, when the function of the functional region is a DNA cleavage function, there is provided a complex comprising a PPR protein part prepared according to the present invention and a DNA cleavage region bound together. Such a complex can function as an artificial DNA-cleaving enzyme that recognizes a base sequence of DNA as a target by the PPR protein part, and then cleaves DNA by the DNA cleavage region.

An example of the functional region having a cleavage function usable for the present invention is a deoxyribonuclease (DNase), which functions as an endodeoxyribonuclease. As such a DNase, for example, endodeoxyribonucleases such as DNase A (e.g., bovine pancreatic ribonuclease A, PDB 2AAS), DNase H and DNase I, restriction enzymes derived from various bacteria (for example, FokI (SEQ ID NO: 6) etc.) and nuclease domains thereof can be used. Such a complex comprising a PPR protein and a functional region does not exist in the nature, and is novel.

When the function of the functional region is a transcription control function, there is provided a complex comprising a PPR protein part prepared according to the present invention and a DNA transcription control region bound together. Such a complex can function as an artificial transcription control factor, which recognizes a base sequence of DNA as a target by the PPR protein part, and then controls transcription of the target DNA.

The functional region having a transcription control function usable for the present invention may be a domain that activates transcription, or may be a domain that suppresses transcription. Examples of the transcription control domain include VP16, VP64, TA2, STAT-6, and p65. Such a complex comprising a PPR protein and a transcription control domain does not exist in the nature, and is novel.

Further, the complex obtainable according to the present invention may deliver a functional region in a living body or cell in a DNA sequence-specific manner, and allow it to function. It thereby makes it possible to perform modification or disruption in a DNA sequence-specific manner in a living body or cell, like protein complexes utilizing a zinc finger protein (Non-patent documents 1 and 2 mentioned above) or TAL effecter (Non-patent document 3 and Patent document 1 mentioned above), and thus it becomes possible to impart a novel function, i.e., function for cleavage of DNA and genome edition utilizing that function. Specifically, with a PPR protein comprising two or more PPR motifs that can bind with a specific base linked together, a specific DNA sequence can be recognized. Then, genome edition of the recognized DNA region can be realized by the functional region bound to the PPR protein using the function of the functional region.

Furthermore, by binding a drug to the PPR protein that binds to a DNA sequence in a DNA sequence-specific manner, the drug may be delivered to the neighborhood of the DNA sequence as the target. Therefore, the present invention provides a method for DNA sequence-specific delivery of a functional substance.

It has been clarified that the PPR protein used as a material in the present invention works to specify an edition position for DNA edition, and such a PPR motif having specific amino acids arranged at the positions of the residues of No. 1 A.A., No. 4 A.A., and No. "ii" (−2) A.A. recognizes a specific base on DNA, and then exhibits the DNA-binding activity thereof. On the basis of such a characteristic, a PPR protein of this type that has specific amino acids arranged at the positions of the residues of No. 1 A.A., No. 4 A.A., and No. "ii" (−2) A.A. can be expected to recognize a base on DNA specific to each PPR protein, and as a result, introduce base polymorphism, or to be used in a treatment of a disease or condition resulting from a base polymorphism, and in addition, it is considered that the combination of such a PPR protein with such another functional region as mentioned above contribute to modification or improvement of functions for realizing cleavage of DNA for genome edition.

Moreover, an exogenous DNA-cleaving enzyme can be fused to the C-terminus of the PPR protein. Alternatively, by improving binding DNA base selectivity of the PPR motif on the N-terminus side, a DNA sequence-specific DNA-cleaving enzyme can also be constituted. Moreover, such a complex to which a marker part such as GFP is bound can also be used for visualization of a desired DNA in vivo.

together with the information of the Uniprot database (http://www.uniprot.org/). The PPR motifs contained in the five kinds of PPR proteins of *Arabidopsis thaliana* (SEQ ID NOS: 1 to 5) used for the experiment, and the amino acid numbers thereof are shown in FIG. 3.

Specifically, amino acid frequencies for the amino acids at the three positions (No. 1 A.A., No. 4 A.A., and No. "ii" (−2) A.A.) responsible for the nucleic acid recognition codes in the PPR motifs considered to be important at the time of targeting RNA in the aforementioned p63 protein (SEQ ID NO: 1), GUN1 protein (SEQ ID NO: 2), pTac2 protein (SEQ ID NO: 3), DG1 protein (SEQ ID NO: 4), and GRP23 protein (SEQ ID NO: 5) were compared with those of RNA-binding type motifs.

The p63 protein of *Arabidopsis thaliana* (SEQ ID NO: 1) has 9 PPR motifs, and the positions of the residues of No. 1 A.A., No. 4 A.A., and No. "ii" (−2) A.A. in the amino acid sequence are as summarized in the following table and FIG. 3.

TABLE 1

| | $A_1$ | $A_4$ | $L_{ii}$ | Code (1, 4, ii) | Base to be bound (ratio) | | | |
|---|---|---|---|---|---|---|---|---|
| | | | | | A | C | G | T |
| PPR motif 1 | 230, V | 233, R | 263, S | *R* | 0.25 | 0.07 | 0.06 | 0.62 |
| PPR motif 2 | 265, F | 268, D | 297, S | *D* | 0.25 | 0.24 | 0.23 | 0.29 |
| PPR motif 3 | 299, L | 302, K | 332, D | *KD | 0.20 | 0.18 | 0.28 | 0.34 |
| PPR motif 4 | 334, Q | 337, A | 367, N | *AN | 0.45 | 0.18 | 0.05 | 0.32 |
| PPR motif 5 | 369, R | 372, K | 399, Y | *K* | 0.17 | 0.32 | 0.23 | 0.29 |
| PPR motif 6 | 401, E | 404, L | 434, S | *LS | 0.22 | 0.37 | 0.06 | 0.34 |
| PPR motif 7 | 436, S | 439, S | 469, E | *SE | 0.50 | 0.07 | 0.10 | 0.25 |
| PPR motif 8 | 471, T | 474, D | 505, M | *D* | 0.25 | 0.24 | 0.23 | 0.29 |
| PPR motif 9 | 507, N | 510, M | 540, R | *M* | 0.13 | 0.14 | 0.22 | 0.51 |

EXAMPLES

Example 1: Collection of PPR Proteins and Target Sequences Thereof Used for DNA Edition By referring to the information provided in the prior art references (Non-patent documents 11 to 15), structures and functions of the p63 protein (SEQ ID NO: 1), GUN1 protein (SEQ ID NO: 2), pTac2 protein (SEQ ID NO: 3), DG1 protein (SEQ ID NO: 4), and GRP23 protein (SEQ ID NO: 5) were analyzed.

To the PPR motif structures in such proteins, amino acid numbers defined in the present invention were imparted The GUN1 protein of *Arabidopsis thaliana* (SEQ ID NO: 2) has 11 PPR motifs, and the positions of the residues of No. 1 A.A., No. 4 A.A., and No. "ii" (−2) A.A. in the amino acid sequence are as summarized in the following table and FIG. 3.

TABLE 2

| | $A_1$ | $A_4$ | $L_{ii}$ | Code (1, 4, ii) | Base to be bound (ratio) | | | |
|---|---|---|---|---|---|---|---|---|
| | | | | | A | C | G | T |
| PPR motif 1 | 234, K | 237, S | 267, T | *S* | 0.41 | 0.12 | 0.22 | 0.25 |
| PPR motif 2 | 269, Y | 272, S | 302, N | *SN | 0.62 | 0.07 | 0.04 | 0.26 |
| PPR motif 3 | 304, V | 307, N | 338, D | VND | 0.06 | 0.21 | 0.06 | 0.66 |
| PPR motif 4 | 340, I | 343, N | 373, D | IND | 0.14 | 0.24 | 0.12 | 0.50 |
| PPR motif 5 | 375, F | 378, N | 408, N | FNN | 0.24 | 0.21 | 0.24 | 0.31 |
| PPR motif 6 | 410, V | 413, S | 443, D | VSD | 0.33 | 0.24 | 0.23 | 0.20 |
| PPR motif 7 | 445, V | 448, N | 478, D | VND | 0.06 | 0.21 | 0.06 | 0.66 |
| PPR motif 8 | 480, V | 483, N | 513, N | VNN | 0.17 | 0.48 | 0.09 | 0.26 |
| PPR motif 9 | 515, L | 518, S | 548, D | *SD | 0.20 | 0.17 | 0.39 | 0.24 |
| PPR motif 10 | 550, V | 553, S | 583, N | VSN | 0.57 | 0.09 | 0.05 | 0.30 |
| PPR motif 11 | 585, V | 588, N | 620, A | *N* | 0.10 | 0.33 | 0.10 | 0.48 |

The pTac2 protein of *Arabidopsis thaliana* (SEQ ID NO: 3) has 15 PPR motifs, and the positions of the residues of No. 1 A.A., No. 4 A.A., and No. "ii" (−2) A.A. in the amino acid sequence are as summarized in the following table and FIG. 3.

TABLE 3

|  | $A_1$ | $A_4$ | $L_{ii}$ | Code (1, 4, ii) | Base to be bound | | | |
|---|---|---|---|---|---|---|---|---|
|  |  |  |  |  | A | C | G | T |
| PPR motif 1 | 106, N | 109, A | 140, N | *AN | 0.45 | 0.18 | 0.05 | 0.32 |
| PPR motif 2 | 142, H | 145, T | 175, S | *TS | 0.37 | 0.29 | 0.15 | 0.19 |
| PPR motif 3 | 177, F | 180, T | 210, S | *TS | 0.37 | 0.29 | 0.15 | 0.19 |
| PPR motif 4 | 212, L | 215, N | 246, D | LND | 0.08 | 0.15 | 0.23 | 0.54 |
| PPR motif 5 | 248, V | 251, N | 281, D | VND | 0.06 | 0.21 | 0.06 | 0.66 |
| PPR motif 6 | 283, T | 286, S | 316, D | TSD | 0.14 | 0.18 | 0.14 | 0.54 |
| PPR motif 7 | 318, T | 321, N | 351, N | TNN | 0.08 | 0.49 | 0.17 | 0.26 |
| PPR motif 8 | 353, N | 356, S | 386, D | *SD | 0.20 | 0.17 | 0.39 | 0.24 |
| PPR motif 9 | 388, A | 491, N | 421, D | AND | 0.07 | 0.05 | 0.14 | 0.74 |
| PPR motif 10 | 423, E | 426, E | 456, S | B.G. | 0.25 | 0.21 | 0.18 | 0.36 |
| PPR motif 11 | 458, K | 461, T | 491, S | *TS | 0.37 | 0.29 | 0.15 | 0.19 |
| PPR motif 12 | 493, E | 496, H | 526, N | *H* | 0.17 | 0.34 | 0.06 | 0.43 |
| PPR motif 13 | 528, D | 531, N | 561, D | *ND | 0.11 | 0.17 | 0.10 | 0.62 |
| PPR motif 14 | 563, R | 566, E | 596, S | B.G. | 0.25 | 0.21 | 0.18 | 0.36 |
| PPR motif 15 | 598, M | 601, C | 631, I | *C* | 0.55 | 0.10 | 0.21 | 0.14 |

(B.G. means background)

The DG1 protein of *Arabidopsis thaliana* (SEQ ID NO: 4) has 10 PPR motifs, and the positions of the residues of No. 1 A.A., No. 4 A.A., and No. "ii" (−2) A.A. in the amino acid sequence are as summarized in the following table and FIG. 3.

TABLE 4

|  | $A_1$ | $A_4$ | $L_{ii}$ | Code (1, 4, ii) | Base to be bound | | | |
|---|---|---|---|---|---|---|---|---|
|  |  |  |  |  | A | C | G | T |
| PPR motif 1 | 256, F | 259, T | 290, D | *TD | 0.10 | 0.10 | 0.67 | 0.13 |
| PPR motif 2 | 292, A | 295, H | 340, D | *H* | 0.17 | 0.34 | 0.06 | 0.43 |
| PPR motif 3 | 342, V | 345, N | 375, N | VNN | 0.17 | 0.48 | 0.09 | 0.26 |
| PPR motif 4 | 377, A | 380, G | 410, K | *G* | 0.29 | 0.13 | 0.31 | 0.27 |
| PPR motif 5 | 412, I | 415, K | 445, T | *K* | 0.17 | 0.32 | 0.23 | 0.29 |
| PPR motif 6 | 447, S | 450, Y | 481, L | B.G. | 0.25 | 0.21 | 0.18 | 0.36 |
| PPR motif 7 | 483, I | 486, T | 515, N | ITN | 0.79 | 0.06 | 0.05 | 0.10 |
| PPR motif 8 | 517, G | 520, N | 553, N | *NN | 0.12 | 0.44 | 0.13 | 0.30 |
| PPR motif 9 | 555, Y | 558, S | 588, D | YSD | 0.25 | 0.15 | 0.39 | 0.20 |
| PPR motif 10 | 590, T | 593, A | 623, H | *AH | 0.41 | 0.08 | 0.07 | 0.45 |

(B.G. means background)

The GRP23 protein of *Arabidopsis thaliana* (SEQ ID NO: 5) has 11 PPR motifs, and the positions of the residues of No. 1 A.A., No. 4 A.A., and No. "ii" (−2) A.A. in the amino acid sequence are as summarized in the following table and FIG. 3.

TABLE 5

|  | $A_1$ | $A_4$ | $L_{ii}$ | Code (1, 4, ii) | Base to be bound | | | |
|---|---|---|---|---|---|---|---|---|
|  |  |  |  |  | A | C | G | T |
| PPR motif 1 | 181, F | 184, N | 215, N | FNN | 0.24 | 0.21 | 0.24 | 0.31 |
| PPR motif 2 | 217, V | 220, N | 251, S | VNS | 0.07 | 0.61 | 0.05 | 0.27 |
| PPR motif 3 | 253, V | 256, R | 286, D | *RD | 0.25 | 0.07 | 0.06 | 0.62 |
| PPR motif 4 | 288, T | 291, N | 321, D | TND | 0.14 | 0.08 | 0.07 | 0.71 |
| PPR motif 5 | 323, I | 326, A | 356, H | *AH | 0.41 | 0.08 | 0.07 | 0.45 |
| PPR motif 6 | 358, P | 361, N | 396, N | *NN | 0.12 | 0.44 | 0.13 | 0.30 |
| PPR motif 7 | 398, D | 401, G | 435, D | *GD | 0.09 | 0.09 | 0.59 | 0.25 |
| PPR motif 8 | 437, L | 440, C | 470, D | *CD | 0.30 | 0.15 | 0.35 | 0.20 |
| PPR motif 9 | 472, P | 475, R | 505, V | *R* | 0.25 | 0.07 | 0.06 | 0.62 |
| PPR motif 10 | 507, D | 510, A | 540, D | *AD | 0.10 | 0.22 | 0.39 | 0.29 |
| PPR motif 11 | 542, S | 545, D | 575, T | *D* | 0.25 | 0.24 | 0.23 | 0.29 |

(B.G. means background)

The amino acid frequencies for these positions were confirmed for each protein, and compared with the amino acid frequencies for the same positions of the RNA-binding type motifs. The results are shown in FIG. 2. It became clear that the tendencies of the amino acid frequencies in the PPR motifs of the PPR proteins for which DNA-binding property is suggested, and the RNA-binding type motifs substantially agreed with each other. That is, it became clear that the PPR proteins that act to bind to DNA bind with nucleic acids according to same sequence rules as those of the PPR proteins that act to bind to RNA, and the RNA recognition codes described in the pending patent application of the inventors of the present invention (PCT/JP2012/077274) can be applied as the DNA recognition codes of the PPR proteins that act to bind to DNA.

With reference to the RNA recognition codes described in the non-patent document (Yagi, Y. et al., Plos One, 2013, 8, e57286), the DNA-binding type PPR motifs that selectively bind to each corresponding base were evaluated. More precisely, a chi square test was performed on the basis of occurrence nucleotide frequencies shown in Table 6 and expected nucleotide frequencies calculated from the background frequencies. The test was performed for each base (NT), purine or pyrimidine (AG or CT, PY), hydrogen bond group (AT or GC, HB), or amino or keto form (AC or GT). Significant value was defined as P<0.06 (5E-02, 5% significance level), and when a significant value was obtained in any of the tests, the combination of No. 1 amino acid, No. 4 amino acid, and No. "ii" (−2) amino acid was chosen.

In Table 1, the combinations of the amino acids that showed significant base selectivity were mentioned. That is, these results mean that the PPR motifs having the amino acid species of the No. 1 amino acid, No. 4 amino acid, and No. "ii" (−2) amino acid ("NSRs (1, 4, and ii)" in the table) that provided a significant P value are PPR motifs that impart base-selective binding ability, and a larger "positive" value obtained after the subtraction of the background means higher base selectivity for the base. Among the No. 1 amino acid, No. 4 amino acid, and No. "ii" (−2) amino acid, the No. 4 amino acid most strongly affects the base selectivity, the No. "ii" (−2) amino acid affects the base selectivity next strongly, and the No. 1 amino acid most weakly affects the base selectivity among the three amino acids.

TABLE 6

Base selectivity of DNA-binding code

| NSRs (1, 4, ii) | occurence of the NSR(s) | Probability matrix | | | | Subtraction for background | | | |
|---|---|---|---|---|---|---|---|---|---|
| | | A | C | G | T | A | C | G | T |
| *GD | 14 | 0.10 | 0.06 | 0.57 | 0.28 | −0.16 | −0.15 | 0.40 | −0.08 |
| EGD | 8 | 0.07 | 0.05 | 0.69 | 0.19 | −0.19 | −0.16 | 0.52 | −0.17 |
| *GN | 11 | 0.55 | 0.10 | 0.04 | 0.31 | 0.29 | −0.11 | −0.13 | −0.05 |
| EGN | 5 | 0.63 | 0.06 | 0.05 | 0.25 | 0.37 | −0.15 | −0.12 | −0.11 |
| *GS | 3 | 0.57 | 0.23 | 0.06 | 0.14 | 0.31 | 0.02 | −0.11 | −0.22 |
| *I* | 15 | 0.15 | 0.29 | 0.10 | 0.45 | −0.11 | 0.08 | −0.07 | 0.09 |
| *IN | 4 | 0.17 | 0.28 | 0.06 | 0.50 | −0.09 | 0.07 | −0.11 | 0.14 |
| *L* | 23 | 0.20 | 0.30 | 0.03 | 0.47 | −0.06 | 0.09 | −0.14 | 0.11 |
| *LD | 6 | 0.19 | 0.47 | 0.05 | 0.28 | −0.07 | 0.26 | −0.12 | −0.08 |
| *LK | 3 | 0.09 | 0.08 | 0.06 | 0.77 | −0.17 | −0.13 | −0.11 | 0.41 |
| *M* | 10 | 0.14 | 0.15 | 0.15 | 0.56 | −0.12 | −0.06 | −0.02 | 0.20 |
| *MD | 9 | 0.15 | 0.13 | 0.17 | 0.55 | −0.11 | −0.08 | 0.00 | 0.19 |
| IMD | 4 | 0.09 | 0.24 | 0.06 | 0.62 | −0.17 | 0.03 | −0.11 | 0.26 |
| *N* | 147 | 0.11 | 0.33 | 0.10 | 0.45 | −0.15 | 0.12 | −0.07 | 0.09 |
| *ND | 72 | 0.11 | 0.18 | 0.10 | 0.61 | −0.15 | −0.03 | −0.07 | 0.25 |
| FND | 13 | 0.23 | 0.19 | 0.10 | 0.49 | −0.03 | −0.02 | −0.07 | 0.13 |
| GND | 3 | 0.09 | 0.08 | 0.06 | 0.77 | −0.17 | −0.13 | −0.11 | 0.41 |
| IND | 5 | 0.22 | 0.13 | 0.05 | 0.60 | −0.04 | −0.08 | −0.12 | 0.24 |
| TND | 3 | 0.15 | 0.08 | 0.06 | 0.72 | −0.11 | −0.13 | −0.11 | 0.36 |
| VND | 23 | 0.06 | 0.25 | 0.06 | 0.63 | −0.20 | 0.04 | −0.11 | 0.27 |
| YND | 6 | 0.08 | 0.30 | 0.11 | 0.52 | −0.18 | 0.09 | −0.06 | 0.16 |
| *NN | 34 | 0.15 | 0.45 | 0.14 | 0.27 | −0.11 | 0.24 | −0.03 | −0.09 |
| INN | 7 | 0.12 | 0.49 | 0.05 | 0.34 | −0.14 | 0.28 | −0.12 | −0.02 |
| SNN | 3 | 0.09 | 0.60 | 0.06 | 0.24 | −0.17 | 0.39 | −0.11 | −0.12 |
| VNN | 10 | 0.20 | 0.53 | 0.04 | 0.23 | −0.06 | 0.32 | −0.13 | −0.13 |
| *NS | 13 | 0.11 | 0.47 | 0.07 | 0.36 | −0.15 | 0.26 | −0.10 | 0.00 |
| VNS | 5 | 0.08 | 0.66 | 0.05 | 0.21 | −0.18 | 0.45 | −0.12 | −0.15 |
| *NT | 13 | 0.12 | 0.52 | 0.13 | 0.24 | −0.14 | 0.31 | −0.04 | −0.12 |
| VNT | 5 | 0.08 | 0.57 | 0.05 | 0.30 | −0.16 | 0.36 | −0.12 | −0.06 |
| *NW | 11 | 0.14 | 0.32 | 0.13 | 0.41 | −0.12 | 0.11 | −0.04 | 0.05 |
| INW | 3 | 0.09 | 0.29 | 0.06 | 0.56 | −0.17 | 0.08 | −0.11 | 0.20 |
| *P* | 17 | 0.10 | 0.06 | 0.11 | 0.73 | −0.16 | −0.15 | −0.06 | 0.37 |
| *PD | 9 | 0.06 | 0.09 | 0.10 | 0.75 | −0.20 | −0.12 | −0.07 | 0.39 |
| FPD | 3 | 0.09 | 0.08 | 0.06 | 0.77 | −0.17 | −0.13 | −0.11 | 0.41 |
| YPD | 3 | 0.09 | 0.08 | 0.06 | 0.77 | −0.17 | −0.13 | −0.11 | 0.41 |
| *S* | 49 | 0.38 | 0.13 | 0.20 | 0.29 | 0.12 | −0.08 | 0.03 | −0.07 |
| *SN | 18 | 0.63 | 0.08 | 0.05 | 0.24 | 0.37 | −0.13 | −0.12 | −0.12 |
| FSN | 7 | 0.63 | 0.13 | 0.08 | 0.16 | 0.37 | −0.08 | −0.09 | −0.20 |
| VSN | 6 | 0.60 | 0.10 | 0.05 | 0.25 | 0.34 | −0.11 | −0.12 | −0.11 |
| *T* | 86 | 0.45 | 0.09 | 0.31 | 0.15 | 0.19 | −0.12 | 0.14 | −0.21 |
| *TD | 32 | 0.13 | 0.12 | 0.61 | 0.14 | −0.13 | −0.09 | 0.44 | −0.22 |
| VTD | 7 | 0.07 | 0.06 | 0.67 | 0.20 | −0.19 | −0.15 | 0.50 | −0.16 |
| *TN | 31 | 0.66 | 0.08 | 0.13 | 0.13 | 0.40 | −0.13 | −0.04 | −0.23 |
| FTN | 4 | 0.75 | 0.07 | 0.06 | 0.12 | 0.49 | −0.14 | −0.11 | −0.24 |
| ITN | 5 | 0.77 | 0.06 | 0.05 | 0.11 | 0.51 | −0.15 | −0.12 | −0.25 |
| VTN | 10 | 0.63 | 0.13 | 0.15 | 0.09 | 0.37 | −0.08 | −0.02 | −0.27 |
| *V* | 48 | 0.29 | 0.21 | 0.08 | 0.43 | 0.03 | 0.00 | −0.09 | 0.07 |
| IVD | 3 | 0.31 | 0.50 | 0.06 | 0.14 | 0.05 | 0.29 | −0.11 | −0.22 |
| *VG | 5 | 0.22 | 0.48 | 0.05 | 0.25 | −0.04 | 0.27 | −0.12 | −0.11 |
| *VT | 4 | 0.25 | 0.07 | 0.06 | 0.62 | −0.01 | −0.14 | −0.11 | 0.26 |
| Background frequency | | 0.26 | 0.21 | 0.17 | 0.36 | | | | |

Example 2: Evaluation of Sequence-Specific DNA-Binding Ability PPR Molecules

In this example, artificial transcription factors were prepared by fusing VP64, which is a transcription activation domain, to the three kinds of DNA-binding type (expectedly) PPR molecules, p63, pTac2, and GUN1, and by examining whether they could activate luciferase reporters each having a corresponding target sequence in a human cultured cell, whether the PPR molecules had a sequence-specific DNA-binding ability or not was determined (FIG. 5).

Experimental Method

1. Preparation of PPR-VP64 Expression Vector

Only the parts corresponding to the PPR motifs in the coding sequences of p63, pTac2, and GUN1 were prepared by artificial synthesis. For the DNA synthesis, the artificial gene synthesis service of Biomatik was used. The pCS2P vector having the CMV promoter was used as a backbone vector, and each synthesized PPR sequence was inserted into it. Further, the Flag tag and nuclear transfer signal were inserted at the N-terminus of the PPR sequence, and the VP64 sequence was inserted at the C-terminus of the same. The produced sequences of p63-VP64, pTac2-VP64, and GUN1-VP64 are shown in Sequence Listing as SEQ ID NOS: 7 to 9.

2. Preparation of Reporter Vector Having PPR Target Sequence

A reporter vector (pminCMV-luc2, SEQ ID NO: 10) was prepared, in which the firefly luciferase gene was ligated downstream from the Minimal CMV promoter, and a multi-cloning site was placed upstream of the promoter. The predicted target sequence of each PPR was inserted into the vector at the multi-cloning site. The target sequence of each PPR (TCTATCACT for p63, AACTTTCGTCACTCA for pTac2, and AATTTGTCGAT for GUN1, SEQ ID NOS: 11 to 13 in Sequence Listing) was determined by predicting the motif-DNA recognition codes of DNA-binding type PPR from the motif-RNA recognition codes observed in the RNA-binding type PPR. For each PPR, sequences containing 4 or 8 of target sequences were prepared, and used in the following assay. The nucleotide sequences of the vectors are shown as SEQ ID NOS: 14 to 19 in Sequence Listing.

3. Transfection into HEK293 T cell

The PPR-VP64 expression vector prepared in the section 1, the firefly luciferase expression vector prepared in the section 2, and the pRL-CMV vector (expression vector for *Renilla* luciferase, Promega) as a reference were introduced by using Lipofectamine LTX (Life Technologies). The DMEM medium (25 µl) was added to each well of a 96-well plate, and a mixture containing the PPR-VP64 expression vector (400 ng), firefly luciferase expression vector (100 ng), and pRL-CMV vector (20 ng) was further added. Then, a mixture of the DMEM medium (25 up and Lipofectamine LTX (0.7 µl) was added to each well, the plate was left standing at room temperature for 30 minutes, then $6\times10^4$ of the HEK293 T cells suspended in the DMEM medium containing 15% fetal bovine serum (100 µl) were added, and the cells were cultured at 37° C. in a $CO_2$ incubator for 24 hours.

4. Luciferase Assay

Luciferase assay was performed by using Dual-Glo Luciferase Assay System (Promega) in accordance with the instructions attached to the kit. For the measurement of the luciferase activity, TriStar LB 941 Plate Reader (Berthold) was used.

(Results and Discussion)

The luciferase activity was compared for the cases of introducing pTac2-VP64 or GUN1-VP64 together with pminCMV-luc2 for a negative control, or the reporter vector having 4 or 8 target sequences (table mentioned below, FIG. 6). The comparison of the activity was performed on the basis of standardized scores obtained by dividing the measured values obtained with Fluc (firefly luciferase) with the measured value obtained with Riuc (*Renilla* luciferase) as the reference (Fluc/Rluc). As a result, there was observed a tendency that the activity increased with increase of the number of the target sequence for the both cases, and thus it was verified that each of the PPR-VP64 molecules specifically bound to each target sequence, and functioned as a site-specific transcription activator.

TABLE 7

| | Fluc reporter | PPR-VP64 | Reference | Fluc | Rluc | Fluc/Rluc | Fold activation |
|---|---|---|---|---|---|---|---|
| pTac2-VP64 (negative control) | pminCMV-luc2 | pTac2-VP64 | pRL-CMV | 47744 | 4948 | 9.649151172 | 1 |
| pTac2-VP64 (4x target) | pTac2-4x target | pTac2-VP64 | pRL-CMV | 133465 | 4757 | 28.05654824 | 2.907670089 |
| pTac2-VP64 (8x target) | pTac2-8x target | pTac2-VP64 | pRL-CMV | 189146 | 4011 | 47.15681875 | 4.807146840 |
| GUN1-VP64 (negative control) | pminCMV-luc2 | GUN1-VP64 | pRL-CMV | 29590 | 3799 | 7.788891814 | 1 |
| GUN1-VP64 (4x target) | GUN1-4x target | GUN1-VP64 | pRL-CMV | 61070 | 2727 | 22.39457279 | 2.875193715 |
| GUN1-VP64 (8x target) | GUN1-8x target | GUN1-VP64 | pRL-CMV | 66982 | 2731 | 24.52654705 | 3.14891356 |

The invention claimed is:

1. A pentatricopeptide repeat (PPR) fusion protein comprising:
   9 PPR motifs belonging to the p63 protein consisting of the amino acid sequence of SEQ ID NO: 1,
   11 PPR motifs belonging to the GUN1 protein consisting of the amino acid sequence of SEQ ID NO: 2,
   15 PPR motifs belonging to the pTac2 protein consisting of the amino acid sequence of SEC) ID NO: 3,
   10 PPR motifs belonging to the DG1 protein consisting of the amino acid sequence of SEQ ID NO: 4, or
   11 PPR motifs belonging to the GRP23 protein consisting of the amino acid sequence of SEQ ID NO: 5; and
   a nuclear transfer signal inserted at an N-terminus of the PPR protein, wherein the nuclear transfer signal is encoded by a polynucleotide consisting of positions 165-185 of any one of SEQ ID NOs: 7-9.

2. A complex consisting of the PPR protein according to claim 1 and a target sequence-specific DNA-cleaving enzyme, wherein the DNA-cleaving enzyme is the nuclease domain of FokI (SEC) ID NO: 6).

* * * * *

SEQUENCE LISTING

<160> NUMBER OF SEQ ID NOS: 19

<210> SEQ ID NO 1
<211> LENGTH: 596
<212> TYPE: PRT
<213> ORGANISM: Arabidopsis thaliana

<400> SEQUENCE: 1

Met Phe Ala Leu Ser Lys Val Leu Arg Arg Thr Gln Arg Leu Arg Leu
1               5                   10                  15

-continued

```
Gly Ala Cys Ser Ala Val Phe Ser Lys Asp Ile Gln Leu Gly Gly Glu
            20                  25                  30

Arg Ser Phe Asp Ser Asn Ser Ile Ala Ser Thr Lys Arg Glu Ala Val
        35                  40                  45

Pro Arg Phe Tyr Glu Ile Ser Ser Leu Ser Asn Arg Ala Leu Ser Ser
50                  55                  60

Ser Ala Gly Thr Lys Ser Asp Gln Glu Glu Asp Asp Leu Glu Asp Gly
65                  70                  75                  80

Phe Ser Glu Leu Glu Gly Ser Lys Ser Gly Gln Gly Ser Thr Ser Ser
                85                  90                  95

Asp Glu Asp Glu Gly Lys Leu Ser Ala Asp Glu Glu Glu Glu Glu Glu
            100                 105                 110

Leu Asp Leu Ile Glu Thr Asp Val Ser Arg Lys Thr Val Glu Lys Lys
        115                 120                 125

Gln Ser Glu Leu Phe Lys Thr Ile Val Ser Ala Pro Gly Leu Ser Ile
130                 135                 140

Gly Ser Ala Leu Asp Lys Trp Val Glu Glu Gly Asn Glu Ile Thr Arg
145                 150                 155                 160

Val Glu Ile Ala Lys Ala Met Leu Gln Leu Arg Arg Arg Arg Met Tyr
                165                 170                 175

Gly Arg Ala Leu Gln Met Ser Glu Trp Leu Glu Ala Asn Lys Lys Ile
            180                 185                 190

Glu Met Thr Glu Arg Asp Tyr Ala Ser Arg Leu Asp Leu Thr Val Lys
        195                 200                 205

Ile Arg Gly Leu Glu Lys Gly Glu Ala Cys Met Gln Lys Ile Pro Lys
210                 215                 220

Ser Phe Lys Gly Glu Val Leu Tyr Arg Thr Leu Leu Ala Asn Cys Val
225                 230                 235                 240

Ala Ala Gly Asn Val Lys Lys Ser Glu Leu Val Phe Asn Lys Met Lys
                245                 250                 255

Asp Leu Gly Phe Pro Leu Ser Gly Phe Thr Cys Asp Gln Met Leu Leu
            260                 265                 270

Leu His Lys Arg Ile Asp Arg Lys Lys Ile Ala Asp Val Leu Leu Leu
        275                 280                 285

Met Glu Lys Glu Asn Ile Lys Pro Ser Leu Leu Thr Tyr Lys Ile Leu
290                 295                 300

Ile Asp Val Lys Gly Ala Thr Asn Asp Ile Ser Gly Met Glu Gln Ile
305                 310                 315                 320

Leu Glu Thr Met Lys Asp Glu Gly Val Glu Leu Asp Phe Gln Thr Gln
                325                 330                 335

Ala Leu Thr Ala Arg His Tyr Ser Gly Ala Gly Leu Lys Asp Lys Ala
            340                 345                 350

Glu Lys Val Leu Lys Glu Met Glu Gly Glu Ser Leu Glu Ala Asn Arg
        355                 360                 365

Arg Ala Phe Lys Asp Leu Leu Ser Ile Tyr Ala Ser Leu Gly Arg Glu
370                 375                 380

Asp Glu Val Lys Arg Ile Trp Lys Ile Cys Glu Ser Lys Pro Tyr Phe
385                 390                 395                 400

Glu Glu Ser Leu Ala Ala Ile Gln Ala Phe Gly Lys Leu Asn Lys Val
                405                 410                 415

Gln Glu Ala Glu Ala Ile Phe Glu Lys Ile Val Lys Met Asp Arg Arg
            420                 425                 430
```

Ala Ser Ser Ser Thr Tyr Ser Val Leu Leu Arg Val Tyr Val Asp His
            435                 440                 445

Lys Met Leu Ser Lys Gly Lys Asp Leu Val Lys Arg Met Ala Glu Ser
        450                 455                 460

Gly Cys Arg Ile Glu Ala Thr Thr Trp Asp Ala Leu Ile Lys Leu Tyr
465                 470                 475                 480

Val Glu Ala Gly Glu Val Lys Ala Asp Ser Leu Leu Asp Lys Ala
                485                 490                 495

Ser Lys Gln Ser His Thr Lys Leu Met Met Asn Ser Phe Met Tyr Ile
                500                 505                 510

Met Asp Glu Tyr Ser Lys Arg Gly Asp Val His Asn Thr Glu Lys Ile
            515                 520                 525

Phe Leu Lys Met Arg Glu Ala Gly Tyr Thr Ser Arg Leu Arg Gln Phe
        530                 535                 540

Gln Ala Leu Met Gln Ala Tyr Ile Asn Ala Lys Ser Pro Ala Tyr Gly
545                 550                 555                 560

Met Arg Asp Arg Leu Lys Ala Asp Asn Ile Phe Pro Asn Lys Ser Met
                565                 570                 575

Ala Ala Gln Leu Ala Gln Gly Asp Pro Phe Lys Lys Thr Ala Ile Ser
            580                 585                 590

Asp Ile Leu Asp
        595

<210> SEQ ID NO 2
<211> LENGTH: 918
<212> TYPE: PRT
<213> ORGANISM: Arabidopsis thaliana

<400> SEQUENCE: 2

Met Ala Ser Thr Pro Pro His Trp Val Thr Thr Asn Asn His Arg
1               5                   10                  15

Pro Trp Leu Pro Gln Arg Pro Arg Pro Gly Arg Ser Val Thr Ser Ala
            20                  25                  30

Pro Pro Ser Ser Ser Ala Ser Val Ser Ser Ala His Leu Ser Gln Thr
        35                  40                  45

Thr Pro Asn Phe Ser Pro Leu Gln Thr Pro Lys Ser Asp Phe Ser Gly
    50                  55                  60

Arg Gln Ser Thr Arg Phe Val Ser Pro Ala Thr Asn Asn His Arg Gln
65                  70                  75                  80

Thr Arg Gln Asn Pro Asn Tyr Asn His Arg Pro Tyr Gly Ala Ser Ser
                85                  90                  95

Ser Pro Arg Gly Ser Ala Pro Pro Ser Ser Val Ala Thr Val Ala
            100                 105                 110

Pro Ala Gln Leu Ser Gln Pro Pro Asn Phe Ser Pro Leu Gln Thr Pro
        115                 120                 125

Lys Ser Asp Leu Ser Ser Asp Phe Ser Gly Arg Arg Ser Thr Arg Phe
    130                 135                 140

Val Ser Lys Met His Phe Gly Arg Gln Lys Thr Thr Met Ala Thr Arg
145                 150                 155                 160

His Ser Ser Ala Ala Glu Asp Ala Leu Gln Asn Ala Ile Asp Phe Ser
                165                 170                 175

Gly Asp Asp Glu Met Phe His Ser Leu Met Leu Ser Phe Glu Ser Lys
            180                 185                 190

Leu Cys Gly Ser Asp Asp Cys Thr Tyr Ile Ile Arg Glu Leu Gly Asn
        195                 200                 205

```
Arg Asn Glu Cys Asp Lys Ala Val Gly Phe Tyr Glu Phe Ala Val Lys
        210                 215                 220
Arg Glu Arg Arg Lys Asn Glu Gln Gly Lys Leu Ala Ser Ala Met Ile
225                 230                 235                 240
Ser Thr Leu Gly Arg Tyr Gly Lys Val Thr Ile Ala Lys Arg Ile Phe
                245                 250                 255
Glu Thr Ala Phe Ala Gly Gly Tyr Gly Asn Thr Val Tyr Ala Phe Ser
            260                 265                 270
Ala Leu Ile Ser Ala Tyr Gly Arg Ser Gly Leu His Glu Glu Ala Ile
        275                 280                 285
Ser Val Phe Asn Ser Met Lys Glu Tyr Gly Leu Arg Pro Asn Leu Val
290                 295                 300
Thr Tyr Asn Ala Val Ile Asp Ala Cys Gly Lys Gly Met Glu Phe
305                 310                 315                 320
Lys Gln Val Ala Lys Phe Phe Asp Glu Met Gln Arg Asn Gly Val Gln
                325                 330                 335
Pro Asp Arg Ile Thr Phe Asn Ser Leu Leu Ala Val Cys Ser Arg Gly
            340                 345                 350
Gly Leu Trp Glu Ala Ala Arg Asn Leu Phe Asp Glu Met Thr Asn Arg
        355                 360                 365
Arg Ile Glu Gln Asp Val Phe Ser Tyr Asn Thr Leu Leu Asp Ala Ile
    370                 375                 380
Cys Lys Gly Gly Gln Met Asp Leu Ala Phe Glu Ile Leu Ala Gln Met
385                 390                 395                 400
Pro Val Lys Arg Ile Met Pro Asn Val Val Ser Tyr Ser Thr Val Ile
                405                 410                 415
Asp Gly Phe Ala Lys Ala Gly Arg Phe Asp Glu Ala Leu Asn Leu Phe
            420                 425                 430
Gly Glu Met Arg Tyr Leu Gly Ile Ala Leu Asp Arg Val Ser Tyr Asn
        435                 440                 445
Thr Leu Leu Ser Ile Tyr Thr Lys Val Gly Arg Ser Glu Glu Ala Leu
    450                 455                 460
Asp Ile Leu Arg Glu Met Ala Ser Val Gly Ile Lys Lys Asp Val Val
465                 470                 475                 480
Thr Tyr Asn Ala Leu Leu Gly Gly Tyr Gly Lys Gln Gly Lys Tyr Asp
                485                 490                 495
Glu Val Lys Lys Val Phe Thr Glu Met Lys Arg Glu His Val Leu Pro
            500                 505                 510
Asn Leu Leu Thr Tyr Ser Thr Leu Ile Asp Gly Tyr Ser Lys Gly Gly
        515                 520                 525
Leu Tyr Lys Glu Ala Met Glu Ile Phe Arg Glu Phe Lys Ser Ala Gly
    530                 535                 540
Leu Arg Ala Asp Val Val Leu Tyr Ser Ala Leu Ile Asp Ala Leu Cys
545                 550                 555                 560
Lys Asn Gly Leu Val Gly Ser Ala Val Ser Leu Ile Asp Glu Met Thr
                565                 570                 575
Lys Glu Gly Ile Ser Pro Asn Val Val Thr Tyr Asn Ser Ile Ile Asp
            580                 585                 590
Ala Phe Gly Arg Ser Ala Thr Met Asp Arg Ser Ala Asp Tyr Ser Asn
        595                 600                 605
Gly Gly Ser Leu Pro Phe Ser Ser Ala Leu Ser Ala Leu Thr Glu
    610                 615                 620
```

Thr Glu Gly Asn Arg Val Ile Gln Leu Phe Gly Gln Leu Thr Thr Glu
625                 630                 635                 640

Ser Asn Asn Arg Thr Thr Lys Asp Cys Glu Glu Gly Met Gln Glu Leu
            645                 650                 655

Ser Cys Ile Leu Glu Val Phe Arg Lys Met His Gln Leu Glu Ile Lys
            660                 665                 670

Pro Asn Val Val Thr Phe Ser Ala Ile Leu Asn Ala Cys Ser Arg Cys
            675                 680                 685

Asn Ser Phe Glu Asp Ala Ser Met Leu Leu Glu Glu Leu Arg Leu Phe
        690                 695                 700

Asp Asn Lys Val Tyr Gly Val His Gly Leu Leu Met Gly Gln Arg
705                 710                 715                 720

Glu Asn Val Trp Leu Gln Ala Gln Ser Leu Phe Asp Lys Val Asn Glu
                725                 730                 735

Met Asp Gly Ser Thr Ala Ser Ala Phe Tyr Asn Ala Leu Thr Asp Met
            740                 745                 750

Leu Trp His Phe Gly Lys Arg Gly Ala Glu Leu Val Ala Leu Glu
        755                 760                 765

Gly Arg Ser Arg Gln Val Trp Glu Asn Val Trp Ser Asp Ser Cys Leu
770                 775                 780

Asp Leu His Leu Met Ser Ser Gly Ala Ala Arg Ala Met Val His Ala
785                 790                 795                 800

Trp Leu Leu Asn Ile Arg Ser Ile Val Tyr Glu Gly His Glu Leu Pro
                805                 810                 815

Lys Val Leu Ser Ile Leu Thr Gly Trp Gly Lys His Ser Lys Val Val
                820                 825                 830

Gly Asp Gly Ala Leu Arg Arg Ala Val Glu Val Leu Leu Arg Gly Met
        835                 840                 845

Asp Ala Pro Phe His Leu Ser Lys Cys Asn Met Gly Arg Phe Thr Ser
850                 855                 860

Ser Gly Ser Val Val Ala Thr Trp Leu Arg Glu Ser Ala Thr Leu Lys
865                 870                 875                 880

Leu Leu Ile Leu His Asp His Ile Thr Thr Ala Thr Ala Thr Thr Thr
                885                 890                 895

Thr Met Lys Ser Thr Asp Gln Gln Gln Arg Lys Gln Thr Ser Phe Ala
            900                 905                 910

Leu Gln Pro Leu Leu Leu
        915

<210> SEQ ID NO 3
<211> LENGTH: 862
<212> TYPE: PRT
<213> ORGANISM: Arabidopsis thaliana

<400> SEQUENCE: 3

Met Asn Leu Ala Ile Pro Asn Pro Asn Ser His His Leu Ser Phe Leu
1               5                   10                  15

Ile Gln Asn Ser Ser Phe Ile Gly Asn Arg Arg Phe Ala Asp Gly Asn
                20                  25                  30

Arg Leu Arg Phe Leu Ser Gly Gly Asn Arg Lys Pro Cys Ser Phe Ser
            35                  40                  45

Gly Lys Ile Lys Ala Lys Thr Lys Asp Leu Val Leu Gly Asn Pro Ser
    50                  55                  60

Val Ser Val Glu Lys Gly Lys Tyr Ser Tyr Asp Val Glu Ser Leu Ile
65                  70                  75                  80

```
Asn Lys Leu Ser Ser Leu Pro Pro Arg Gly Ser Ile Ala Arg Cys Leu
                85                  90                  95

Asp Ile Phe Lys Asn Lys Leu Ser Leu Asn Asp Phe Ala Leu Val Phe
           100                 105                 110

Lys Glu Phe Ala Gly Arg Gly Asp Trp Gln Arg Ser Leu Arg Leu Phe
       115                 120                 125

Lys Tyr Met Gln Arg Gln Ile Trp Cys Lys Pro Asn Glu His Ile Tyr
   130                 135                 140

Thr Ile Met Ile Ser Leu Leu Gly Arg Glu Gly Leu Leu Asp Lys Cys
145                 150                 155                 160

Leu Glu Val Phe Asp Glu Met Pro Ser Gln Gly Val Ser Arg Ser Val
               165                 170                 175

Phe Ser Tyr Thr Ala Leu Ile Asn Ala Tyr Gly Arg Asn Gly Arg Tyr
           180                 185                 190

Glu Thr Ser Leu Glu Leu Leu Asp Arg Met Lys Asn Glu Lys Ile Ser
       195                 200                 205

Pro Ser Ile Leu Thr Tyr Asn Thr Val Ile Asn Ala Cys Ala Arg Gly
   210                 215                 220

Gly Leu Asp Trp Glu Gly Leu Leu Gly Leu Phe Ala Glu Met Arg His
225                 230                 235                 240

Glu Gly Ile Gln Pro Asp Ile Val Thr Tyr Asn Thr Leu Leu Ser Ala
               245                 250                 255

Cys Ala Ile Arg Gly Leu Gly Asp Glu Ala Glu Met Val Phe Arg Thr
           260                 265                 270

Met Asn Asp Gly Gly Ile Val Pro Asp Leu Thr Thr Tyr Ser His Leu
       275                 280                 285

Val Glu Thr Phe Gly Lys Leu Arg Arg Leu Glu Lys Val Cys Asp Leu
   290                 295                 300

Leu Gly Glu Met Ala Ser Gly Gly Ser Leu Pro Asp Ile Thr Ser Tyr
305                 310                 315                 320

Asn Val Leu Leu Glu Ala Tyr Ala Lys Ser Gly Ser Ile Lys Glu Ala
               325                 330                 335

Met Gly Val Phe His Gln Met Gln Ala Ala Gly Cys Thr Pro Asn Ala
           340                 345                 350

Asn Thr Tyr Ser Val Leu Leu Asn Leu Phe Gly Gln Ser Gly Arg Tyr
       355                 360                 365

Asp Asp Val Arg Gln Leu Phe Leu Glu Met Lys Ser Ser Asn Thr Asp
   370                 375                 380

Pro Asp Ala Ala Thr Tyr Asn Ile Leu Ile Glu Val Phe Gly Glu Gly
385                 390                 395                 400

Gly Tyr Phe Lys Glu Val Val Thr Leu Phe His Asp Met Val Glu Glu
               405                 410                 415

Asn Ile Glu Pro Asp Met Glu Thr Tyr Glu Gly Ile Ile Phe Ala Cys
           420                 425                 430

Gly Lys Gly Gly Leu His Glu Asp Ala Arg Lys Ile Leu Gln Tyr Met
       435                 440                 445

Thr Ala Asn Asp Ile Val Pro Ser Ser Lys Ala Tyr Thr Gly Val Ile
   450                 455                 460

Glu Ala Phe Gly Gln Ala Ala Leu Tyr Glu Glu Ala Leu Val Ala Phe
465                 470                 475                 480

Asn Thr Met His Glu Val Gly Ser Asn Pro Ser Ile Glu Thr Phe His
               485                 490                 495
```

```
Ser Leu Leu Tyr Ser Phe Ala Arg Gly Gly Leu Val Lys Glu Ser Glu
            500                 505                 510

Ala Ile Leu Ser Arg Leu Val Asp Ser Gly Ile Pro Arg Asn Arg Asp
        515                 520                 525

Thr Phe Asn Ala Gln Ile Glu Ala Tyr Lys Gln Gly Gly Lys Phe Glu
    530                 535                 540

Glu Ala Val Lys Thr Tyr Val Asp Met Glu Lys Ser Arg Cys Asp Pro
545                 550                 555                 560

Asp Glu Arg Thr Leu Glu Ala Val Leu Ser Val Tyr Ser Phe Ala Arg
                565                 570                 575

Leu Val Asp Glu Cys Arg Glu Gln Phe Glu Glu Met Lys Ala Ser Asp
            580                 585                 590

Ile Leu Pro Ser Ile Met Cys Tyr Cys Met Met Leu Ala Val Tyr Gly
        595                 600                 605

Lys Thr Glu Arg Trp Asp Asp Val Asn Glu Leu Leu Glu Glu Met Leu
    610                 615                 620

Ser Asn Arg Val Ser Asn Ile His Gln Val Ile Gly Gln Met Ile Lys
625                 630                 635                 640

Gly Asp Tyr Asp Asp Ser Asn Trp Gln Ile Val Glu Tyr Val Leu
                645                 650                 655

Asp Lys Leu Asn Ser Glu Gly Cys Gly Leu Gly Ile Arg Phe Tyr Asn
            660                 665                 670

Ala Leu Leu Asp Ala Leu Trp Trp Leu Gly Gln Lys Glu Arg Ala Ala
        675                 680                 685

Arg Val Leu Asn Glu Ala Thr Lys Arg Gly Leu Phe Pro Glu Leu Phe
    690                 695                 700

Arg Lys Asn Lys Leu Val Trp Ser Val Asp Val His Arg Met Ser Glu
705                 710                 715                 720

Gly Gly Met Tyr Thr Ala Leu Ser Val Trp Leu Asn Asp Ile Asn Asp
                725                 730                 735

Met Leu Leu Lys Gly Asp Leu Pro Gln Leu Ala Val Val Ser Val
            740                 745                 750

Arg Gly Gln Leu Glu Lys Ser Ser Ala Ala Arg Glu Ser Pro Ile Ala
        755                 760                 765

Lys Ala Ala Phe Ser Phe Leu Gln Asp His Val Ser Ser Ser Phe Ser
    770                 775                 780

Phe Thr Gly Trp Asn Gly Gly Arg Ile Met Cys Gln Arg Ser Gln Leu
785                 790                 795                 800

Lys Gln Leu Leu Ser Thr Lys Glu Pro Thr Ser Glu Glu Ser Glu Asn
                805                 810                 815

Lys Asn Leu Val Ala Leu Ala Asn Ser Pro Ile Phe Ala Ala Gly Thr
            820                 825                 830

Arg Ala Ser Thr Ser Ser Asp Thr Asn His Ser Gly Asn Pro Thr Gln
        835                 840                 845

Arg Arg Thr Arg Thr Lys Lys Glu Leu Ala Gly Ser Thr Ala
    850                 855                 860

<210> SEQ ID NO 4
<211> LENGTH: 798
<212> TYPE: PRT
<213> ORGANISM: Arabidopsis thaliana

<400> SEQUENCE: 4

Met Asp Ala Ser Val Val Arg Phe Ser Gln Ser Pro Ala Arg Val Pro
1               5                   10                  15
```

```
Pro Glu Phe Glu Pro Asp Met Glu Lys Ile Lys Arg Arg Leu Leu Lys
            20                  25                  30

Tyr Gly Val Asp Pro Thr Pro Lys Ile Leu Asn Asn Leu Arg Lys Lys
            35                  40                  45

Glu Ile Gln Lys His Asn Arg Arg Thr Lys Arg Glu Thr Glu Ser Glu
50                  55                  60

Ala Glu Val Tyr Thr Glu Ala Gln Lys Gln Ser Met Glu Glu Glu Ala
65                  70                  75                  80

Arg Phe Gln Thr Leu Arg Arg Glu Tyr Lys Gln Phe Thr Arg Ser Ile
            85                  90                  95

Ser Gly Lys Arg Gly Gly Asp Val Gly Leu Met Val Gly Asn Pro Trp
            100                 105                 110

Glu Gly Ile Glu Arg Val Lys Leu Lys Glu Leu Val Ser Gly Val Arg
            115                 120                 125

Arg Glu Glu Val Ser Ala Gly Glu Leu Lys Lys Glu Asn Leu Lys Glu
            130                 135                 140

Leu Lys Lys Ile Leu Glu Lys Asp Leu Arg Trp Val Leu Asp Asp Asp
145                 150                 155                 160

Val Asp Val Glu Glu Phe Asp Leu Asp Lys Glu Phe Asp Pro Ala Lys
            165                 170                 175

Arg Trp Arg Asn Glu Gly Glu Ala Val Arg Val Leu Val Asp Arg Leu
            180                 185                 190

Ser Gly Arg Glu Ile Asn Glu Lys His Trp Lys Phe Val Arg Met Met
            195                 200                 205

Asn Gln Ser Gly Leu Gln Phe Thr Glu Asp Gln Met Leu Lys Ile Val
210                 215                 220

Asp Arg Leu Gly Arg Lys Gln Ser Trp Lys Gln Ala Ser Ala Val Val
225                 230                 235                 240

His Trp Val Tyr Ser Asp Lys Lys Arg Lys His Leu Arg Ser Arg Phe
            245                 250                 255

Val Tyr Thr Lys Leu Leu Ser Val Leu Gly Phe Ala Arg Arg Pro Gln
            260                 265                 270

Glu Ala Leu Gln Ile Phe Asn Gln Met Leu Gly Asp Arg Gln Leu Tyr
            275                 280                 285

Pro Asp Met Ala Ala Tyr His Cys Ile Ala Val Thr Leu Gly Gln Ala
            290                 295                 300

Gly Leu Leu Lys Glu Leu Leu Lys Val Ile Glu Arg Met Arg Gln Lys
305                 310                 315                 320

Pro Thr Lys Leu Thr Lys Asn Leu Arg Gln Lys Asn Trp Asp Pro Val
            325                 330                 335

Leu Glu Pro Asp Leu Val Val Tyr Asn Ala Ile Leu Asn Ala Cys Val
            340                 345                 350

Pro Thr Leu Gln Trp Lys Ala Val Ser Trp Val Phe Val Glu Leu Arg
            355                 360                 365

Lys Asn Gly Leu Arg Pro Asn Gly Ala Thr Tyr Gly Leu Ala Met Glu
            370                 375                 380

Val Met Leu Glu Ser Gly Lys Phe Asp Arg Val His Asp Phe Phe Arg
385                 390                 395                 400

Lys Met Lys Ser Ser Gly Glu Ala Pro Lys Ala Ile Thr Tyr Lys Val
            405                 410                 415

Leu Val Arg Ala Leu Trp Arg Glu Gly Lys Ile Glu Glu Ala Val Glu
            420                 425                 430
```

```
Ala Val Arg Asp Met Glu Gln Lys Gly Val Ile Gly Thr Gly Ser Val
        435                 440                 445

Tyr Tyr Glu Leu Ala Cys Cys Leu Cys Asn Asn Gly Arg Trp Cys Asp
    450                 455                 460

Ala Met Leu Glu Val Gly Arg Met Lys Arg Leu Glu Asn Cys Arg Pro
465                 470                 475                 480

Leu Glu Ile Thr Phe Thr Gly Leu Ile Ala Ser Leu Asn Gly Gly
                485                 490                 495

His Val Asp Asp Cys Met Ala Ile Phe Gln Tyr Met Lys Asp Lys Cys
                500                 505                 510

Asp Pro Asn Ile Gly Thr Ala Asn Met Met Leu Lys Val Tyr Gly Arg
            515                 520                 525

Asn Asp Met Phe Ser Glu Ala Lys Glu Leu Phe Glu Glu Ile Val Ser
530                 535                 540

Arg Lys Glu Thr His Leu Val Pro Asn Glu Tyr Thr Tyr Ser Phe Met
545                 550                 555                 560

Leu Glu Ala Ser Ala Arg Ser Leu Gln Trp Glu Tyr Phe Glu His Val
                565                 570                 575

Tyr Gln Thr Met Val Leu Ser Gly Tyr Gln Met Asp Gln Thr Lys His
                580                 585                 590

Ala Ser Met Leu Ile Glu Ala Ser Arg Ala Gly Lys Trp Ser Leu Leu
            595                 600                 605

Glu His Ala Phe Asp Ala Val Leu Glu Asp Gly Glu Ile Pro His Pro
            610                 615                 620

Leu Phe Phe Thr Glu Leu Leu Cys His Ala Thr Ala Lys Gly Asp Phe
625                 630                 635                 640

Gln Arg Ala Ile Thr Leu Ile Asn Thr Val Ala Leu Ala Ser Phe Gln
                645                 650                 655

Ile Ser Glu Glu Glu Trp Thr Asp Leu Phe Glu Glu His Gln Asp Trp
            660                 665                 670

Leu Thr Gln Asp Asn Leu His Lys Leu Ser Asp His Leu Ile Glu Cys
            675                 680                 685

Asp Tyr Val Ser Glu Pro Thr Val Ser Asn Leu Ser Lys Ser Leu Lys
690                 695                 700

Ser Arg Cys Gly Ser Ser Ser Ser Ala Gln Pro Leu Leu Ala Val
705                 710                 715                 720

Asp Val Thr Thr Gln Ser Gln Gly Glu Lys Pro Glu Glu Asp Leu Leu
                725                 730                 735

Leu Gln Asp Thr Thr Met Glu Asp Asn Ser Ala Asn Gly Glu Ala
                740                 745                 750

Trp Glu Phe Thr Glu Thr Glu Leu Glu Thr Leu Gly Leu Glu Glu Leu
            755                 760                 765

Glu Ile Asp Asp Asp Glu Glu Ser Ser Asp Asp Ser Leu Ser Val
770                 775                 780

Tyr Asp Ile Leu Lys Glu Trp Glu Glu Ser Ser Lys Lys Glu
785                 790                 795

<210> SEQ ID NO 5
<211> LENGTH: 913
<212> TYPE: PRT
<213> ORGANISM: Arabidopsis thaliana

<400> SEQUENCE: 5

Met Ser Leu Ser His Leu Leu Arg Arg Leu Cys Thr Thr Thr Thr Thr
1               5                   10                  15
```

```
Thr Arg Ser Pro Leu Ser Ile Ser Phe Leu His Gln Arg Ile His Asn
             20              25              30

Ile Ser Leu Ser Pro Ala Asn Glu Asp Pro Glu Thr Thr Thr Gly Asn
         35              40              45

Asn Gln Asp Ser Glu Lys Tyr Pro Asn Leu Asn Pro Ile Pro Asn Asp
     50              55              60

Pro Ser Gln Phe Gln Ile Pro Gln Asn His Thr Pro Pro Ile Pro Tyr
 65              70              75              80

Pro Pro Ile Pro His Arg Thr Met Ala Phe Ser Ser Ala Glu Glu Ala
                 85              90              95

Ala Ala Glu Arg Arg Arg Lys Arg Arg Leu Arg Ile Glu Pro Pro
             100             105             110

Leu His Ala Leu Arg Arg Asp Pro Ser Ala Pro Pro Lys Arg Asp
         115             120             125

Pro Asn Ala Pro Arg Leu Pro Asp Ser Thr Ser Ala Leu Val Gly Gln
 130             135             140

Arg Leu Asn Leu His Asn Arg Val Gln Ser Leu Ile Arg Ala Ser Asp
145             150             155             160

Leu Asp Ala Ala Ser Lys Leu Ala Arg Gln Ser Val Phe Ser Asn Thr
             165             170             175

Arg Pro Thr Val Phe Thr Cys Asn Ala Ile Ile Ala Ala Met Tyr Arg
         180             185             190

Ala Lys Arg Tyr Ser Glu Ser Ile Ser Leu Phe Gln Tyr Phe Phe Lys
     195             200             205

Gln Ser Asn Ile Val Pro Asn Val Val Ser Tyr Asn Gln Ile Ile Asn
 210             215             220

Ala His Cys Asp Glu Gly Asn Val Asp Glu Ala Leu Glu Val Tyr Arg
225             230             235             240

His Ile Leu Ala Asn Ala Pro Phe Ala Pro Ser Ser Val Thr Tyr Arg
             245             250             255

His Leu Thr Lys Gly Leu Val Gln Ala Gly Arg Ile Gly Asp Ala Ala
         260             265             270

Ser Leu Leu Arg Glu Met Leu Ser Lys Gly Gln Ala Ala Asp Ser Thr
     275             280             285

Val Tyr Asn Asn Leu Ile Arg Gly Tyr Leu Asp Leu Gly Asp Phe Asp
 290             295             300

Lys Ala Val Glu Phe Phe Asp Glu Leu Lys Ser Lys Cys Thr Val Tyr
305             310             315             320

Asp Gly Ile Val Asn Ala Thr Phe Met Glu Tyr Trp Phe Glu Lys Gly
             325             330             335

Asn Asp Lys Glu Ala Met Glu Ser Tyr Arg Ser Leu Leu Asp Lys Lys
         340             345             350

Phe Arg Met His Pro Pro Thr Gly Asn Val Leu Leu Glu Val Phe Leu
     355             360             365

Lys Phe Gly Lys Lys Asp Glu Ala Trp Ala Leu Phe Asn Glu Met Leu
 370             375             380

Asp Asn His Ala Pro Pro Asn Ile Leu Ser Val Asn Ser Asp Thr Val
385             390             395             400

Gly Ile Met Val Asn Glu Cys Phe Lys Met Gly Glu Phe Ser Glu Ala
             405             410             415

Ile Asn Thr Phe Lys Lys Val Gly Ser Lys Val Thr Ser Lys Pro Phe
         420             425             430
```

```
Val Met Asp Tyr Leu Gly Tyr Cys Asn Ile Val Thr Arg Phe Cys Glu
            435                 440                 445
Gln Gly Met Leu Thr Glu Ala Glu Arg Phe Phe Ala Glu Gly Val Ser
        450                 455                 460
Arg Ser Leu Pro Ala Asp Ala Pro Ser His Arg Ala Met Ile Asp Ala
465                 470                 475                 480
Tyr Leu Lys Ala Glu Arg Ile Asp Asp Ala Val Lys Met Leu Asp Arg
                485                 490                 495
Met Val Asp Val Asn Leu Arg Val Ala Asp Phe Gly Ala Arg Val
                500                 505                 510
Phe Gly Glu Leu Ile Lys Asn Gly Lys Leu Thr Glu Ser Ala Glu Val
        515                 520                 525
Leu Thr Lys Met Gly Glu Arg Glu Pro Lys Pro Asp Pro Ser Ile Tyr
    530                 535                 540
Asp Val Val Arg Gly Leu Cys Asp Gly Asp Ala Leu Asp Gln Ala
545                 550                 555                 560
Lys Asp Ile Val Gly Glu Met Ile Arg His Asn Val Gly Val Thr Thr
                565                 570                 575
Val Leu Arg Glu Phe Ile Ile Glu Val Phe Glu Lys Ala Gly Arg Arg
            580                 585                 590
Glu Glu Ile Glu Lys Ile Leu Asn Ser Val Ala Arg Pro Val Arg Asn
        595                 600                 605
Ala Gly Gln Ser Gly Asn Thr Pro Pro Arg Val Pro Ala Val Phe Gly
    610                 615                 620
Thr Thr Pro Ala Ala Pro Gln Gln Pro Arg Asp Arg Ala Pro Trp Thr
625                 630                 635                 640
Ser Gln Gly Val Val His Ser Asn Ser Gly Trp Ala Asn Gly Thr Ala
                645                 650                 655
Gly Gln Thr Ala Gly Gly Ala Tyr Lys Ala Asn Asn Gly Gln Asn Pro
            660                 665                 670
Ser Trp Ser Asn Thr Ser Asp Asn Gln Gln Gln Ser Trp Ser Asn
        675                 680                 685
Gln Thr Ala Gly Gln Gln Pro Pro Ser Trp Ser Arg Gln Ala Pro Gly
    690                 695                 700
Tyr Gln Gln Gln Ser Trp Ser Gln Ser Gly Trp Ser Ser Pro
705                 710                 715                 720
Ser Gly His Gln Gln Ser Trp Thr Asn Gln Thr Ala Gly Gln Gln
                725                 730                 735
Pro Trp Ala Asn Gln Thr Pro Gly Gln Gln Gln Trp Ala Asn Gln
            740                 745                 750
Thr Pro Gly Gln Gln Gln Leu Ala Asn Gln Thr Pro Gly Gln Gln
        755                 760                 765
Gln Gln Trp Ala Asn Gln Thr Pro Gly Gln Gln Gln Trp Ala Asn
    770                 775                 780
Gln Asn Asn Gly His Gln Gln Pro Trp Ala Asn Gln Asn Thr Gly His
785                 790                 795                 800
Gln Gln Ser Trp Ala Asn Gln Thr Pro Ser Gln Gln Pro Trp Ala
                805                 810                 815
Asn Gln Thr Thr Gly Gln Gln Gly Trp Gly Asn Gln Thr Thr Gly
            820                 825                 830
Gln Gln Gln Gln Trp Ala Asn Gln Thr Ala Gly Gln Gln Ser Gly Trp
        835                 840                 845
Thr Ala Gln Gln Gln Trp Ser Asn Gln Thr Ala Ser His Gln Gln Ser
```

```
                 850                 855                 860
Gln Trp Leu Asn Pro Val Pro Gly Glu Val Ala Asn Gln Thr Pro Trp
865                 870                 875                 880

Ser Asn Ser Val Asp Ser His Leu Pro Gln Gln Gln Glu Pro Gly Pro
                885                 890                 895

Ser His Glu Cys Gln Glu Thr Gln Glu Lys Lys Val Val Glu Leu Arg
                900                 905                 910

Asn

<210> SEQ ID NO 6
<211> LENGTH: 196
<212> TYPE: PRT
<213> ORGANISM: Flabovacterium okeianocoites

<400> SEQUENCE: 6

Ala Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 7
<211> LENGTH: 5303
<212> TYPE: DNA
<213> ORGANISM: Artificial Sequence
<220> FEATURE:
<223> OTHER INFORMATION: p63-VP64

<400> SEQUENCE: 7
cgccattctg cctggggacg tcggagcaag cttgatttag gtgacactat agaatacaag      60
ctacttgttc tttttgcaag atctccacca tggactataa ggaccacgac ggagactaca     120
aggatcatga tattgattac aaagacgatg acgataagat ggccccaaag aagaagcgga     180
aggtcggtat ccccgggggc gaagtgctgt ataggacact gctggccaac tgcgtggctg     240
ctgggaacgt gaagaagtcc gaactggtct tcaacaagat gaaggatctg ggttccccc     300
```

```
tgagcggctt tacctgtgac caaatgctgc tgctgcacaa aaggattgat agaaagaaaa    360
tcgctgatgt cctgctgctg atggaaaagg aaaatatcaa gccaagcctg ctgacctaca    420
agatcctgat cgatgtgaag ggcgccacca acgacattag cgggatggaa cagattctgg    480
aaacaatgaa agacgagggc gtggagctgg atttccaaac acaggccctg acagccaggc    540
attactccgg cgctggactg aaagataagg cagaaaaggt gctgaaggaa atggagggag    600
agtccctgga agcaaatagg aggcccttta aggacctgct gtccatttac gcctccctgg    660
gcagagaaga cgaagtgaaa agaatttgga agatttgcga gtccaaacca ctctttgagg    720
aatccctggc cgctatccaa gcattcggca agctgaataa ggtgcaagaa gccgaggcaa    780
tcttcgaaaa gattgtgaag atggatagaa gagcaagctc cagcacatac tccgtcctgc    840
tgagagtgta cgtggatcat aagatgctga gcaaaggcaa agacctggtg aagagaatgg    900
ccgagagcgg gtgcagaatt gaagccacca cctgggacgc tctgatcaaa ctgtatgtcg    960
aggctgggga ggtggaaaaa gccgattccc tgctggataa agccagcaaa caatcccaca   1020
ctaaactgat gatgaatagc ttcatgtata tcatggacga gtatagcaag aggggcgacg   1080
tgcacaatac cgaaaaaatc tttctgaaaa tgagggaagc cgggtatact agcggatccg   1140
gacgggctga cgcattggac gattttgatc tggatatgct gggaagtgac gccctcgatg   1200
attttgacct tgacatgctt ggttcggatg ccccttgatga cttgacctc gacatgctcg   1260
gcagtgacgc ccttgatgat tcgacctgg acatgctgat taactctagt tgatctagat   1320
tctgcagccc tatagtgagt cgtattacgt agatccagac atgataagat acattgatga   1380
gtttggacaa accacaacta gaatgcagtg aaaaaaatgc tttatttgtg aaatttgtga   1440
tgctattgct ttatttgtaa ccattataag ctgcaataaa caagttaaca acaacaattg   1500
cattcatttt atgtttcagg ttcaggggga ggtgtgggag gttttttaat tcgcggccgc   1560
ggcgccaatg cattgggccc ggtacccagc ttttgttccc tttagtgagg gttaattgcg   1620
cgcttggcgt aatcatggtc atagctgttt cctgtgtgaa attgttatcc gctcacaatt   1680
ccacacaaca tacgagccgg aagcataaag tgtaaagcct ggggtgccta atgagtgagc   1740
taactcacat taattgcgtt gcgctcactg cccgctttcc agtcgggaaa cctgtcgtgc   1800
cagctgcatt aatgaatcgg ccaacgcgcg gggagaggcg gtttgcgtat tgggcgctct   1860
tccgcttcct cgctcactga ctcgctgcgc tcggtcgttc ggctgcggcg agcggtatca   1920
gctcactcaa aggcggtaat acggttatcc acagaatcag gggataacgc aggaaagaac   1980
atgtgagcaa aaggccagca aaaggccagg aaccgtaaaa aggccgcgtt gctggcgttt   2040
ttccataggc tccgcccccc tgacgagcat cacaaaaatc gacgctcaag tcagaggtgg   2100
cgaaacccga caggactata aagataccag gcgtttcccc ctggaagctc cctcgtgcgc   2160
tctcctgttc cgaccctgcc gcttaccgga tacctgtccg cctttctccc ttcgggaagc   2220
gtggcgcttt ctcatagctc acgctgtagg tatctcagtt cggtgtaggt cgttcgctcc   2280
aagctgggct gtgtgcacga accccccgtt cagcccgacc gctgcgcctt atccggtaac   2340
tatcgtcttg agtccaaccc ggtaagacac gacttatcgc cactggcagc agccactggt   2400
aacaggatta gcagagcgag gtatgtaggc ggtgctacag agttcttgaa gtggtggcct   2460
aactacggct acactagaag gacagtattt ggtatctgcg ctctgctgaa gccagttacc   2520
ttcggaaaaa gagttggtag ctcttgatcc ggcaaacaaa ccaccgctgg tagcggtggt   2580
ttttttgttt gcaagcagca gattacgcgc agaaaaaaag gatctcaaga agatcctttg   2640
```

```
atctttcta cggggtctga cgctcagtgg aacgaaaact cacgttaagg gattttggtc    2700
atgagattat caaaaaggat cttcacctag atccttttaa attaaaaatg aagttttaaa    2760
tcaatctaaa gtatatatga gtaaacttgg tctgacagtt accaatgctt aatcagtgag    2820
gcacctatct cagcgatctg tctatttcgt tcatccatag ttgcctgact ccccgtcgtg    2880
tagataacta cgatacggga gggcttacca tctggcccca gtgctgcaat gataccgcga    2940
gacccacgct caccggctcc agatttatca gcaataaacc agccagccgg aagggccgag    3000
cgcagaagtg gtcctgcaac tttatccgcc tccatccagt ctattaattg ttgccgggaa    3060
gctagagtaa gtagttcgcc agttaatagt ttgcgcaacg ttgttgccat tgctacaggc    3120
atcgtggtgt cacgctcgtc gtttggtatg gcttcattca gctccggttc ccaacgatca    3180
aggcgagtta catgatcccc catgttgtgc aaaaaagcgg ttagctcctt cggtcctccg    3240
atcgttgtca gaagtaagtt ggccgcagtg ttatcactca tggttatggc agcactgcat    3300
aattctctta ctgtcatgcc atccgtaaga tgcttttctg tgactggtga gtactcaacc    3360
aagtcattct gagaatagtg tatgcggcga ccgagttgct cttgcccggc gtcaatacgg    3420
gataataccg cgccacatag cagaacttta aaagtgctca tcattggaaa acgttcttcg    3480
gggcgaaaac tctcaaggat cttaccgctg ttgagatcca gttcgatgta acccactcgt    3540
gcacccaact gatcttcagc atcttttact ttcaccagcg tttctgggtg agcaaaaaca    3600
ggaaggcaaa atgccgcaaa aaagggaata agggcgacac ggaaatgttg aatactcata    3660
ctcttccttt ttcaatatta ttgaagcatt tatcagggtt attgtctcat gagcggatac    3720
atatttgaat gtatttagaa aaataaacaa ataggggttc cgcgcacatt tccccgaaaa    3780
gtgccaccta aattgtaagc gttaatattt tgttaaaatt cgcgttaaat ttttgttaaa    3840
tcagctcatt ttttaaccaa taggccgaaa tcggcaaaat cccttataaa tcaaaagaat    3900
agaccgagat agggttgagt gttgttccag tttggaacaa gagtccacta ttaaagaacg    3960
tggactccaa cgtcaaaggg cgaaaaaccg tctatcaggg cgatggccca ctacgtgaac    4020
catcacccta atcaagtttt tggggtcgag gtgccgtaa agcactaaat cggaacccta    4080
aagggagccc ccgatttaga gcttgacggg gaaagccggc gaacgtggcg agaaaggaag    4140
ggaagaaagc gaaaggagcg ggcgctaggg cgctggcaag tgtagcggtc acgctgcgcg    4200
taaccaccac acccgccgcg cttaatgcgc cgctacaggg cgcgtcccat tcgccattca    4260
ggctgcgcaa ctgttgggaa gggcgatcgg tgcgggcctc ttcgctatta cgccagtcga    4320
ccatagccaa ttcaatatgg cgtatatgga ctcatgccaa ttcaatatgg tggatctgga    4380
cctgtgccaa ttcaatatgg cgtatatgga ctcgtgccaa ttcaatatgg tggatctgga    4440
ccccagccaa ttcaatatgg cggacttggc accatgccaa ttcaatatgg cggacttggc    4500
actgtgccaa ctggggaggg gtctacttgg cacggtgcca gtttgagga ggggtcttgg    4560 ccctgtgcca agtccgccat attgaattgg catggtgcca ataatggcgg ccatattggc    4620
tatatgccag gatcaatata taggcaatat ccaatatggc cctatgccaa tatgctatt    4680 ggccaggttc aatactatgt attggcccta tgccatatag tattccatat atgggttttc    4740
ctattgacgt agatagcccc tcccaatggg cggtcccata taccatatat ggggcttcct    4800
aataccgccc atagccactc ccccattgac gtcaatggtc tctatatatg gtctttccta    4860
ttgacgtcat atgggcggtc ctattgacgt atatggcgcc tccccattg acgtcaatta    4920 cggtaaatgg cccgcctggc tcaatgccca ttgacgtca taggaccacc caccattgac    4980
gtcaatggga tggctcattg cccattcata tccgttctca cgcccctat tgacgtcaat    5040
```

| | | |
|---|---|---|
| gacggtaaat ggcccacttg gcagtacatc aatatctatt aatagtaact tggcaagtac | 5100 | |
| attactattg gaaggacgcc agggtacatt ggcagtactc ccattgacgt caatggcggt | 5160 | |
| aaatggcccg cgatggctgc caagtacatc cccattgacg tcaatgggga ggggcaatga | 5220 | |
| cgcaaatggg cgttccattg acgtaaatgg cggtaggcg tgcctaatgg gaggtctata | 5280 | |
| taagcaatgc tcgtttaggg aac | 5303 | |

<210> SEQ ID NO 8
<211> LENGTH: 5948
<212> TYPE: DNA
<213> ORGANISM: Artificial Sequence
<220> FEATURE:
<223> OTHER INFORMATION: pTac2-VP64

<400> SEQUENCE: 8

| | |
|---|---|
| cgccattctg cctggggacg tcggagcaag cttgatttag gtgacactat agaatacaag | 60 |
| ctacttgttc tttttgcaag atctccacca tggactataa ggaccacgac ggagactaca | 120 |
| aggatcatga tattgattac aaagacgatg acgataagat ggccccaaag aagaagcgga | 180 |
| aggtcggtat ccccgggtcc ctgaacgact ttgcactggt cttaaggaa ttcgcaggaa | 240 |
| gggggggattg gcaaagatcc ctgagactgt taagtatat gcagaggcaa atctggtgca | 300 |
| aacccaatga gcatatctat accattatga tttccctgct ggggagagaa ggactgctgg | 360 |
| ataaatgtct ggaagtgttt gacgaaatgc ttcccaagg agtgagcagg agcgtgttca | 420 |
| gctacactgc actgattaac gcctacggca gaaacggcag gtacgaaact agcctggagc | 480 |
| tgctggacag aatgaaaaac gagaagatca gcccaagcat cctgacttat aacacagtga | 540 |
| tcaatgcttg tgccagaggc ggactggact gggagggcct gctgggcctg ttcgcagaga | 600 |
| tgaggcacga agggattcaa cccgacatcg tgacttacaa tactctgctg tccgcatgtg | 660 |
| caattagggg cctgggggac gaagctgaaa tggtcttcag gactatgaat gacggcggaa | 720 |
| tcgtgcccga tctgaccaca tattcccatc tggtcgagac ctttgggaaa ctgaggagac | 780 |
| tggagaaggt gtgcgatctg ctgggagaaa tggctagcgg aggctcccctg ccagatatta | 840 |
| cctcctacaa cgtgctgctg gaagcctacg ccaagtccgg ctccatcaag gaggctatgg | 900 |
| gcgtgttca tcagatgcaa gccgctggct gtacccccaa tgccaacacc tattccgtcc | 960 |
| tgctgaatct gttcggccag agcgggagat acgatgacgt gaggcagctg tttctggaaa | 1020 |
| tgaagagcag caacaccgac cccgacgctg caacatacaa cattctgatc gaggtgtttg | 1080 |
| gcgaggggg ctacttcaaa gaagtcgtca ccctgttcca cgacatggtg gaggaaaaca | 1140 |
| tcgagcccga tatggagacc tatgagggga tcatcttcgc ttgcggcaaa ggcggcctgc | 1200 |
| atgaggacgc taggaagatc ctgcagtaca tgaccgctaa tgacattgtc ccatcctcca | 1260 |
| aagcttatac cggcgtgatc gaggccttcg gccaggctgc cctgtacgag aagcactgg | 1320 |
| tcgcctttaa caccatgcac gaggtcggca gcaaccctc catcgagacc ttccactccc | 1380 |
| tgctgtatag cttcgccaga ggcgggctgg tgaaggagtc cgaggcaatc ctgagcaggc | 1440 |
| tggtcgattc cggcatcccc aggaacagag acacctttaa tgctcaaatt gaggcctaca | 1500 |
| aacagggggg gaagttcgaa gaggctgtga agacctacgt cgacatggaa aagagcaggt | 1560 |
| gcgaccccga cgagaggacc ctggaggccg tcctgtccgt gtattccttc gcaagactgg | 1620 |
| tggatgagtg cagggaacag tttgaagaaa tgaaggccag cgacattctg cccagcatta | 1680 |
| tgtgctactg catgatgctg gcagtgtacg ggaagaccga gaggtgggac gacgtgaacg | 1740 |

```
aactgctgga ggagatgctg agcaacaggg tcagcaacgg atccggacgg gctgacgcat    1800
tggacgattt tgatctggat atgctgggaa gtgacgccct cgatgatttt gaccttgaca    1860
tgcttggttc ggatgccctt gatgactttg acctcgacat gctcggcagt gacgcccttg    1920
atgatttcga cctggacatg ctgattaact ctagttgatc tagattctgc agccctatag    1980
tgagtcgtat tacgtagatc cagacatgat aagatacatt gatgagtttg acaaaccac     2040 aactagaatg cagtgaaaaa aatgctttat ttgtgaaatt tgtgatgcta ttgctttatt    2100
tgtaaccatt ataagctgca ataaacaagt taacaacaac aattgcattc attttatgtt    2160
tcaggttcag ggggaggtgt gggaggtttt ttaattcgcg ccgcggcgc caatgcattg     2220 ggcccggtac ccagcttttg ttcccttttag tgagggttaa ttgcgcgctt ggcgtaatca   2280
tggtcatagc tgtttcctgt gtgaaattgt tatccgctca caattccaca acatacga     2340 gccggaagca taaagtgtaa agcctggggt gcctaatgag tgagctaact cacattaatt   2400
gcgttgcgct cactgcccgc tttccagtcg ggaaacctgt cgtgccagct gcattaatga   2460
atcggccaac gcgcgggag aggcggtttg cgtattgggc gctcttccgc ttcctcgctc    2520
actgactcgc tgcgctcggt cgttcggctg cggcgagcgg tatcagctca ctcaaaggcg   2580
gtaatacggt tatccacaga atcaggggat aacgcaggaa agaacatgtg agcaaaaggc   2640
cagcaaaagg ccaggaaccg taaaaaggcc gcgttgctgg cgtttttcca taggctccgc   2700 cccccctgacg agcatcacaa aaatcgacgc tcaagtcaga ggtggcgaaa cccgacagga   2760
ctataaagat accaggcgtt tccccctgga agctccctcg tgcgctctcc tgttccgacc   2820
ctgccgctta ccggatacct gtccgccttt ctcccttcgg gaagcgtggc gctttctcat   2880
agctcacgct gtaggtatct cagttcggtg taggtcgttc gctccaagct gggctgtgtg   2940
cacgaacccc ccgttcagcc cgaccgctgc gccttatccg gtaactatcg tcttgagtcc   3000
aacccggtaa gacacgactt atcgccactg gcagcagcca ctggtaacag gattagcaga   3060
gcgaggtatg taggcggtgc tacagagttc ttgaagtggt ggcctaacta cggctacact   3120
agaaggacag tatttggtat ctgcgctctg ctgaagccag ttaccttcgg aaaaagagtt   3180
ggtagctctt gatccggcaa acaaaccacc gctggtagcg gtggtttttt tgtttgcaag   3240
cagcagatta cgcgcagaaa aaaaggatct caagaagatc ctttgatctt ttctacgggg   3300
tctgacgctc agtggaacga aaactcacgt taagggattt tggtcatgag attatcaaaa   3360
aggatcttca cctagatcct tttaaattaa aaatgaagtt ttaaatcaat ctaaagtata   3420
tatgagtaaa cttggtctga cagttaccaa tgcttaatca gtgaggcacc tatctcagcg   3480
atctgtctat ttcgttcatc catagttgcc tgactccccg tcgtgtagat aactacgata   3540
cgggagggct taccatctgg ccccagtgct gcaatgatac cgcgagaccc acgctcaccg   3600
gctccagatt tatcagcaat aaaccagcca gccggaaggg ccgagcgcag aagtggtcct   3660
gcaactttat ccgcctccat ccagtctatt aattgttgcc gggaagctag agtaagtagt   3720
tcgccagtta atagtttgcg caacgttgtt gccattgcta caggcatcgt ggtgtcacgc   3780
tcgtcgtttg gtatggcttc attcagctcc ggttcccaac gatcaaggcg agttacatga   3840
tcccccatgt tgtgcaaaaa agcggttagc tccttcggtc ctccgatcgt tgtcagaagt   3900
aagttggccg cagtgttatc actcatggtt atggcagcac tgcataattc tcttactgtc   3960
atgccatccg taagatgctt ttctgtgact ggtgagtact caaccaagtc attctgagaa   4020
tagtgtatgc ggcgaccgag ttgctcttgc ccggcgtcaa tacgggataa taccgcgcca   4080
catagcagaa ctttaaaagt gctcatcatt ggaaaacgtt cttcggggcg aaaactctca   4140
```

-continued

```
aggatcttac cgctgttgag atccagttcg atgtaaccca ctcgtgcacc caactgatct    4200
tcagcatctt ttactttcac cagcgtttct gggtgagcaa aaacaggaag gcaaaatgcc    4260
gcaaaaaagg gaataagggc gacacggaaa tgttgaatac tcatactctt ccttttcaa     4320
tattattgaa gcatttatca gggttattgt ctcatgagcg gatacatatt tgaatgtatt    4380
tagaaaaata aacaaatagg ggttccgcgc acatttcccc gaaaagtgcc acctaaattg    4440
taagcgttaa tattttgtta aaattcgcgt taaattttg ttaaatcagc tcatttttta    4500
accaataggc cgaaatcggc aaaatccctt ataaatcaaa agaatagacc gagatagggt    4560
tgagtgttgt tccagtttgg aacaagagtc cactattaaa gaacgtggac tccaacgtca    4620
aagggcgaaa aaccgtctat cagggcgatg gcccactacg tgaaccatca ccctaatcaa    4680
gttttttggg gtcgaggtgc cgtaaagcac taaatcggaa ccctaaaggg agcccccgat    4740
ttagagcttg acggggaaag ccggcgaacg tggcgagaaa ggaagggaag aaagcgaaag    4800
gagcgggcgc tagggcgctg gcaagtgtag cggtcacgct gcgcgtaacc accacacccg    4860
ccgcgcttaa tgcgccgcta cagggcgcgt cccattcgcc attcaggctg cgcaactgtt    4920
gggaagggcg atcggtgcgg gcctcttcgc tattacgcca gtcgaccata gccaattcaa    4980
tatggcgtat atggactcat gccaattcaa tatggtggat ctggacctgt gccaattcaa    5040
tatggcgtat atggactcgt gccaattcaa tatggtggat ctggacccca gccaattcaa    5100
tatggcggac ttggcaccat gccaattcaa tatggcggac ttggcactgt gccaactggg    5160
gaggggtcta cttggcacgg tgccaagttt gaggaggggt cttggccctg tgccaagtcc    5220
gccatattga attggcatgg tgccaataat ggcggccata ttggctatat gccaggatca    5280
atatataggc aatatccaat atggccctat gccaatatgg ctattggcca ggttcaatac    5340
tatgtattgg ccctatgcca tatagtattc catatatggg ttttcctatt gacgtagata    5400
gccctcccca atgggcggtc ccatatacca tatgtgggc ttcctaatac cgcccatagc     5460
cactccccca ttgacgtcaa tggtctctat atatggtctt tcctattgac gtcatatggg    5520
cggtcctatt gacgtatatg cgcctcccc cattgacgtc aattacggta atggcccgc     5580
ctggctcaat gcccattgac gtcaatagga ccacccacca ttgacgtcaa tgggatggct    5640
cattgcccat tcatatccgt tctcacgccc cctattgacg tcaatgacgg taaatggccc    5700
acttggcagt acatcaatat ctattaatag taacttggca agtacattac tattggaagg    5760
acgccagggt acattggcag tactcccatt gacgtcaatg gcggtaaatg gcccgcgatg    5820
gctgccaagt acatccccat tgacgtcaat ggggagggg aatgacgcaa atgggcgttc     5880
cattgacgta atgggcggt aggcgtgcct aatgggaggt ctatataagc aatgctcgtt    5940
tagggaac                                                              5948
```

<210> SEQ ID NO 9
<211> LENGTH: 5531
<212> TYPE: DNA
<213> ORGANISM: Artificial Sequence
<220> FEATURE:
<223> OTHER INFORMATION: GUN1-VP64

<400> SEQUENCE: 9

```
cgccattctg cctggggacg tcggagcaag cttgatttag gtgacactat agaatacaag      60
ctacttgttc ttttttgcaag atctccacca tggactataa ggaccacgac ggagactaca    120
aggatcatga tattgattac aaagacgatg acgataagat ggccccaaag aagaagcgga    180
```

| | |
|---|---|
| aggtcggtat ccccgggcaa ggcaagctgg caagcgccat gatctccacc ctgggcaggt | 240 |
| acggaaaggt gaccattgcc aagaggatct tcgagaccgc cttcgcaggc gggtacggca | 300 |
| acaccgtgta tgcttttcc gccctgatta gcgcatatgg cagaagcggc ctgcacgaag | 360 |
| aggccattag cgtgtttaac agcatgaagg agtatggact gaggcccaac ctggtgacct | 420 |
| acaacgccgt cattgatgct tgcggcaagg gcggcatgga attcaagcag gtggccaagt | 480 |
| tcttcgatga aatgcagagg aacggcgtgc agcctgacag aattacattc aatagcctgc | 540 |
| tggctgtgtg cagcagaggg ggcctgtggg aggcagctag gaatctgttt gacgagatga | 600 |
| ccaatagaag gatcgagcag gacgtgttct cctataatac actgctggac gccatttgta | 660 |
| aaggcgggca aatggacctg gccttcgaaa tcctggccca gatgcccgtc aaaaggatca | 720 |
| tgcccaacgt ggtcagctac tccacagtca tcgacgggtt cgccaaggct ggcaggtttg | 780 |
| atgaagcact gaacctgttc ggggaaatga gatacctggg aatcgccctg gacagggtga | 840 |
| gctacaacac cctgctgagc atctacacta aggtcggcag atccgaggaa gccctggaca | 900 |
| tcctgaggga atggcctcc gtgggcatta agaaggacgt cgtgacatac aatgccctgc | 960 |
| tgggcggcta cggcaaacag ggcaagtacg acgaggtcaa gaaggtcttc acagagatga | 1020 |
| agagggaaca cgtgctgcca aatctgctga cttattccac tctgattgat ggctactcca | 1080 |
| aaggcggact gtacaaggaa gccatggaga ttttcagaga gttcaagagc ctggcctga | 1140 |
| gagccgatgt cgtgctgtat tccgcactga tcgatgcact gtgcaaaaac ggcctggtcg | 1200 |
| gcagcgccgt gagcctgatc gacgagatga ccaaggaggg aattagcccc aatgtggtga | 1260 |
| cttacaatag catcattgat gctttcggca gaagcgccac catggacaga tccgccgact | 1320 |
| atagcaacgg cggcagcctg ccatttcct ccagcgccct gggatccgga cgggctgacg | 1380 |
| cattggacga ttttgatctg gatatgctgg gaagtgacgc cctcgatgat tttgaccttg | 1440 |
| acatgcttgg ttcggatgcc cttgatgact ttgacctcga catgctcggc agtgacgccc | 1500 |
| ttgatgattt cgacctggac atgctgatta actctagttg atctagattc tgcagcccta | 1560 |
| tagtgagtcg tattacgtag atccagacat gataagatac attgatgagt ttggacaaac | 1620 |
| cacaactaga atgcagtgaa aaaaatgctt tatttgtgaa atttgtgatg ctattgcttt | 1680 |
| atttgtaacc attataagct gcaataaaca agttaacaac aacaattgca ttcattttat | 1740 |
| gtttcaggtt caggggagg tgtgggaggt tttttaattc gcggccgcgg cgccaatgca | 1800 |
| ttgggcccgg tacccagctt ttgttccctt tagtgagggt taattgcgcg cttggcgtaa | 1860 |
| tcatggtcat agctgtttcc tgtgtgaaat tgttatccgc tcacaattcc acacaacata | 1920 |
| cgagccggaa gcataaagtg taaagcctgg ggtgcctaat gagtgagcta actcacatta | 1980 |
| attgcgttgc gctcactgcc cgcttttcag tcgggaaacc tgtcgtgcca gctgcattaa | 2040 |
| tgaatcggcc aacgcgcggg gagaggcggt ttgcgtattg ggcgctcttc cgcttcctcg | 2100 |
| ctcactgact cgctgcgctc ggtcgttcgg ctgcggcgag cggtatcagc tcactcaaag | 2160 |
| gcggtaatac ggttatccac agaatcaggg gataacgcag gaaagaacat gtgagcaaaa | 2220 |
| ggccagcaaa aggccaggaa ccgtaaaaag gccgcgttgc tggcgttttt ccataggctc | 2280 |
| cgcccccctg acgagcatca aaaaatcga cgctcaagtc agaggtggcg aaacccgaca | 2340 |
| ggactataaa gataccaggc gtttccccct ggaagctccc tcgtgcgctc tcctgttccg | 2400 |
| accctgccgc ttaccggata cctgtccgcc tttctccctt cgggaagcgt ggcgctttct | 2460 |
| catagctcac gctgtaggta tctcagttcg gtgtaggtcg ttcgctccaa gctgggctgt | 2520 |
| gtgcacgaac cccccgttca gcccgaccgc tgcgccttat ccggtaacta tcgtcttgag | 2580 |

```
tccaacccgg taagacacga cttatcgcca ctggcagcag ccactggtaa caggattagc    2640
agagcgaggt atgtaggcgg tgctacagag ttcttgaagt ggtggcctaa ctacggctac    2700
actagaagga cagtatttgg tatctgcgct ctgctgaagc cagttacctt cggaaaaaga    2760
gttggtagct cttgatccgg caaacaaacc accgctggta gcggtggttt ttttgtttgc    2820
aagcagcaga ttacgcgcag aaaaaaagga tctcaagaag atcctttgat cttttctacg    2880
gggtctgacg ctcagtggaa cgaaaactca cgttaaggga ttttggtcat gagattatca    2940
aaaaggatct cacctagatc cttttaaatt aaaaatgaag ttttaaatca atctaaagt     3000 atatatgagt aaacttggtc tgacagttac caatgcttaa tcagtgaggc acctatctca    3060
gcgatctgtc tatttcgttc atccatagtt gcctgactcc ccgtcgtgta gataactacg    3120
atacgggagg gcttaccatc tggccccagt gctgcaatga taccgcgaga cccacgctca    3180
ccggctccag atttatcagc aataaaccag ccagccggaa gggccgagcg cagaagtggt    3240
cctgcaactt tatccgcctc catccagtct attaattgtt gccgggaagc tagagtaagt    3300
agttcgccag ttaatagttt gcgcaacgtt gttgccattg ctacaggcat cgtggtgtca    3360
cgctcgtcgt ttggtatggc ttcattcagc tccggttccc aacgatcaag gcgagttaca    3420
tgatccccca tgttgtgcaa aaaagcggtt agctccttcg gtcctccgat cgttgtcaga    3480
agtaagttgg ccgcagtgtt atcactcatg gttatggcag cactgcataa ttctcttact    3540
gtcatgccat ccgtaagatg cttttctgtg actggtgagt actcaaccaa gtcattctga    3600
gaatagtgta tgcggcgacc gagttgctct tgcccggcgt caatacggga taataccgcg    3660
ccacatagca gaactttaaa agtgctcatc attggaaaac gttcttcggg gcgaaaactc    3720
tcaaggatct taccgctgtt gagatccagt tcgatgtaac ccactcgtgc acccaactga    3780
tcttcagcat cttttacttt caccagcgtt tctgggtgag caaaaacagg aaggcaaaat    3840
gccgcaaaaa agggaataag ggcgacacgg aaatgttgaa tactcatact cttcctttt     3900 caatattatt gaagcattta tcagggttat tgtctcatga gcggatacat atttgaatgt    3960
atttagaaaa ataaacaaat aggggttccg cgcacatttc cccgaaaagt gccacctaaa    4020
ttgtaagcgt taatattttg ttaaaattcg cgttaaattt ttgttaaatc agctcatttt    4080
ttaaccaata ggccgaaatc ggcaaaatcc cttataaatc aaaagaatag accgagatag    4140
ggttgagtgt tgttccagtt tggaacaaga gtccactatt aaagaacgtg gactccaacg    4200
tcaaagggcg aaaaaccgtc tatcagggcg atggcccact acgtgaacca tcaccctaat    4260 caagttttt gggtcgagg tgccgtaaag cactaaatcg gaaccctaaa gggagccccc     4320
gatttagagc ttgacgggga agccggcga acgtggcgag aaaggaaggg aagaaagcga    4380
aaggagcggc gctagggcg ctggcaagtg tagcggtcac gctgcgcgta accaccacac    4440
ccgccgcgct taatgcgccg ctacagggcg cgtcccattc gccattcagg ctgcgcaact    4500
gttgggaagg gcgatcggtg cgggcctctt cgctattacg ccagtcgacc atagccaatt    4560
caatatggcg tatatggact catgccaatt caatatggtg gatctggacc tgtgccaatt    4620
caatatggcg tatatggact cgtgccaatt caatatggtg gatctggacc ccagccaatt    4680
caatatggcg gacttggcac catgccaatt caatatggcg gacttggcac tgtgccaact    4740
ggggaggggt ctacttggca cggtgccaag tttgaggagg ggtcttggcc ctgtgccaag    4800
tccgccatat tgaattggca tggtgccaat aatggcggcc atattggcta tatgccagga    4860
tcaatatata ggcaatatcc aatatggccc tatgccaata tggctattgg ccaggttcaa    4920
```

```
tactatgtat tggccctatg ccatatagta ttccatatat gggttttcct attgacgtag    4980
atagcccctc ccaatgggcg gtcccatata ccatatatgg ggcttcctaa taccgcccat    5040
agccactccc ccattgacgt caatggtctc tatatatggt ctttcctatt gacgtcatat    5100
gggcggtcct attgacgtat atggcgcctc cccattgac gtcaattacg gtaaatggcc    5160
cgcctggctc aatgcccatt gacgtcaata ggaccaccca ccattgacgt caatgggatg    5220
gctcattgcc cattcatatc cgttctcacg cccctattg acgtcaatga cggtaaatgg    5280
cccacttggc agtacatcaa tatctattaa tagtaacttg gcaagtacat tactattgga    5340
aggacgccag ggtacattgg cagtactccc attgacgtca atggcggtaa atgcccgcg    5400 atggctgcca agtacatccc cattgacgtc aatggggagg gcaatgacg caaatgggcg    5460 ttccattgac gtaaatgggc ggtaggcgtg cctaatggga ggtctatata agcaatgctc    5520
gtttagggaa c                                                        5531

<210> SEQ ID NO 10
<211> LENGTH: 5135
<212> TYPE: DNA
<213> ORGANISM: Artificial Sequence
<220> FEATURE:
<223> OTHER INFORMATION: pminCMV-luc2

<400> SEQUENCE: 10
ggtaccgagc tcttacgcgt gctagcccgg gctcgagatc tgatatcaag cttactagtg      60
tcgaggtagg cgtgtacggt gggaggccta tataagcaga gctcgtttag tgaaccgtca    120
gatcgcctgg aggtaccgcc accatggaag atgccaaaaa cattaagaag ggcccagcgc    180
cattctaccc actcgaagac gggaccgccg gcgagcagct gcacaaagcc atgaagcgct    240
acgccctggt gccggcacc atcgccttta ccgacgcaca tatcgaggtg gacattacct    300
acgccgagta cttcgagatg agcgttcggc tggcagaagc tatgaagcgc tatgggctga    360
atacaaacca tcggatcgtg gtgtgcagcg agaatagctt gcagttcttc atgcccgtgt    420
tgggtgccct gttcatcggt gtggctgtgg ccccagctaa cgacatctac aacgagcgcg    480
agctgctgaa cagcatgggc atcagccagc ccaccgtcgt attcgtgagc aagaaagggc    540
tgcaaaagat cctcaacgtg caaaagaagc taccgatcat acaaaagatc atcatcatgg    600
atagcaagac cgactaccag ggcttccaaa gcatgtacac cttcgtgact tcccatttgc    660
cacccggctt caacgagtac gacttcgtgc ccgagagctt cgaccgggac aaaaccatcg    720
ccctgatcat gaacagtagt ggcagtaccg gattgcccaa gggcgtagcc ctaccgcacc    780
gcaccgcttg tgtccgattc agtcatgccc gcgaccccat cttcggcaac cagatcatcc    840
ccgacaccgc tatcctcagc gtggtgccat tcaccacgg cttcggcatg ttcaccacgc    900
tgggctactt gatctgcggc tttcgggtcg tgctcatgta ccgcttcgag gaggagctat    960
tcttgcgcag cttgcaagac tataagattc aatctgccct gctggtgccc acactattta    1020
gcttcttcgc taagagcact ctcatcgaca gtacgacct aagcaacttg cacgagatcg    1080
ccagcggcgg ggcgccgctc agcaaggagg taggtgaggc cgtggccaaa cgcttccacc    1140
taccaggcat ccgccaggc tacggcctga cagaaacaac cagcgccatt ctgatcaccc    1200
ccgaagggga cgacaagcct ggcgcagtag gcaaggtggt gcccttcttc gaggctaagg    1260
tggtggactt ggacaccggt aagacactgg gtgtgaacca gcgcggcgag ctgtgcgtcc    1320
gtggccccat gatcatgagc ggctacgtta acaaccccga ggctacaaac gctctcatcg    1380
acaaggacgg ctggctgcac agcggcgaca tcgcctactg ggacgaggac gagcacttct    1440
```

```
tcatcgtgga ccggctgaag agcctgatca aatacaaggg ctaccaggta gccccagccg    1500
aactggagag catcctgctg caacacccca acatcttcga cgccgggtc gccggcctgc    1560 ccgacgacga tgccggcgag ctgcccgccg cagtcgtcgt gctggaacac ggtaaaacca    1620
tgaccgagaa ggagatcgtg gactatgtgg ccagccaggt tacaaccgcc aagaagctgc    1680
gcggtggtgt tgtgttcgtg gacgaggtgc ctaaaggact gaccggcaag ttggacgccc    1740
gcaagatccg cgagattctc attaaggcca agaagggcgg caagatcgcc gtgaattctt    1800
aactgcagtt aatctagagt cggggcggcc ggccgcttcg agcagacatg ataagataca    1860
ttgatgagtt tggacaaacc acaactagaa tgcagtgaaa aaaatgcttt atttgtgaaa    1920
tttgtgatgc tattgcttta tttgtaacca ttataagctg caataaacaa gttaacaaca    1980
acaattgcat tcattttatg tttcaggttc agggggaggt gtgggaggtt ttttaaagca    2040
agtaaaacct ctacaaatgt ggtaaaatcg ataaggatct gaacgatgga gcggagaatg    2100
ggcggaactg ggcggagtta ggggcgggat gggcggagtt aggggcggga ctatggttgc    2160
tgactaattg agatgcatgc tttgcatact tctgcctgct ggggagcctg ggactttcc    2220 acacctggtt gctgactaat tgagatgcat gctttgcata cttctgcctg ctggggagcc    2280
tggggacttt ccacacccta actgacacac attccacagc ggatccgtcg accgatgccc    2340
ttgagagcct caacccagt cagctccttc cggtgggcgc ggggcatgac tatcgtcgcc    2400
gcacttatga ctgtcttctt tatcatgcaa ctcgtaggac aggtgccggc agcgctcttc    2460
cgcttcctcg ctcactgact cgctgcgctc ggtcgttcgg ctgcggcgag cggtatcagc    2520
tcactcaaag gcggtaatac ggttatccac agaatcaggg gataacgcag gaaagaacat    2580
gtgagcaaaa ggccagcaaa aggccaggaa ccgtaaaaag gccgcgttgc tggcgttttt    2640
ccataggctc cgcccccctg acgagcatca aaaaatcga cgctcaagtc agaggtggcg    2700
aaacccgaca ggactataaa gataccaggc gtttccccct ggaagctccc tcgtgcgctc    2760
tcctgttccg accctgccgc ttaccggata cctgtccgcc tttctccctt cgggaagcgt    2820
ggcgctttct catagctcac gctgtaggta tctcagttcg gtgtaggtcg ttcgctccaa    2880
gctgggctgt gtgcacgaac ccccgttca gcccgaccgc tgcgccttat ccggtaacta    2940
tcgtcttgag tccaacccgg taagacacga cttatcgcca ctggcagcag ccactggtaa    3000
caggattagc agagcgaggt atgtaggcgg tgctacagag ttcttgaagt ggtggcctaa    3060
ctacggctac actagaagaa cagtatttgg tatctgcgct ctgctgaagc cagttacctt    3120
cggaaaaaga gttggtagct cttgatccgg caaacaaacc accgctggta gcggtggttt    3180
ttttgtttgc aagcagcaga ttacgcgcag aaaaaaagga tctcaagaag atcctttgat    3240
cttttctacg gggtctgacg ctcagtggaa cgaaaactca cgttaaggga ttttggtcat    3300
gagattatca aaaaggatct tcacctagat ccttttaaat taaaaatgaa gttttaaatc    3360
aatctaaagt atatatgagt aaacttggtc tgacagttac caatgcttaa tcagtgaggc    3420
acctatctca gcgatctgtc tatttcgttc atccatagtt gcctgactcc ccgtcgtgta    3480
gataactacg atacgggagg gcttaccatc tggccccagt gctgcaatga taccgcgaga    3540
cccacgctca ccggctccag atttatcagc aataaaccag ccagccggaa gggccgagcg    3600
cagaagtggt cctgcaactt tatccgcctc catccagtct attaattgtt gccgggaagc    3660
tagagtaagt agttcgccag ttaatagttt gcgcaacgtt gttgccattg ctacaggcat    3720
cgtggtgtca cgctcgtcgt ttggtatggc ttcattcagc tccggttccc aacgatcaag    3780
```

```
gcgagttaca tgatccccca tgttgtgcaa aaaagcggtt agctccttcg gtcctccgat    3840
cgttgtcaga agtaagttgg ccgcagtgtt atcactcatg gttatggcag cactgcataa    3900
ttctcttact gtcatgccat ccgtaagatg cttttctgtg actggtgagt actcaaccaa    3960
gtcattctga gaatagtgta tgcggcgacc gagttgctct tgcccggcgt caatacggga    4020
taataccgcg ccacatagca gaactttaaa agtgctcatc attggaaaac gttcttcggg    4080
gcgaaaactc tcaaggatct taccgctgtt gagatccagt tcgatgtaac ccactcgtgc    4140
acccaactga tcttcagcat cttttacttt caccagcgtt tctgggtgag caaaaacagg    4200
aaggcaaaat gccgcaaaaa agggaataag ggcgacacgg aaatgttgaa tactcatact    4260 cttcctttt caatattatt gaagcattta tcagggttat tgtctcatga gcggatacat    4320
atttgaatgt atttagaaaa ataaacaaat aggggttccg cgcacatttc cccgaaaagt    4380
gccacctgac gcgcctgta gcggcgcatt aagcgcggcg ggtgtggtgg ttacgcgcag    4440
cgtgaccgct acacttgcca gcgccctagc gcccgctcct ttcgctttct tcccttcctt    4500
tctcgccacg ttcgccggct ttccccgtca agctctaaat cggggctcc ctttagggtt    4560 ccgatttagt gctttacggc acctcgaccc caaaaaactt gattagggtg atggttcacg    4620
tagtgggcca tcgccctgat agacggtttt tcgccctttg acgttggagt ccacgttctt    4680
taatagtgga ctcttgttcc aaactggaac aacactcaac cctatctcgg tctattcttt    4740
tgatttataa gggattttgc cgatttcggc ctattggtta aaaaatgagc tgatttaaca    4800
aaaatttaac gcgaattta acaaaatatt aacgcttaca atttgccatt cgccattcag    4860
gctgcgcaac tgttgggaag ggcgatcggt gcgggcctct tcgctattac gccagcccaa    4920
gctaccatga taagtaagta atattaaggt acgggaggta cttggagcgg ccgcaataaa    4980
atatctttat tttcattaca tctgtgtgtt ggttttttgt gtgaatcgat agtactaaca    5040
tacgctctcc atcaaaacaa aacgaaacaa aacaaactag caaaataggc tgtccccagt    5100
gcaagtgcag gtgccagaac atttctctat cgata                               5135

<210> SEQ ID NO 11
<211> LENGTH: 9
<212> TYPE: DNA
<213> ORGANISM: Artificial Sequence
<220> FEATURE:
<223> OTHER INFORMATION: Target sequence in p63

<400> SEQUENCE: 11 tctatcact                                                              9

<210> SEQ ID NO 12
<211> LENGTH: 15
<212> TYPE: DNA
<213> ORGANISM: Artificial Sequence
<220> FEATURE:
<223> OTHER INFORMATION: Target sequence in pTac2

<400> SEQUENCE: 12
aactttcgtc actca                                                      15

<210> SEQ ID NO 13
<211> LENGTH: 11
<212> TYPE: DNA
<213> ORGANISM: Artificial Sequence
<220> FEATURE:
<223> OTHER INFORMATION: Target sequence in GUN1

<400> SEQUENCE: 13
```
aatttgtcga t    11

<210> SEQ ID NO 14
<211> LENGTH: 5204
<212> TYPE: DNA
<213> ORGANISM: Artificial Sequence
<220> FEATURE:
<223> OTHER INFORMATION: p63-4x target

<400> SEQUENCE: 14

```
ggtaccgagc tcttacgcgt gctagcccgg gctcgagatc tgatatcaag ttctatcact      60
ttgtttcttc tatcacttga attcttctat cacttatctt cttctatcac ttcagttcgc     120
ttactagtgt cgaggtaggc gtgtacggtg ggaggcctat ataagcagag ctcgtttagt     180
gaaccgtcag atcgcctgga ggtaccgcca ccatggaaga tgccaaaaac attaagaagg     240
gcccagcgcc attctaccca ctcgaagacg ggaccgccgg cgagcagctg cacaaagcca     300
tgaagcgcta cgccctggtg ccggcacca tcgcctttac cgacgcacat atcgaggtgg     360
acattaccta cgccgagtac ttcgagatga gcgttcggct ggcagaagct atgaagcgct     420
atgggctgaa tacaaaccat cggatcgtgg tgtgcagcga aatagcttg cagttcttca     480
tgcccgtgtt gggtgccctg ttcatcggtg tggctgtggc cccagctaac gacatctaca     540
acgagcgcga gctgctgaac agcatgggca tcagccagcc caccgtcgta ttcgtgagca     600
agaaagggct gcaaaagatc ctcaacgtgc aaaagaagct accgatcata caaaagatca     660
tcatcatgga tagcaagacc gactaccagg gcttccaaag catgtacacc ttcgtgactt     720
cccatttgcc acccggcttc aacgagtacg acttcgtgcc cgagagcttc gaccgggaca     780
aaaccatcgc cctgatcatg aacagtagtg gcagtaccgg attgcccaag gcgtagccc     840
taccgcaccg caccgcttgt gtccgattca gtcatgcccg cgaccccatc ttcggcaacc     900
agatcatccc cgacaccgct atcctcagcg tggtgccatt tcaccacggc ttcggcatgt     960
tcaccacgct gggctacttg atctgcggct ttcgggtcgt gctcatgtac cgcttcgagg    1020
aggagctatt cttgcgcagc ttgcaagact ataagattca atctgccctg ctggtgccca    1080
cactatttag cttcttcgct aagagcactc tcatcgacaa gtacgaccta agcaacttgc    1140
acgagatcgc cagcggcggg cgccgctca gcaaggaggt aggtgaggcc gtggccaaac    1200
gcttccacct accaggcatc cgccaggct acggcctgac agaaacaacc agcgccattc    1260
tgatcacccc cgaaggggac gacaagcctg cgcagtagg caaggtggtg cccttcttcg    1320
aggctaaggt ggtggacttg gacaccggta agacactggg tgtgaaccag cgcggcgagc    1380
tgtgcgtccg tggccccatg atcatgagcg gctacgttaa caaccccgag ctacaaacg    1440
ctctcatcga caaggacggc tggctgcaca gcggcgacat cgcctactgg gacgaggacg    1500
agcacttctt catcgtggac cggctgaaga gcctgatcaa atacaagggc taccaggtag    1560
ccccagccga actggagagc atcctgctgc aacaccccaa catcttcgac gccgggtcg    1620
ccggcctgcc cgacgacgat gccggcgagc tgcccgccgc agtcgtcgtg ctggaacacg    1680
gtaaaaccat gaccgagaag gagatcgtgg actatgtggc cagccaggtt acaaccgcca    1740
agaagctgcg cggtggtgtt gtgttcgtgg acgaggtgcc taaggactg accggcaagt    1800
tggacgcccg caagatccgc gagattctca ttaaggccaa gaagggcggc aagatcgccg    1860
tgaattctta actgcagtta atctagagtc ggggcggccg ccgcttcga gcagacatga    1920
taagatacat tgatgagttt ggacaaacca caactagaat gcagtgaaaa aaatgcttta    1980
```

```
tttgtgaaat ttgtgatgct attgctttat ttgtaaccat tataagctgc aataaacaag    2040
ttaacaacaa caattgcatt cattttatgt ttcaggttca gggggaggtg tgggaggttt    2100
tttaaagcaa gtaaaacctc tacaaatgtg gtaaaatcga taaggatctg aacgatggag    2160
cggagaatgg gcggaactgg gcggagttag gggcgggatg ggcggagtta ggggcgggac    2220
tatggttgct gactaattga gatgcatgct ttgcatactt ctgcctgctg gggagcctgg    2280
ggactttcca cacctggttg ctgactaatt gagatgcatg cttttgcatac ttctgcctgc    2340 tggggagcct ggggactttc cacaccctaa ctgacacaca ttccacagcg gatccgtcga    2400
ccgatgccct tgagagcctt caacccagtc agctccttcc ggtgggcgcg gggcatgact    2460
atcgtcgccg cacttatgac tgtcttcttt atcatgcaac tcgtaggaca ggtgccggca    2520
gcgctcttcc gcttcctcgc tcactgactc gctgcgctcg gtcgttcggc tgcggcgagc    2580
ggtatcagct cactcaaagg cggtaatacg gttatccaca gaatcagggg ataacgcagg    2640
aaagaacatg tgagcaaaag gccagcaaaa ggccaggaac cgtaaaaagg ccgcgttgct    2700
ggcgtttttc cataggctcc gcccccctga cgagcatcac aaaaatcgac gctcaagtca    2760
gaggtggcga aacccgacag gactataaag ataccaggcg tttccccctg gaagctccct    2820
cgtgcgctct cctgttccga ccctgccgct taccggatac ctgtccgcct ttctcccttc    2880
gggaagcgtg cgctttctc atagctcacg ctgtaggtat ctcagttcgg tgtaggtcgt    2940
tcgctccaag ctgggctgtg tgcacgaacc ccccgttcag cccgaccgct gcgccttatc    3000
cggtaactat cgtcttgagt ccaacccggt aagacacgac ttatcgccac tggcagcagc    3060
cactggtaac aggattagca gagcgaggta tgtaggcggt gctacagagt tcttgaagtg    3120
gtggcctaac tacggctaca ctagaagaac agtatttggt atctgcgctc tgctgaagcc    3180
agttaccttc ggaaaaagag ttggtagctc ttgatccggc aaacaaacca ccgctggtag    3240
cggtggtttt tttgtttgca agcagcagat tacgcgcaga aaaaaaggat ctcaagaaga    3300
tcctttgatc ttttctacgg ggtctgacgc tcagtggaac gaaaactcac gttaagggat    3360
tttggtcatg agattatcaa aaaggatctt cacctagatc cttttaaatt aaaaatgaag    3420
ttttaaatca atctaaagta tatatgagta aacttggtct gacagttacc aatgcttaat    3480
cagtgaggca cctatctcag cgatctgtct atttcgttca tccatagttg cctgactccc    3540
cgtcgtgtag ataactacga tacgggaggg cttaccatct ggccccagtg ctgcaatgat    3600
accgcgagac ccacgctcac cggctccaga tttatcagca ataaaccagc cagccggaag    3660
ggccgagcgc agaagtggtc ctgcaacttt atccgcctcc atccagtcta ttaattgttg    3720
ccgggaagct agagtaagta gttcgccagt taatagtttg cgcaacgttg ttgccattgc    3780
tacaggcatc gtggtgtcac gctcgtcgtt tggtatggct tcattcagct ccggttccca    3840
acgatcaagg cgagttacat gatccccccat gttgtgcaaa aaagcggtta gctccttcgg    3900
tcctccgatc gttgtcagaa gtaagttggc cgcagtgtta tcactcatgg ttatggcagc    3960
actgcataat tctcttactg tcatgccatc cgtaagatgc ttttctgtga ctggtgagta    4020
ctcaaccaag tcattctgag aatagtgtat gcggcgaccg agttgctctt gcccggcgtc    4080
aatacgggat aataccgcgc cacatagcag aactttaaaa gtgctcatca ttggaaaacg    4140
ttcttcgggg cgaaaactct caaggatctt accgctgttg agatccagtt cgatgtaacc    4200
cactcgtgca cccaactgat cttcagcatc ttttactttc accagcgttt ctgggtgagc    4260
aaaaacagga aggcaaaatg ccgcaaaaaa gggaataagg gcgacacgga aatgttgaat    4320
actcatactc ttcctttttc aatattattg aagcatttat cagggttatt gtctcatgag    4380
```

```
cggatacata tttgaatgta tttagaaaaa taaacaaata gggggttccgc gcacatttcc   4440 ccgaaaagtg ccacctgacg cgccctgtag cggcgcatta agcgcggcgg gtgtggtggt   4500
tacgcgcagc gtgaccgcta cacttgccag cgccctagcg cccgctcctt tcgctttctt   4560
cccttccttt ctcgccacgt tcgccggctt tccccgtcaa gctctaaatc ggggctccc   4620 tttagggttc cgatttagtg ctttacggca cctcgacccc aaaaaacttg attagggtga   4680
tggttcacgt agtgggccat cgccctgata acggtttttt cgcccttga cgttggagtc    4740 cacgttcttt aatagtggac tcttgttcca actggaaca acactcaacc ctatctcggt    4800
ctattctttt gatttataag ggattttgcc gatttcggcc tattggttaa aaatgagct    4860 gatttaacaa aaatttaacg cgaattttaa caaaatatta acgcttacaa tttgccattc   4920
gccattcagg ctgcgcaact gttgggaagg gcgatcggtg cgggcctctt cgctattacg   4980
ccagcccaag ctaccatgat aagtaagtaa tattaaggta cgggaggtac ttggagcggc   5040
cgcaataaaa tatctttatt ttcattacat ctgtgtgttg gttttttgtg tgaatcgata   5100
gtactaacat acgctctcca tcaaaacaaa acgaaacaaa acaaactagc aaaataggct   5160
gtccccagtg caagtgcagg tgccagaaca tttctctatc gata            5204
```

<210> SEQ ID NO 15
<211> LENGTH: 5272
<212> TYPE: DNA
<213> ORGANISM: Artificial Sequence
<220> FEATURE:
<223> OTHER INFORMATION: p63-8x target

<400> SEQUENCE: 15

```
ggtaccgagc tcttacgcgt gctagcccgg gctcgagatc tgatatcaag ttctatcact     60
tccatggttc tatcacttca cgacttctat cactttgttt cttctatcac ttgaattctt    120
ctatcactta agttcttcta tcacttttcg aattctatca cttatcttct tctatcactt    180
cagttcgctt actagtgtcg aggtaggcgt gtacggtggg aggcctatat aagcagagct    240
cgtttagtga accgtcagat cgcctggagg taccgccacc atggaagatg ccaaaaacat    300
taagaagggc ccagcgccat tctacccact cgaagacggg accgccggcg agcagctgca    360
caaagccatg aagcgctacg ccctggtgcc cggcaccatc gcctttaccg acgcacatat    420
cgaggtggac attacctacg ccgagtactt cgagatgagc gttcggctgg cagaagctat    480
gaagcgctat gggctgaata caaaccatcg gatcgtggtg tgcagcgaga atagcttgca    540
gttcttcatg cccgtgttgg gtgccctgtt catcggtgtg gctgtggccc cagctaacga    600
catctacaac gagcgcgagc tgctgaacag catgggcatc agccagccca ccgtcgtatt    660
cgtgagcaag aaagggctgc aaaagatcct caacgtgcaa agaagctac cgatcataca    720 aaagatcatc atcatggata gcaagaccga ctaccagggc ttccaaagca tgtacacctt    780
cgtgacttcc catttgccac ccggcttcaa cgagtacgac ttcgtgcccg agagcttcga    840
ccgggacaaa accatcgccc tgatcatgaa cagtagtggc agtaccggat tgcccaaggg    900
cgtagcccta ccgcaccgca ccgcttgtgt ccgattcagt catgcccgcg acccatctt    960 cggcaaccag atcatccccg acaccgctat cctcagcgtg gtgccatttc accacggctt   1020
cggcatgttc accacgctgg gctacttgat ctgcggcttt cgggtcgtgc tcatgtaccg   1080
cttcgaggag gagctattct tgcgcagctt gcaagactat aagattcaat ctgccctgct   1140
ggtgcccaca ctatttagct tcttcgctaa gagcactctc atcgacaagt acgacctaag   1200
```

```
caacttgcac gagatcgcca gcggcggggc gccgctcagc aaggaggtag gtgaggccgt    1260
ggccaaacgc ttccacctac caggcatccg ccagggctac ggcctgacag aaacaaccag    1320
cgccattctg atcaccccg aaggggacga caagcctggc gcagtaggca aggtggtgcc    1380
```
(Note: line 1320→1380 second group shown as "atcacccccg" in source)

```
caacttgcac gagatcgcca gcggcggggc gccgctcagc aaggaggtag gtgaggccgt    1260
ggccaaacgc ttccacctac caggcatccg ccagggctac ggcctgacag aaacaaccag    1320
cgccattctg atcaccccg aaggggacga caagcctggc gcagtaggca aggtggtgcc    1380
cttcttcgag gctaaggtgg tggacttgga caccggtaag acactgggtg tgaaccagcg    1440
cggcgagctg tgcgtccgtg gccccatgat catgagcggc tacgttaaca ccccgaggc    1500
tacaaacgct ctcatcgaca aggacggctg gctgcacagc ggcgacatcg cctactggga    1560
cgaggacgag cacttcttca tcgtggaccg gctgaagagc ctgatcaaat acaagggcta    1620
ccaggtagcc ccagccgaac tggagagcat cctgctgcaa caccccaaca tcttcgacgc    1680
cggggtcgcc ggcctgcccg acgacgatgc cggcgagctg cccgccgcag tcgtcgtgct    1740
ggaacacggt aaaaccatga ccgagaagga gatcgtggac tatgtggcca gccaggttac    1800
aaccgccaag aagctgcgcg tggtgttgt gttcgtggac gaggtgccta aaggactgac    1860
cggcaagttg gacgcccgca agatccgcga gattctcatt aaggccaaga agggcggcaa    1920
gatcgccgtg aattcttaac tgcagttaat ctagagtcgg gcggccggc cgcttcgagc    1980
agacatgata agatacattg atgagtttgg acaaaccaca actagaatgc agtgaaaaaa    2040
atgctttatt tgtgaaattt gtgatgctat tgctttattt gtaaccatta taagctgcaa    2100
taaacaagtt aacaacaaca attgcattca ttttatgttt caggttcagg gggaggtgtg    2160
ggaggtttt taaagcaagt aaaacctcta caaatgtggt aaaatcgata aggatctgaa    2220
cgatggagcg gagaatgggc ggaactgggc ggagttaggg gcgggatggg cggagttagg    2280
ggcgggacta tggttgctga ctaattgaga tgcatgcttt gcatacttct gcctgctggg    2340
gagcctgggg actttccaca cctggttgct gactaattga gatgcatgct ttgcatactt    2400
ctgcctgctg gggagcctgg ggactttcca caccctaact gacacacatt ccacagcgga    2460
tccgtcgacc gatgcccttg agagccttca acccagtcag ctccttccgg tgggcgcggg    2520
gcatgactat cgtcgccgca cttatgactg tcttctttat catgcaactc gtaggacagg    2580
tgccggcagc gctcttccgc ttcctcgctc actgactcgc tgcgctcggt cgttcggctg    2640
cggcgagcgg tatcagctca ctcaaaggcg gtaatacggt tatccacaga atcaggggat    2700
aacgcaggaa agaacatgtg agcaaaaggc cagcaaaagg ccaggaaccg taaaaaggcc    2760
gcgttgctgg cgttttccca taggctccgc cccctgacg agcatcacaa aaatcgacgc    2820
tcaagtcaga ggtggcgaaa cccgacagga ctataaagat accaggcgtt ccccctgga    2880
agctccctcg tgcgctctcc tgttccgacc ctgccgctta ccggatacct gtccgccttt    2940
ctcccttcgg gaagcgtggc gctttctcat agctcacgct gtaggtatct cagttcggtg    3000
taggtcgttc gctccaagct gggctgtgtg cacgaacccc ccgttcagcc cgaccgctgc    3060
gccttatccg gtaactatcg tcttgagtcc aacccggtaa gacacgactt atcgccactg    3120
gcagcagcca ctggtaacag gattagcaga gcgaggtatg taggcggtgc tacagagttc    3180
ttgaagtggt ggcctaacta cggctacact agaagaacag tatttggtat ctgcgctctg    3240
ctgaagccag ttaccttcgg aaaaagagtt ggtagctctt gatccggcaa caaaccacc    3300
gctggtagcg gtggtttttt tgtttgcaag cagcagatta cgcgcagaaa aaaggatct    3360
caagaagatc ctttgatctt ttctacgggg tctgacgctc agtggaacga aaactcacgt    3420
taagggattt tggtcatgag attatcaaaa aggatcttca cctagatcct tttaaattaa    3480
aaatgaagtt ttaaatcaat ctaaagtata tatgagtaaa cttggtctga cagttaccaa    3540
tgcttaatca gtgaggcacc tatctcagcg atctgtctat ttcgttcatc catagttgcc    3600
```

```
tgactcccg tcgtgtagat aactacgata cgggagggct taccatctgg ccccagtgct    3660
gcaatgatac cgcgagaccc acgctcaccg gctccagatt tatcagcaat aaaccagcca    3720
gccggaaggg ccgagcgcag aagtggtcct gcaactttat ccgcctccat ccagtctatt    3780
aattgttgcc gggaagctag agtaagtagt tcgccagtta atagtttgcg caacgttgtt    3840
gccattgcta caggcatcgt ggtgtcacgc tcgtcgtttg gtatggcttc attcagctcc    3900
ggttcccaac gatcaaggcg agttacatga tcccccatgt tgtgcaaaaa agcggttagc    3960
tccttcggtc ctccgatcgt tgtcagaagt aagttggccg cagtgttatc actcatggtt    4020
atggcagcac tgcataattc tcttactgtc atgccatccg taagatgctt ttctgtgact    4080
ggtgagtact caaccaagtc attctgagaa tagtgtatgc ggcgaccgag ttgctcttgc    4140
ccggcgtcaa tacgggataa taccgcgcca catagcagaa ctttaaaagt gctcatcatt    4200
ggaaaacgtt cttcggggcg aaaactctca aggatcttac cgctgttgag atccagttcg    4260
atgtaaccca ctcgtgcacc caactgatct tcagcatctt ttactttcac cagcgtttct    4320
gggtgagcaa aaacaggaag gcaaaatgcc gcaaaaaagg aataagggc gacacggaaa    4380
tgttgaatac tcatactctt cctttttcaa tattattgaa gcatttatca gggttattgt    4440
ctcatgagcg gatacatatt tgaatgtatt tagaaaaata aacaaatagg ggttccgcgc    4500
acatttcccc gaaaagtgcc acctgacgcg ccctgtagcg cgcattaag cgcggcgggt    4560
gtggtggtta cgcgcagcgt gaccgctaca cttgccagcg ccctagcgcc cgctccttc    4620
gctttcttcc cttcctttct cgccacgttc gccggctttc cccgtcaagc tctaaatcgg    4680
gggctccctt tagggttccg atttagtgct ttacggcacc tcgaccccaa aaaacttgat    4740
tagggtgatg gttcacgtag tgggccatcg ccctgataga cggttttcg ccctttgacg    4800
ttggagtcca cgttctttaa tagtggactc ttgttccaaa ctggaacaac actcaaccct    4860
atctcggtct attcttttga tttataaggg attttgccga tttcggccta ttggttaaaa    4920
aatgagctga tttaacaaaa atttaacgcg aattttaaca aaatattaac gcttacaatt    4980
tgccattcgc cattcaggct gcgcaactgt tgggaagggc gatcggtgcg ggcctcttcg    5040
ctattacgcc agcccaagct accatgataa gtaagtaata ttaaggtacg ggaggtactt    5100
ggagcggccg caataaaata tctttatttt cattacatct gtgtgttggt ttttgtgtg    5160
aatcgatagt actaacatac gctctccatc aaaacaaaac gaaacaaaac aaactagcaa    5220
aataggctgt ccccagtgca agtgcaggtg ccagaacatt tctctatcga ta            5272
```

<210> SEQ ID NO 16  
<211> LENGTH: 5228  
<212> TYPE: DNA  
<213> ORGANISM: Artificial Sequence  
<220> FEATURE:  
<223> OTHER INFORMATION: pTac2-4x target

<400> SEQUENCE: 16

```
ggtaccgagc tcttacgcgt gctagcccgg gctcgagatc tgatatcaag taactttcgt     60
cactcattgt ttctaacttt cgtcactcat ggattctaac tttcgtcact catatcttct    120
aactttcgtc actcatcagt tcgcttacta gtgtcgaggt aggcgtgtac ggtgggaggc    180
ctatataagc agagctcgtt tagtgaaccg tcagatcgcc tggagtacc gccaccatgg    240
aagatgccaa aaacattaag aagggcccag cgccattcta cccactcgaa gacgggaccg    300
ccggcgagca gctgcacaaa gccatgaagc gctacgccct ggtgcccggc accatcgcct    360
```

-continued

```
ttaccgacgc acatatcgag gtggacatta cctacgccga gtacttcgag atgagcgttc      420
ggctggcaga agctatgaag cgctatgggc tgaatacaaa ccatcggatc gtggtgtgca      480
gcgagaatag cttgcagttc ttcatgcccg tgttgggtgc cctgttcatc ggtgtggctg      540
tggccccagc taacgacatc tacaacgagc gcgagctgct gaacagcatg ggcatcagcc      600
agcccaccgt cgtattcgtg agcaagaaag ggctgcaaaa gatcctcaac gtgcaaaaga      660
agctaccgat catacaaaag atcatcatca tggatagcaa gaccgactac cagggcttcc      720
aaagcatgta caccttcgtg acttcccatt tgccacccgg cttcaacgag tacgacttcg      780
tgcccgagag cttcgaccgg gacaaaacca tcgccctgat catgaacagt agtggcagta      840
ccggattgcc caagggcgta gccctaccgc accgcaccgc ttgtgtccga ttcagtcatg      900
cccgcgaccc catcttcggc aaccagatca tccccgacac cgctatcctc agcgtggtgc      960
catttcacca cggcttcggc atgttcacca cgctgggcta cttgatctgc ggctttcggg     1020
tcgtgctcat gtaccgcttc gaggaggagc tattcttgcg cagcttgcaa gactataaga     1080
ttcaatctgc cctgctggtg cccacactat ttagcttctt cgctaagagc actctcatcg     1140
acaagtacga cctaagcaac ttgcacgaga tcgccagcgg cggggcgccg ctcagcaagg     1200
aggtaggtga ggccgtggcc aaacgcttcc acctaccagg catccgccag ggctacggcc     1260
tgacagaaac aaccagcgcc attctgatca cccccgaagg ggacgacaag cctggcgcag     1320
taggcaaggt ggtgcccttc ttcgaggcta aggtggtgga cttggacacc ggtaagacac     1380
tgggtgtgaa ccagcgcggc gagctgtgcg tccgtggccc catgatcatg agcggctacg     1440
ttaacaaccc cgaggctaca aacgctctca tcgacaagga cggctggctg cacagcggcg     1500
acatcgccta ctgggacgag gacgagcact tcttcatcgt ggaccggctg aagagcctga     1560
tcaaatacaa gggctaccag gtagcccag ccgaactgga gagcatcctg ctgcaacacc     1620
ccaacatctt cgacgccggg gtcgccggcc tgcccgacga cgatgccggc gagctgcccg     1680
ccgcagtcgt cgtgctggaa cacggtaaaa ccatgaccga aaggagatc gtggactatg     1740 tggccagcca ggttacaacc gccaagaagc tgcgcggtgg tgttgtgttc gtggacgagg     1800
tgcctaaagg actgaccggc aagttggacg cccgcaagat ccgcgagatt ctcattaagg     1860
ccaagaaggg cggcaagatc gccgtgaatt cttaactgca gttaatctag agtcggggcg     1920
gccggccgct tcgagcagac atgataagat acattgatga gtttggacaa accacaacta     1980
gaatgcagtg aaaaaaatgc tttatttgtg aaatttgtga tgctattgct ttatttgtaa     2040
ccattataag ctgcaataaa caagttaaca acaacaattg cattcatttt atgtttcagg     2100 ttcagggga ggtgtgggag gttttttaaa gcaagtaaaa cctctacaaa tgtggtaaaa     2160
tcgataagga tctgaacgat ggagcggaga atgggcggaa ctgggcggag ttaggggcgg     2220
gatgggcgga gttaggggcg ggactatggt tgctgactaa ttgagatgca tgctttgcat     2280
acttctgcct gctggggagc ctggggactt tccacacctg gttgctgact aattgagatg     2340
catgctttgc atacttctgc ctgctgggga gcctggggac tttccacacc ctaactgaca     2400
cacattccac agcggatccg tcgaccgatg cccttgagag ccttcaaccc agtcagctcc     2460
ttccggtggg cgcggggcat gactatcgtc gccgcactta tgactgtctt ctttatcatg     2520
caactcgtag gacaggtgcc ggcagcgctc ttccgcttcc tcgctcactg actcgctgcg     2580
ctcggtcgtt cggctgcggc gagcggtatc agctcactca aaggcggtaa tacggttatc     2640
cacagaatca ggggataacg caggaaagaa catgtgagca aaaggccagc aaaaggccag     2700
gaaccgtaaa aaggccgcgt tgctggcgtt tttccatagg ctccgccccc ctgacgagca     2760
```

```
tcacaaaaat cgacgctcaa gtcagaggtg gcgaaacccg acaggactat aaagatacca    2820
ggcgtttccc cctggaagct ccctcgtgcg ctctcctgtt ccgaccctgc cgcttaccgg    2880
atacctgtcc gcctttctcc cttcgggaag cgtggcgctt tctcatagct cacgctgtag    2940
gtatctcagt tcggtgtagg tcgttcgctc caagctgggc tgtgtgcacg aaccccccgt    3000
tcagcccgac cgctgcgcct tatccggtaa ctatcgtctt gagtccaacc cggtaagaca    3060
cgacttatcg ccactggcag cagccactgg taacaggatt agcagagcga ggtatgtagg    3120
cggtgctaca gagttcttga agtggtggcc taactacggc tacactagaa gaacagtatt    3180
tggtatctgc gctctgctga agccagttac cttcggaaaa agagttggta gctcttgatc    3240
cggcaaacaa accaccgctg gtagcggtgg tttttttgtt tgcaagcagc agattacgcg    3300
cagaaaaaaa ggatctcaag aagatccttt gatcttttct acggggtctg acgctcagtg    3360
gaacgaaaac tcacgttaag ggattttggt catgagatta tcaaaaagga tcttcaccta    3420
gatcctttta aattaaaaat gaagttttaa atcaatctaa agtatatatg agtaaacttg    3480
gtctgacagt taccaatgct taatcagtga ggcacctatc tcagcgatct gtctatttcg    3540
ttcatccata gttgcctgac tccccgtcgt gtagataact acgatacggg agggcttacc    3600
atctggcccc agtgctgcaa tgataccgcg agacccacgc tcaccggctc cagatttatc    3660
agcaataaac cagccagccg gaagggccga gcgcagaagt ggtcctgcaa ctttatccgc    3720
ctccatccag tctattaatt gttgccggga agctagagta agtagttcgc cagttaatag    3780
tttgcgcaac gttgttgcca ttgctacagg catcgtggtg tcacgctcgt cgtttggtat    3840
ggcttcattc agctccggtt cccaacgatc aaggcgagtt acatgatccc ccatgttgtg    3900
caaaaaagcg gttagctcct tcggtcctcc gatcgttgtc agaagtaagt tggccgcagt    3960
gttatcactc atggttatgg cagcactgca taattctctt actgtcatgc catccgtaag    4020
atgcttttct gtgactggtg agtactcaac caagtcattc tgagaatagt gtatgcggcg    4080
accgagttgc tcttgcccgg cgtcaatacg ggataatacc gcgccacata gcagaacttt    4140
aaaagtgctc atcattggaa aacgttcttc ggggcgaaaa ctctcaagga tcttaccgct    4200
gttgagatcc agttcgatgt aacccactcg tgcacccaac tgatcttcag catcttttac    4260
tttcaccagc gtttctgggt gagcaaaaac aggaaggcaa aatgccgcaa aaaagggaat    4320
aagggcgaca cggaaatgtt gaatactcat actcttcctt tttcaatatt attgaagcat    4380
ttatcagggt tattgtctca tgagcggata catatttgaa tgtatttaga aaaataaaca    4440
aataggggtt ccgcgcacat ttccccgaaa agtgccacct gacgcgccct gtagcggcgc    4500
attaagcgcg gcgggtgtgg tggttacgcg cagcgtgacc gctacacttg ccagcgccct    4560
agcgcccgct cctttcgctt tcttcccttc ctttctcgcc acgttcgccg gctttccccg    4620
tcaagctcta aatcggggc tcccttagg gttccgattt agtgctttac ggcacctcga    4680
ccccaaaaaa cttgattagg gtgatggttc acgtagtggg ccatcgccct gatagacggt    4740
ttttcgccct ttgacgttgg agtccacgtt ctttaatagt ggactcttgt tccaaactgg    4800
aacaacactc aaccctatct cggtctattc ttttgattta agggatttt tgccgatttc    4860 ggcctattgg ttaaaaaatg agctgattta acaaaaattt aacgcgaatt ttaacaaaat    4920
attaacgctt acaatttgcc attcgccatt caggctgcgc aactgttggg aagggcgatc    4980
ggtgcgggcc tcttcgctat tacgccagcc caagctacca tgataagtaa gtaatattaa    5040
ggtacgggag gtacttggag cggccgcaat aaaatatctt tattttcatt acatctgtgt    5100
```

```
gttggttttt tgtgtgaatc gatagtacta acatacgctc tccatcaaaa caaaacgaaa    5160
caaaacaaac tagcaaaata ggctgtcccc agtgcaagtg caggtgccag aacatttctc    5220
tatcgata                                                             5228

<210> SEQ ID NO 17
<211> LENGTH: 5320
<212> TYPE: DNA
<213> ORGANISM: Artificial Sequence
<220> FEATURE:
<223> OTHER INFORMATION: pTac2-8x target

<400> SEQUENCE: 17
ggtaccgagc tcttacgcgt gctagcccgg gctcgagatc tgatatcaag taactttcgt      60
cactcatcca tggtaacttt cgtcactcat cacgactaac tttcgtcact cattgtttct     120
aactttcgtc actcatgaat ctaactttc gtcactcata agttctaact ttcgtcactc     180
atttcgaata actttcgtca ctcatatctt ctaactttcg tcactcatca gttcgcttac     240
tagtgtcgag gtaggcgtgt acggtgggag gcctatataa gcagagctcg tttagtgaac     300
cgtcagatcg cctggaggta ccgccaccat ggaagatgcc aaaaacatta agaagggccc     360
agcgccattc tacccactcg aagacgggac cgccggcgag cagctgcaca agccatgaa      420 gcgctacgcc ctggtgcccg gcaccatcgc ctttaccgac gcacatatcg aggtggacat     480
tacctacgcc gagtacttcg agatgagcgt cggctggca gaagctatga agcgctatgg      540
gctgaataca aaccatcgga tcgtggtgtg cagcgagaat agcttgcagt tcttcatgcc     600
cgtgttgggt gccctgttca tcggtgtggc tgtggcccca gctaacgaca tctacaacga     660
gcgcgagctg ctgaacagca tgggcatcag ccagcccacc gtcgtattcg tgagcaagaa     720
agggctgcaa aagatcctca acgtgcaaaa gaagctaccg atcatacaaa agatcatcat     780
catggatagc aagaccgact accagggctt ccaaagcatg tacaccttcg tgacttccca     840
tttgccaccc ggcttcaacg agtacgactt cgtgcccgag agcttcgacc gggacaaaac     900
catcgccctg atcatgaaca gtagtggcag taccggattg cccaagggcg tagccctacc     960
gcaccgcacc gcttgtgtcc gattcagtca tgcccgcgac cccatcttcg caaccagat    1020 catccccgac accgctatcc tcagcgtggt gccatttcac cacggcttcg gcatgttcac    1080
cacgctgggc tacttgatct gcggctttcg ggtcgtgctc atgtaccgct tcgaggagga    1140
gctattcttg cgcagcttgc aagactataa gattcaatct gccctgctgg tgcccacact    1200
atttagcttc ttcgctaaga gcactctcat cgacaagtac gacctaagca acttgcacga    1260
gatcgccagc ggcggggcgc cgctcagcaa ggaggtaggt gaggccgtgg ccaaacgctt    1320
ccacctacca ggcatccgcc agggctacgg cctgacagaa caaccagcg ccattctgat     1380 cacccccgaa ggggacgaca gcctggcgc agtaggcaag gtggtgccct tcttcgaggc    1440
taaggtggtg gacttggaca ccggtaagac actgggtgtg aaccagcgcg gcagagctgtg    1500 cgtccgtggc cccatgatca tgagcggcta cgttaacaac cccgaggcta caacgctct     1560 catcgacaag gacggctggc tgcacagcgg cgacatcgcc tactgggacg aggacgagca    1620
cttcttcatc gtggaccggc tgaagagcct gatcaaatac aagggctacc aggtagcccc    1680
agccgaactg gagagcatcc tgctgcaaca ccccaacatc ttcgacgccg ggtcgccgg    1740 cctgcccgac gacgatgccg cgagctgcc cgccgcagtc gtcgtgctgg aacacggtaa    1800
aaccatgacc gagaaggaga tcgtggacta tgtggccagc caggttacaa ccgccaagaa    1860
gctgcgcggt ggtgttgtgt tcgtggacga ggtgcctaaa ggactgaccg gcaagttgga    1920
```

```
cgcccgcaag atccgcgaga ttctcattaa ggccaagaag ggcggcaaga tcgccgtgaa    1980
ttcttaactg cagttaatct agagtcgggg cggccggccg cttcgagcag acatgataag    2040
atacattgat gagtttggac aaaccacaac tagaatgcag tgaaaaaaat gctttatttg    2100
tgaaatttgt gatgctattg ctttatttgt aaccattata agctgcaata aacaagttaa    2160
caacaacaat tgcattcatt ttatgtttca ggttcagggg gaggtgtggg aggttttta     2220 aagcaagtaa aacctctaca aatgtggtaa aatcgataag gatctgaacg atggagcgga    2280
gaatgggcgg aactgggcgg agttaggggc gggatgggcg gagttagggg cgggactatg    2340
gttgctgact aattgagatg catgctttgc atacttctgc ctgctgggga gcctggggac    2400
tttccacacc tggttgctga ctaattgaga tgcatgcttt gcatacttct gcctgctggg    2460
gagcctgggg actttccaca ccctaactga cacacattcc acagcggatc cgtcgaccga    2520
tgcccttgag agccttcaac ccagtcagct ccttccggtg ggcgcggggc atgactatcg    2580
tcgccgcact tatgactgtc ttctttatca tgcaactcgt aggacaggtg ccggcagcgc    2640
tcttccgctt cctcgctcac tgactcgctg cgctcggtcg ttcggctgcg gcgagcggta    2700
tcagctcact caaaggcggt aatacggtta tccacagaat cagggaataa cgcaggaaag    2760
aacatgtgag caaaaggcca gcaaaaggcc aggaaccgta aaaaggccgc gttgctggcg    2820 ttttccata ggctccgccc ccctgacgag catcacaaaa atcgacgctc aagtcagagg     2880
tggcgaaacc cgacaggact ataaagatac caggcgtttc ccccggaag ctccctcgtg     2940 cgctctcctg ttccgaccct gccgcttacc ggatacctgt ccgcctttct cccttcggga    3000
agcgtggcgc tttctcatag ctcacgctgt aggtatctca gttcggtgta ggtcgttcgc    3060
tccaagctgg gctgtgtgca cgaaccccc gttcagcccg accgctgcgc cttatccggt      3120
aactatcgtc ttgagtccaa cccggtaaga cacgacttat cgccactggc agcagccact    3180
ggtaacagga ttagcagagc gaggtatgta ggcggtgcta cagagttctt gaagtggtgg    3240
cctaactacg gctacactag aagaacagta tttggtatct gcgctctgct gaagccagtt    3300
accttcggaa aaagagttgg tagctcttga tccggcaaac aaaccaccgc tggtagcggt    3360
ggtttttttg tttgcaagca gcagattacg cgcagaaaaa aaggatctca agaagatcct    3420
ttgatctttt ctacggggtc tgacgctcag tggaacgaaa actcacgtta agggattttg    3480
gtcatgagat tatcaaaaag gatcttcacc tagatccttt taaattaaaa atgaagtttt    3540
aaatcaatct aaagtatata tgagtaaact tggtctgaca gttaccaatg cttaatcagt    3600
gaggcaccta tctcagcgat ctgtctattt cgttcatcca tagttgcctg actccccgtc    3660
gtgtagataa ctacgatacg ggagggctta ccatctggcc ccagtgctgc aatgataccg    3720
cgagacccac gctcaccggc tccagattta tcagcaataa accagccagc cggaagggcc    3780
gagcgcagaa gtggtcctgc aactttatcc gcctccatcc agtctattaa ttgttgccgg    3840
gaagctagag taagtagttc gccagttaat agtttgcgca acgttgttgc cattgctaca    3900
ggcatcgtgg tgtcacgctc gtcgtttggt atggcttcat tcagctccgg ttcccaacga    3960
tcaaggcgag ttacatgatc ccccatgttg tgcaaaaaag cggttagctc cttcggtcct    4020
ccgatcgttg tcagaagtaa gttggccgca gtgttatcac tcatggttat ggcagcactg    4080
cataattctc ttactgtcat gccatccgta agatgctttt ctgtgactgg tgagtactca    4140
accaagtcat tctgagaata gtgtatgcgg cgaccgagtt gctcttgccc ggcgtcaata    4200
cgggataata ccgcgccaca tagcagaact ttaaaagtgc tcatcattgg aaaacgttct    4260
```

```
tcggggcgaa aactctcaag gatcttaccg ctgttgagat ccagttcgat gtaacccact   4320
cgtgcaccca actgatcttc agcatctttt actttcacca gcgtttctgg gtgagcaaaa   4380
acaggaaggc aaaatgccgc aaaaaaggga ataagggcga cacggaaatg ttgaatactc   4440
atactcttcc ttttcaata ttattgaagc atttatcagg gttattgtct catgagcgga   4500
tacatatttg aatgtattta gaaaaataaa caaatagggg ttccgcgcac atttccccga   4560
aaagtgccac ctgacgcgcc ctgtagcggc gcattaagcg cggcgggtgt ggtggttacg   4620
cgcagcgtga ccgctacact tgccagcgcc ctagcgcccg ctcctttcgc tttcttccct   4680
tcctttctcg ccacgttcgc cggctttccc cgtcaagctc taaatcgggg ctcccttta    4740 gggttccgat ttagtgcttt acggcacctc gaccccaaaa aacttgatta gggtgatggt   4800
tcacgtagtg ggccatcgcc ctgatagacg ttttttcgcc ctttgacgtt ggagtccacg   4860
ttctttaata gtggactctt gttccaaact ggaacaacac tcaaccctat ctcggtctat   4920
tcttttgatt tataagggat tttgccgatt tcggcctatt ggttaaaaaa tgagctgatt   4980
taacaaaaat ttaacgcgaa ttttaacaaa atattaacgc ttacaatttg ccattcgcca   5040
ttcaggctgc gcaactgttg ggaagggcga tcggtgcggg cctcttcgct attacgccag   5100
cccaagctac catgataagt aagtaatatt aaggtacggg aggtacttgg agcggccgca   5160
ataaaatatc tttatttca ttacatctgt gtgttggttt tttgtgtgaa tcgatagtac   5220
taacatacgc tctccatcaa aacaaaacga aacaaaacaa actagcaaaa taggctgtcc   5280
ccagtgcaag tgcaggtgcc agaacatttc tctatcgata                        5320

<210> SEQ ID NO 18
<211> LENGTH: 5212
<212> TYPE: DNA
<213> ORGANISM: Artificial Sequence
<220> FEATURE:
<223> OTHER INFORMATION: GUN1-4x target

<400> SEQUENCE: 18
ggtaccgagc tcttacgcgt gctagcccgg gctcgagatc tgatatcaag taatttgtcg     60
atttgtttct aatttgtcga ttgaattcta atttgtcgat tatcttctaa tttgtcgatt    120
cagttcgctt actagtgtcg aggtaggcgt gtacggtggg aggcctatat aagcagagct    180
cgtttagtga accgtcagat cgcctggagg taccgccacc atggaagatg ccaaaaacat    240
taagaagggc ccagcgccat tctacccact cgaagacggg accgccggcg agcagctgca    300
caaagccatg aagcgctacg ccctggtgcc cggcaccatc gccttaccg acgcacatat    360 cgaggtggac attacctacg ccgagtactt cgagatgagc gttcggctgg cagaagctat    420
gaagcgctat gggctgaata caaaccatcg gatcgtggtg tgcagcgaga atagcttgca    480
gttcttcatg cccgtgttgg gtgccctgtt catcggtgtg gctgtggccc cagctaacga    540
catctacaac gagcgcgagc tgctgaacag catgggcatc agccagccca ccgtcgtatt    600
cgtgagcaag aaagggctgc aaaagatcct caacgtgcaa aagaagctac cgatcataca    660
aaagatcatc atcatggata gcaagaccga ctaccagggc ttccaaagca tgtacacctt    720
cgtgacttcc catttgccac ccggcttcaa cgagtacgac ttcgtgcccg agagcttcga    780
ccgggacaaa accatcgccc tgatcatgaa cagtagtggc agtaccggat tgcccaaggg    840
cgtagcccta ccgcaccgca ccgcttgtgt ccgattcagt catgcccgcg accccatctt    900
cggcaaccag atcatccccg acaccgctat cctcagcgtg gtgccatttc accacggctt    960
cggcatgttc accacgctgg gctacttgat ctgcggcttt cgggtcgtgc tcatgtaccg   1020
```

```
cttcgaggag gagctattct tgcgcagctt gcaagactat aagattcaat ctgccctgct   1080
ggtgcccaca ctatttagct tcttcgctaa gagcactctc atcgacaagt acgacctaag   1140
caacttgcac gagatcgcca gcggcggggc gccgctcagc aaggaggtag gtgaggccgt   1200
ggccaaacgc ttccacctac caggcatccg ccagggctac ggcctgacag aaacaaccag   1260
cgccattctg atcaccccg aaggggacga caagcctggc gcagtaggca aggtggtgcc   1320
cttcttcgag gctaaggtgg tggacttgga caccggtaag acactgggtg tgaaccagcg   1380
cggcgagctg tgcgtccgtg gccccatgat catgagcggc tacgttaaca accccgaggc   1440
tacaaacgct ctcatcgaca aggacggctg gctgcacagc ggcgacatcg cctactggga   1500
cgaggacgag cacttcttca tcgtggaccg gctgaagagc ctgatcaaat acaagggcta   1560
ccaggtagcc ccagccgaac tggagagcat cctgctgcaa caccccaaca tcttcgacgc   1620
cggggtcgcc ggcctgcccg acgacgatgc cggcgagctg cccgccgcag tcgtcgtgct   1680
ggaacacggt aaaaccatga ccgagaagga gatcgtggac tatgtggcca gccaggttac   1740
aaccgccaag aagctgcgcg tggtgttgt gttcgtggac gaggtgccta aaggactgac   1800
cggcaagttg gacgcccgca agatccgcga gattctcatt aaggccaaga agggcggcaa   1860
gatcgccgtg aattcttaac tgcagttaat ctagagtcgg ggcggccggc cgcttcgagc   1920
agacatgata agatacattg atgagtttgg acaaaccaca actagaatgc agtgaaaaaa   1980
atgctttatt tgtgaaattt gtgatgctat tgctttattt gtaaccatta aagctgcaa   2040 taaacaagtt aacaacaaca attgcattca ttttatgttt caggttcagg gggaggtgtg   2100
ggaggttttt taaagcaagt aaaacctcta caaatgtggt aaaatcgata aggatctgaa   2160
cgatggagcg gagaatgggc ggaactgggc ggagttaggg gcgggatggg cggagttagg   2220
ggcgggacta tggttgctga ctaattgaga tgcatgcttt gcatacttct gcctgctggg   2280
gagcctgggg actttccaca cctggttgct gactaattga gatgcatgct ttgcatactt   2340
ctgcctgctg gggagcctgg ggactttcca caccctaact gacacacatt ccacagcgga   2400
tccgtcgacc gatgcccttg agagccttca acccagtcag ctccttccgg tgggcgcggg   2460
gcatgactat cgtcgccgca cttatgactg tcttctttat catgcaactc gtaggacagg   2520
tgccggcagc gctcttccgc ttcctcgctc actgactcgc tgcgctcggt cgttcggctg   2580
cggcgagcgg tatcagctca ctcaaaggcg gtaatacggt tatccacaga atcagggat   2640 aacgcaggaa agaacatgtg agcaaaaggc cagcaaaagg ccaggaaccg taaaaaggcc   2700
gcgttgctgg cgttttttcca taggctccgc cccctgacg agcatcacaa aaatcgacgc   2760
tcaagtcaga ggtggcgaaa cccgacagga ctataaagat accaggcgtt ccccctgga   2820 agctccctcg tgcgctctcc tgttccgacc ctgccgctta ccggatacct gtccgccttt   2880
ctcccttcgg gaagcgtggc gctttctcat agctcacgct gtaggtatct cagttcggtg   2940
taggtcgttc gctccaagct gggctgtgtg cacgaacccc ccgttcagcc cgaccgctgc   3000
gccttatccg gtaactatcg tcttgagtcc aacccggtaa gacacgactt atcgccactg   3060
gcagcagcca ctggtaacag gattagcaga gcgaggtatg taggcggtgc tacagagttc   3120
ttgaagtggt ggcctaacta cggctacact agaagaacag tatttggtat ctgcgctctg   3180
ctgaagccag ttaccttcgg aaaaagagtt ggtagctctt gatccggcaa caaaccacc   3240 gctggtagcg gtggtttttt tgtttgcaag cagcagatta cgcgcagaaa aaaggatct   3300 caagaagatc ctttgatctt ttctacgggg tctgacgctc agtggaacga aaactcacgt   3360
```

```
taagggattt tggtcatgag attatcaaaa aggatcttca cctagatcct tttaaattaa    3420
aaatgaagtt ttaaatcaat ctaaagtata tatgagtaaa cttggtctga cagttaccaa    3480
tgcttaatca gtgaggcacc tatctcagcg atctgtctat ttcgttcatc catagttgcc    3540
tgactccccg tcgtgtagat aactacgata cgggagggct taccatctgg ccccagtgct    3600
gcaatgatac cgcgagaccc acgctcaccg gctccagatt tatcagcaat aaaccagcca    3660
gccggaaggg ccgagcgcag aagtggtcct gcaactttat ccgcctccat ccagtctatt    3720
aattgttgcc gggaagctag agtaagtagt tcgccagtta atagtttgcg caacgttgtt    3780
gccattgcta caggcatcgt ggtgtcacgc tcgtcgtttg gtatggcttc attcagctcc    3840
ggttcccaac gatcaaggcg agtacatga tcccccatgt tgtgcaaaaa agcggttagc    3900
tccttcggtc ctccgatcgt tgtcagaagt aagttggccg cagtgttatc actcatggtt    3960
atggcagcac tgcataattc tcttactgtc atgccatccg taagatgctt ttctgtgact    4020
ggtgagtact caaccaagtc attctgagaa tagtgtatgc ggcgaccgag ttgctcttgc    4080
ccggcgtcaa tacgggataa taccgcgcca catagcagaa ctttaaaagt gctcatcatt    4140
ggaaaacgtt cttcggggcg aaaactctca aggatcttac cgctgttgag atccagttcg    4200
atgtaaccca ctcgtgcacc caactgatct tcagcatctt ttactttcac cagcgtttct    4260
gggtgagcaa aaacaggaag gcaaaatgcc gcaaaaaagg gaataagggc gacacggaaa    4320
tgttgaatac tcatactctt cctttttcaa tattattgaa gcatttatca gggttattgt    4380
ctcatgagcg gatacatatt tgaatgtatt tagaaaaata aacaaatagg ggttccgcgc    4440
acatttcccc gaaaagtgcc acctgacgcg ccctgtagcg gcgcattaag cgcggcgggt    4500
gtggtggtta cgcgcagcgt gaccgctaca cttgccagcg ccctagcgcc cgctcctttc    4560
gctttcttcc cttcctttct cgccacgttc gccggctttc cccgtcaagc tctaaatcgg    4620
gggctcccTT tagggttccg atttagtgct ttacggcacc tcgaccccaa aaaacttgat    4680
tagggtgatg gttcacgtag tgggccatcg ccctgataga cggtttttcg ccctttgacg    4740
ttggagtcca cgttctttaa tagtggactc ttgttccaaa ctggaacaac actcaaccct    4800
atctcggtct attcttttga tttataaggg attttgccga tttcggccta ttggttaaaa    4860
aatgagctga tttaacaaaa atttaacgcg aattttaaca aaatattaac gcttacaatt    4920
tgccattcgc cattcaggct gcgcaactgt tgggaagggc gatcggtgcg ggcctcttcg    4980
ctattacgcc agcccaagct accatgataa gtaagtaata ttaaggtacg ggaggtactt    5040
ggagcggccg caataaaata tctttatttt cattacatct gtgtgttggt tttttgtgtg    5100
aatcgatagt actaacatac gctctccatc aaaacaaaac gaaacaaaac aaactagcaa    5160
aataggctgt ccccagtgca agtgcaggtg ccagaacatt tctctatcga ta            5212
```

<210> SEQ ID NO 19
<211> LENGTH: 5288
<212> TYPE: DNA
<213> ORGANISM: Artificial Sequence
<220> FEATURE:
<223> OTHER INFORMATION: GUN1-8x target

<400> SEQUENCE: 19

```
ggtaccgagc tcttacgcgt gctagcccgg gctcgagatc tgatatcaag taatttgtcg      60
attccatggt aatttgtcga ttcacgacta atttgtcgat tgttttctaa tttgtcgatt     120
gaattctaat ttgtcgatta agttctaatt tgtcgatttt cgaataattt gtcgattatc     180
ttctaatttg tcgattcagt tcgcttacta gtgtcgaggt aggcgtgtac ggtgggaggc     240
```

| | |
|---|---|
| ctatataagc agagctcgtt tagtgaaccg tcagatcgcc tggaggtacc gccaccatgg | 300 |
| aagatgccaa aaacattaag aagggcccag cgccattcta cccactcgaa gacgggaccg | 360 |
| ccggcgagca gctgcacaaa gccatgaagc gctacgccct ggtgcccggc accatcgcct | 420 |
| ttaccgacgc acatatcgag gtggacatta cctacgccga gtacttcgag atgagcgttc | 480 |
| ggctggcaga agctatgaag cgctatgggc tgaatacaaa ccatcggatc gtggtgtgca | 540 |
| gcgagaatag cttgcagttc ttcatgcccg tgttgggtgc cctgttcatc ggtgtggctg | 600 |
| tggccccagc taacgacatc tacaacgagc gcgagctgct gaacagcatg ggcatcagcc | 660 |
| agcccaccgt cgtattcgtg agcaagaaag ggctgcaaaa gatcctcaac gtgcaaaaga | 720 |
| agctaccgat catacaaaag atcatcatca tggatagcaa gaccgactac cagggcttcc | 780 |
| aaagcatgta caccttcgtg acttcccatt tgccacccgg cttcaacgag tacgacttcg | 840 |
| tgcccgagag cttcgaccgg gacaaaacca tcgccctgat catgaacagt agtggcagta | 900 |
| ccggattgcc caagggcgta gccctaccgc accgcaccgc ttgtgtccga ttcagtcatg | 960 |
| cccgcgaccc catcttcggc aaccagatca tccccgacac cgctatcctc agcgtggtgc | 1020 |
| catttcacca cggcttcggc atgttcacca cgctgggcta cttgatctgc ggctttcggg | 1080 |
| tcgtgctcat gtaccgcttc gaggaggagc tattcttgcg cagcttgcaa gactataaga | 1140 |
| ttcaatctgc cctgctggtg cccacactat ttagcttctt cgctaagagc actctcatcg | 1200 |
| acaagtacga cctaagcaac ttgcacgaga tcgccagcgg cggggcgccg ctcagcaagg | 1260 |
| aggtaggtga ggccgtggcc aaacgcttcc acctaccagg catccgccag ggctacggcc | 1320 |
| tgacagaaac aaccagcgcc attctgatca cccccgaagg ggacgacaag cctggcgcag | 1380 |
| taggcaaggt ggtgcccttc ttcgaggcta aggtggtgga cttggacacc ggtaagacac | 1440 |
| tgggtgtgaa ccagcgcggc gagctgtgcg tccgtggccc catgatcatg agcggctacg | 1500 |
| ttaacaaccc cgaggctaca aacgctctca tcgacaagga cggctggctg cacagcggcg | 1560 |
| acatcgccta ctgggacgag gacgagcact tcttcatcgt ggaccggctg aagagcctga | 1620 |
| tcaaatacaa gggctaccag gtagccccag ccgaactgga gagcatcctg ctgcaacacc | 1680 |
| ccaacatctt cgacgccggg gtcgccggcc tgcccgacga cgatgccggc gagctgcccg | 1740 |
| ccgcagtcgt cgtgctggaa cacggtaaaa ccatgaccga aaggagatc gtggactatg | 1800 |
| tggccagcca ggttacaacc gccaagaagc tgcgcgtgg tgttgtgttc gtggacgagg | 1860 |
| tgcctaaagg actgaccggc aagttggacg cccgcaagat ccgcgagatt ctcattaagg | 1920 |
| ccaagaaggg cggcaagatc gccgtgaatt cttaactgca gttaatctag agtcggggcg | 1980 |
| gccggccgct tcgagcagac atgataagat acattgatga gtttggacaa accacaacta | 2040 |
| gaatgcagtg aaaaaaatgc tttatttgtg aaatttgtga tgctattgct ttatttgtaa | 2100 |
| ccattataag ctgcaataaa caagttaaca acaacaattg cattcatttt atgtttcagg | 2160 |
| ttcaggggga ggtgtgggag gttttttaaa gcaagtaaaa cctctacaaa tgtggtaaaa | 2220 |
| tcgataagga tctgaacgat ggagcggaga atgggcggaa ctgggcggag ttaggggcgg | 2280 |
| gatgggcggg gttaggggcg ggactatggt tgctgactaa ttgagatgca tgctttgcat | 2340 |
| acttctgcct gctggggagc ctggggactt tccacacctg gttgctgact aattgagatg | 2400 |
| catgctttgc atacttctgc ctgctgggga gctggggac tttccacacc ctaactgaca | 2460 |
| cacattccac agcggatccg tcgaccgatg cccttgagag ccttcaaccc agtcagctcc | 2520 |
| ttccggtggg cgcggggcat gactatcgtc gccgcactta tgactgtctt ctttatcatg | 2580 |

```
caactcgtag gacaggtgcc ggcagcgctc ttccgcttcc tcgctcactg actcgctgcg    2640
ctcggtcgtt cggctgcggc gagcggtatc agctcactca aaggcggtaa tacggttatc    2700
cacagaatca ggggataacg caggaaagaa catgtgagca aaaggccagc aaaaggccag    2760
gaaccgtaaa aaggccgcgt tgctggcgtt tttccatagg ctccgccccc ctgacgagca    2820
tcacaaaaat cgacgctcaa gtcagaggtg gcgaaacccg acaggactat aaagatacca    2880
ggcgtttccc cctggaagct ccctcgtgcg ctctcctgtt ccgaccctgc cgcttaccgg    2940
atacctgtcc gcctttctcc cttcgggaag cgtggcgctt tctcatagct cacgctgtag    3000
gtatctcagt tcggtgtagg tcgttcgctc caagctgggc tgtgtgcacg aaccccccgt    3060
tcagcccgac cgctgcgcct tatccggtaa ctatcgtctt gagtccaacc cggtaagaca    3120
cgacttatcg ccactggcag cagccactgg taacaggatt agcagagcga ggtatgtagg    3180
cggtgctaca gagttcttga agtggtggcc taactacggc tacactagaa gaacagtatt    3240
tggtatctgc gctctgctga agccagttac cttcggaaaa agagttggta gctcttgatc    3300
cggcaaacaa accaccgctg gtagcggtgg ttttttttgtt tgcaagcagc agattacgcg    3360
cagaaaaaaa ggatctcaag aagatccttt gatcttttct acggggtctg acgctcagtg    3420
gaacgaaaac tcacgttaag ggattttggt catgagatta tcaaaaagga tcttcaccta    3480 gatccttttta aattaaaaat gaagttttaa atcaatctaa agtatatatg agtaaacttg    3540
gtctgacagt taccaatgct taatcagtga ggcacctatc tcagcgatct gtctatttcg    3600
ttcatccata gttgcctgac tccccgtcgt gtagataact acgatacggg agggcttacc    3660
atctggcccc agtgctgcaa tgataccgcg agacccacgc tcaccggctc cagatttatc    3720
agcaataaac cagccagccg gaagggccga gcgcagaagt ggtcctgcaa ctttatccgc    3780
ctccatccag tctattaatt gttgccggga agctagagta agtagttcgc cagttaatag    3840
tttgcgcaac gttgttgcca ttgctacagg catcgtggtg tcacgctcgt cgtttggtat    3900
ggcttcattc agctccggtt cccaacgatc aaggcgagtt acatgatccc ccatgttgtg    3960
caaaaaagcg gttagctcct tcggtcctcc gatcgttgtc agaagtaagt tggccgcagt    4020
gttatcactc atggttatgg cagcactgca taattctctt actgtcatgc catccgtaag    4080
atgcttttct gtgactggtg agtactcaac caagtcattc tgagaatagt gtatgcggcg    4140
accgagttgc tcttgcccgg cgtcaatacg ggataatacc gcgccacata gcagaacttt    4200
aaaagtgctc atcattggaa aacgttcttc ggggcgaaaa ctctcaagga tcttaccgct    4260
gttgagatcc agttcgatgt aacccactcg tgcacccaac tgatcttcag catcttttac    4320
tttcaccagc gtttctgggt gagcaaaaac aggaaggcaa aatgccgcaa aaaagggaat    4380
aagggcgaca cggaaatgtt gaatactcat actcttcctt tttcaatatt attgaagcat    4440
ttatcagggt tattgtctca tgagcggata catatttgaa tgtatttaga aaaataaaca    4500
aataggggtt ccgcgcacat ttccccgaaa agtgccacct gacgcgccct gtagcggcgc    4560
attaagcgcg gcgggtgtgg tggttacgcg cagcgtgacc gctacacttg ccagcgccct    4620
agcgcccgct cctttcgctt tcttcccttc ctttctcgcc acgttcgccg gctttccccg    4680
tcaagctcta aatcggggc tcccttttagg gttccgattt agtgctttac ggcacctcga    4740
ccccaaaaaa cttgattagg gtgatggttc acgtagtggg ccatcgccct gatagacggt    4800
ttttcgccct ttgacgttgg agtccacgtt ctttaatagt ggactcttgt tccaaactgg    4860
aacaacactc aaccctatct cggtctattc ttttgattta agggatttt tgccgatttc    4920 ggcctattgg ttaaaaaatg agctgattta acaaaaattt aacgcgaatt ttaacaaaat    4980
```

```
attaacgctt acaatttgcc attcgccatt caggctgcgc aactgttggg aagggcgatc      5040
ggtgcgggcc tcttcgctat tacgccagcc caagctacca tgataagtaa gtaatattaa      5100
ggtacgggag gtacttggag cggccgcaat aaaatatctt tattttcatt acatctgtgt      5160
gttggttttt tgtgtgaatc gatagtacta acatacgctc tccatcaaaa caaaacgaaa      5220
caaaacaaac tagcaaaata ggctgtcccc agtgcaagtg caggtgccag aacatttctc      5280
tatcgata                                                              5288
```